United States Patent
Dietz et al.

(10) Patent No.: US 11,938,135 B2
(45) Date of Patent: Mar. 26, 2024

(54) COMPOSITIONS AND METHODS FOR TREATING VASCULAR EHLERS DANLOS SYNDROME AND ASSOCIATED DISORDERS

(71) Applicant: The Johns Hopkins University, Baltimore, MD (US)

(72) Inventors: Harry C. Dietz, Towson, MD (US); Caitlin J. Bowen, Baltimore, MD (US); Juan Francisco Calderon Giadrosic, Santiago (CL)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 17/286,414

(22) PCT Filed: Oct. 16, 2019

(86) PCT No.: PCT/US2019/056616
§ 371 (c)(1),
(2) Date: Apr. 16, 2021

(87) PCT Pub. No.: WO2020/081741
PCT Pub. Date: Apr. 23, 2020

(65) Prior Publication Data
US 2021/0386740 A1 Dec. 16, 2021

Related U.S. Application Data

(60) Provisional application No. 62/838,049, filed on Apr. 24, 2019, provisional application No. 62/747,587, filed on Oct. 18, 2018, provisional application No. 62/746,524, filed on Oct. 16, 2018.

(51) Int. Cl.
| | | |
|---|---|---|
| A61K 31/517 | (2006.01) |
| A61K 31/353 | (2006.01) |
| A61K 31/407 | (2006.01) |
| A61K 31/4184 | (2006.01) |
| A61K 31/436 | (2006.01) |
| A61K 31/4523 | (2006.01) |
| A61K 31/4545 | (2006.01) |
| A61K 31/502 | (2006.01) |
| A61K 31/506 | (2006.01) |
| A61K 31/519 | (2006.01) |
| A61K 31/537 | (2006.01) |
| A61K 31/58 | (2006.01) |
| A61K 31/69 | (2006.01) |
| A61K 39/395 | (2006.01) |
| A61P 9/14 | (2006.01) |

(52) U.S. Cl.
CPC .......... *A61K 31/517* (2013.01); *A61K 31/353* (2013.01); *A61K 31/407* (2013.01); *A61K 31/4184* (2013.01); *A61K 31/436* (2013.01); *A61K 31/4523* (2013.01); *A61K 31/4545* (2013.01); *A61K 31/502* (2013.01); *A61K 31/506* (2013.01); *A61K 31/519* (2013.01); *A61K 31/537* (2013.01); *A61K 31/58* (2013.01); *A61K 31/69* (2013.01); *A61K 39/3955* (2013.01); *A61P 9/14* (2018.01)

(58) Field of Classification Search
CPC ... A61P 9/14; A61K 31/4015; A61K 31/4523; A61K 31/502; A61K 31/517; A61K 31/519
See application file for complete search history.

(56) References Cited

U.S. PATENT DOCUMENTS 4,522,811 A  6/1985  Eppstein et al.

FOREIGN PATENT DOCUMENTS

| DE | 102004019413 A1 | 11/2005 |
| WO | 2017079399 A1 | 5/2017 |
| WO | 2018160987 A1 | 9/2018 |
| WO | 2020081741 A2 | 4/2020 |

OTHER PUBLICATIONS

Morissette et al. Circ. Cardiovasc. Genet. 2014, vol. 7, pp. 80-88 (Year: 2014).*
Briest et al. (Jun. 2011) "Doxycycline Ameliorates the Susceptibility to Aortic Lesions in a Mouse Model for the Vascular Type of Ehlers-danlos Syndrome", Journal of Pharmacology and Experimental Therapeutics, 337(3):621-627.
D'Hondt et al. (Sep. 2018) "Type III Collagen Affects Dermal and Vascular Collagen Fibrillogenesis and Tissue Integrity in a Mutant Col3a1 Transgenic Mouse Model", Matrix Biology, 70:72-83.
Doyle et al. (Oct. 27, 2015) "A Deleterious Gene-by-Environment Interaction Imposed by Calcium Channel Blockers in Marfan Syndrome", eLife, 4 e08648:18 pages.
Gurney et al. (Jan. 1995) "Inhibition of Calcium Release From the Sarcoplasmic Reticulum of Rabbit Aorta by Hydralazine", British Journal of Pharmacology, 114(1):238-244.
Habashi et al. (Apr. 15, 2011) "Angiotensin II Type 2 Receptor Signaling Attenuates Aortic Aneurysm in Mice Through ERK Antagonism", Science, 332(6027):8 Pages.
Habashi et al. (Apr. 7, 2006) "Losartan, an AT1 Antagonist, Prevents Aortic Aneurysm in a Mouse Model of Marfan Syndrome", Science, 312(5770):12 Pages.

(Continued)

*Primary Examiner* — James D. Anderson
(74) *Attorney, Agent, or Firm* — Fox Rothschild LLP

(57) ABSTRACT

The present invention relates to compositions and methods for treating vascular Ehlers Danlos Syndrome and associated connective tissue disorders.

30 Claims, 24 Drawing Sheets
Specification includes a Sequence Listing.

(56) References Cited

OTHER PUBLICATIONS

Habashi et al. (May 1, 2019) "Oxytocin Antagonism Prevents Pregnancy-associated Aortic Dissection in a Mouse Model of Marfan Syndrome", Science Translational Medicine, 11(490):20 pages.
Holm et al. (Apr. 15, 2011) "Noncanonical TGFB Signaling Contributes to Aortic Aneurysm Progression in Marfan Syndrome Mice", Science, 332(6027):9 Pages . . . .
Judge et al. (Jul. 2004) "Evidence for a Critical Contribution of Haploinsufficiency in the Complex Pathogenesis of Marfan Syndrome", The Journal of Clinical Investigation, 114(2):172-181.
Larkin et al. (Nov. 13, 2014) "Combined Vemurafenib and Cobimetinib in BRAF-mutated Melanoma", The New England Journal of Medicine, 371(20):1867-1876.
Lloyd et al. (Dec. 2006) "Effect of Ruboxistaurin on Visual Loss in Patients With Diabetic Retinopathy", Ophthalmology, 113(12):2221-2230.
Luo et al. (Jan. 2012) "Disease-associated Mutations Prevent GPR56-Collagen III Interaction", PLoS One, 7(1):e29818(7 pages).
Luo et al. (Jun. 2014) "Mechanism for Adhesion G Protein-coupled Receptor GPR56-mediated RhoA Activation Induced by Collagen III stimulation", PLoS One, 9(6):e100043(9 pages).
Manning et al. (Apr. 2012) "Oxytocin and Vasopressin Agonists and Antagonists as Research Tools and Potential Therapeutics", Journal of Neuroendocrinology, 24(4):609-628.
Ong et al. (Oct. 30, 2010) "Effect of Celiprolol on Prevention of Cardiovascular Events in Vascular Ehlers-danlos Syndrome: A Prospective Randomised, Open, Blinded-endpoints Trial", The Lancet, 376(9751):1476-1484.
Pepin et al. (Mar. 9, 2000) "Clinical and Genetic Features of Ehlers-danlos Syndrome Type IV, The Vascular Type", The New England Journal of Medicine, 342(10):673-680.
Pepin et al. (Dec. 2014) "Survival is Affected by Mutation Type and Molecular Mechanism in Vascular Ehlers-danlos Syndrome (EDS type IV)", Genetics in Medicine, 16(12):881-888.
Shalhub et al. (Jul. 2014) "Molecular Diagnosis in Vascular Ehlers-danlos Syndrome Predicts Pattern of Arterial Involvement and Outcomes", Journal of Vascular Surgery, 60(1):160-169.
Zaenglein Andrea L. (Oct. 4, 2018) "Acne Vulgaris", The New England Journal of Medicine, 379 (14):1343-1352.
Beridze and Frishman, "Vascular Ehlers-Danlos Syndrome: Pathophysiology, Diagnosis, and Prevention and Treatment of Its Complications," Cardiology in Review, 20(1), pp. 4-7 (2011).
European Supplementary Search Report completed on Jun. 21, 2022 in EP 19872573.
Bade et al., "Endovascular Abdominal Aortic Aneurysm Repoair in a Patient with Ehlers-Danlos Syndrome," Journal of Vascular Surgery, 46:2 pp. 360-362, 2007.
Sharp, et al., "Protein Kinase C Inhibition with Ruboxistaurin Increases Contractility and Reduces Heart Size in a Swine Model of Heart Failure with Reduced Ejection Fraction," JACC, Basic to Translational Science. 2:6, pp. 669-683, 2017.
Leppanen et al., "Protein Kinases C and its Inhibitors in the Regulation of Inflammation: Inducible Nitric Oxide Synthase as an Example," Basic and Clinical Pharmacology and Toxicology. vol. 114, pp. 37-43, 2014.
He et al., "Targeting PKC in Human T Cells Using Sotrastaurin (AEB071) Preserves Regulatory T. Cells and Prevents IL-17 Production, " Journal of Investigative Dermatology, vol. 134, pp. 975-983, 2014.
Lin et al., "Genetic Variants in PLCB4/PLCb1 as Susceptibility Loci For Coronary Artery Aneurysm Formation in Kawasaki Disease in Han Chinese in Taiwan," Scientific Reports, vol. 5, pp. 1-12, 2015.
International Search Report and the Written Opinion from PCT Application No. PCT/US2019/056616 dated Apr. 9, 2020, 13 pages.
ELife, 2015, vol. 4, Article.e08648 (p. 1-18), DOI: 10.7554/eLife.08648.
Journal of clinical and experimental medicine (Igaku no ayumi), Jan. 20, 2018, vol. 264 No. 3, p. 211-215.
Journal of clinical and experimental medicine (Igaku no ayumi), Jan. 20, 2018, vol. 264 No. 3, p. 227-233.
Cardiol Rev, 2012, vol. 20 No. 1, p. 4-7, doi: 10.1097/CRD.0b013e3182342316.
Doyle Jefferson Jet al: "A deleterious gene-by-environment interaction imposed by calcium channel blockers in Marfan syndrome"ELIFE, vol. 4, Oct. 27, 2015 (Oct. 27, 2015), pp. 1-18.
Beridze Natalia et al: "Vascular Ehlers-Danlos syndrome: pathophysiology, diagnosis, and prevention and treatment of its complications", Cardiology in Review, Lippincott Williams & Wilkins, US, vol. 20, No. 1, Dec. 31, 2011 (Dec. 31, 2011), pp. 4-7.
Office Action dated Sep. 4, 2023 in Japanese Patent Application No. 2021-520923.
Extended European Search Report dated Jun. 29, 2022 in European Patent Application No. 19872573.1.
Extended European Search Report dated Dec. 1, 2023 in European Patent Application No. 23191111.6 and claims of European Patent Application No. 23191111.6.
Jost Cha et al.: "Medical treatment of aortic aneurysms in Marfan syndrome and other heritable conditions"; Curr Cardiol Rev, vol. 10, No. 2, pp. 161-171, DOI: 10.2174/1573403x1002140506124902, May 31, 2014 (May 31, 2014).
Office Action dated Nov. 2, 2023 in Israeli Patent Application No. 281623.

* cited by examiner

| Upstream Regulator | Description | p-value of overlap |
|---|---|---|
| APOE | transporter | 3.47E-12 |
| NFATC3 | Transcription regulator activated by $Ca^{2+}$ | 8.70E-11 |
| F2R | GPCR | 8.70E-08 |
| ELK3 | Transcription regulator activated by ERK | 5.41E-08 |
| Mt2 | GPCR | 1.45E-07 |
| Mt1 | GPCR | 1.79E-07 |
| LIPE | enzyme | 3.09E-07 |
| ELK4 | Transcription regulator activated by ERK | 4.71E-07 |
| AFP | transporter | 4.71E-07 |
| ERK1/2 | group | 5.92E-07 |

FIG. 1G
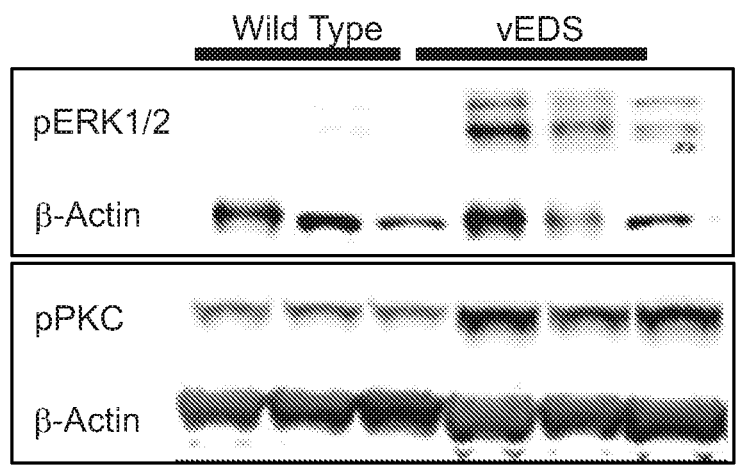
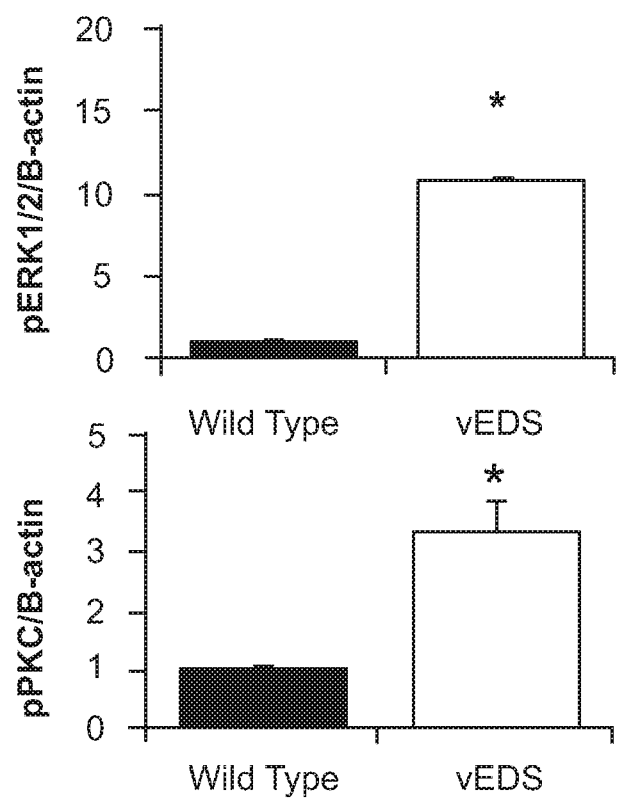

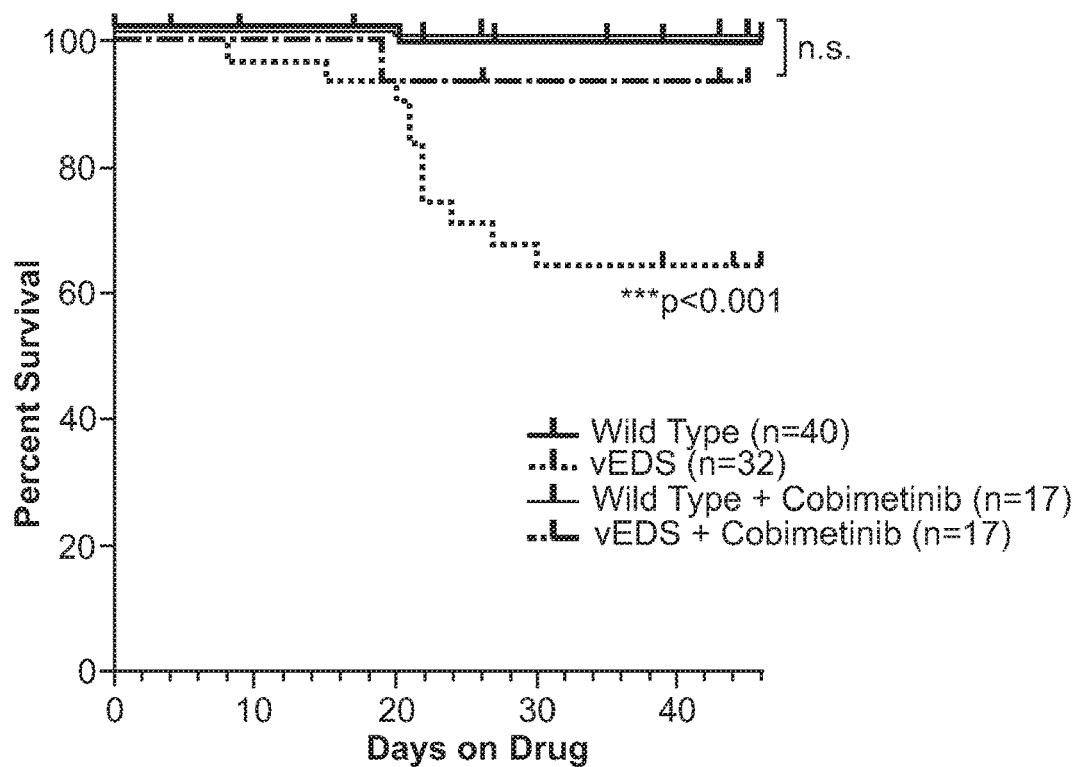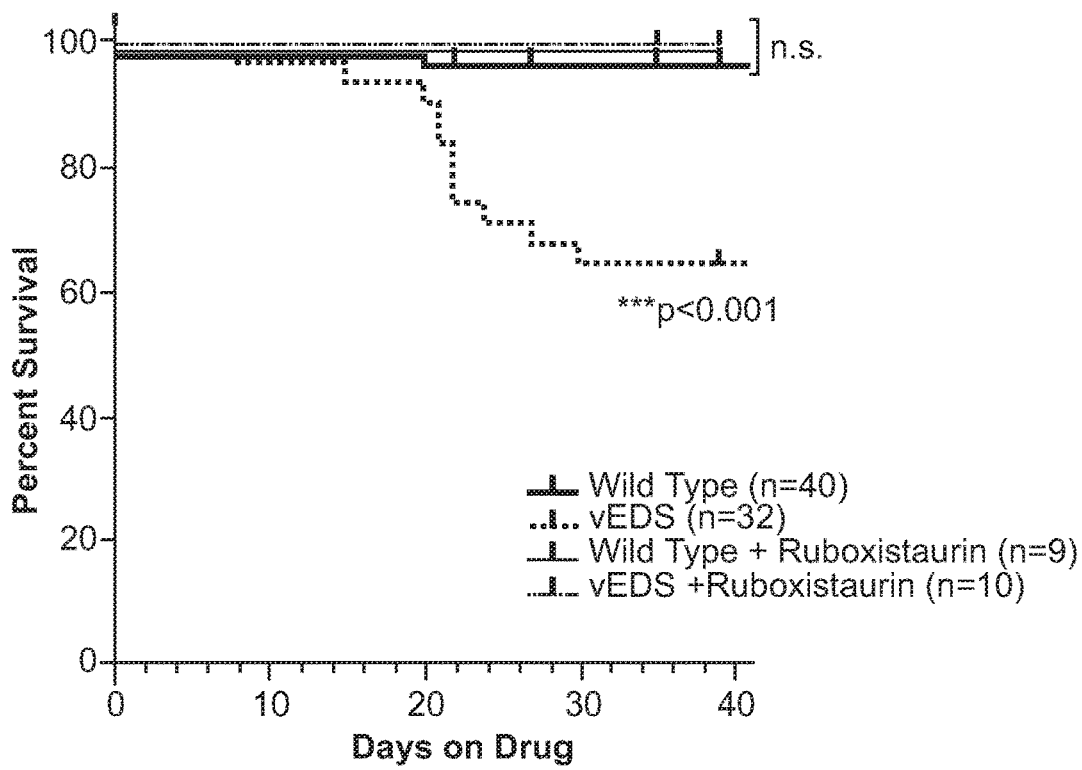

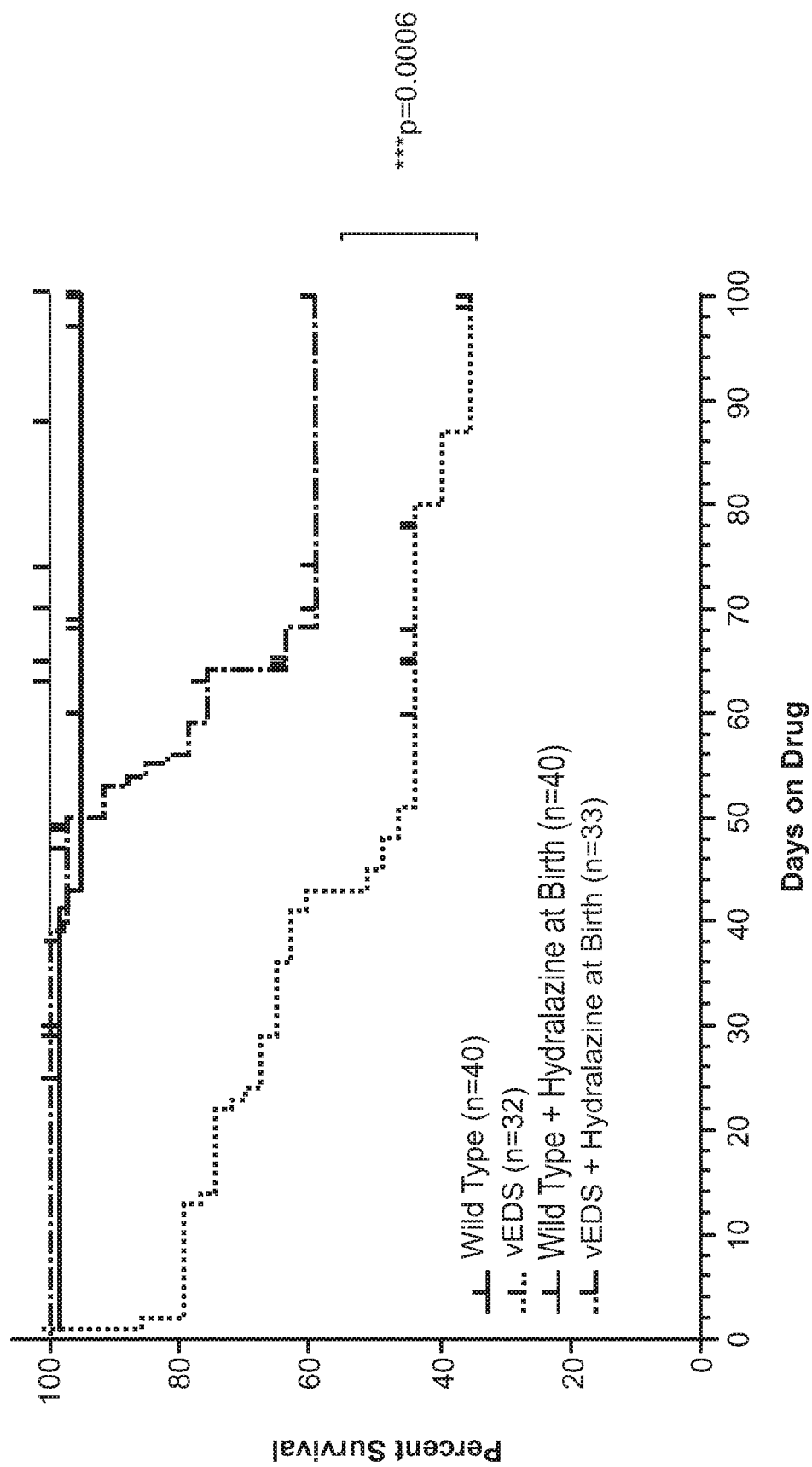

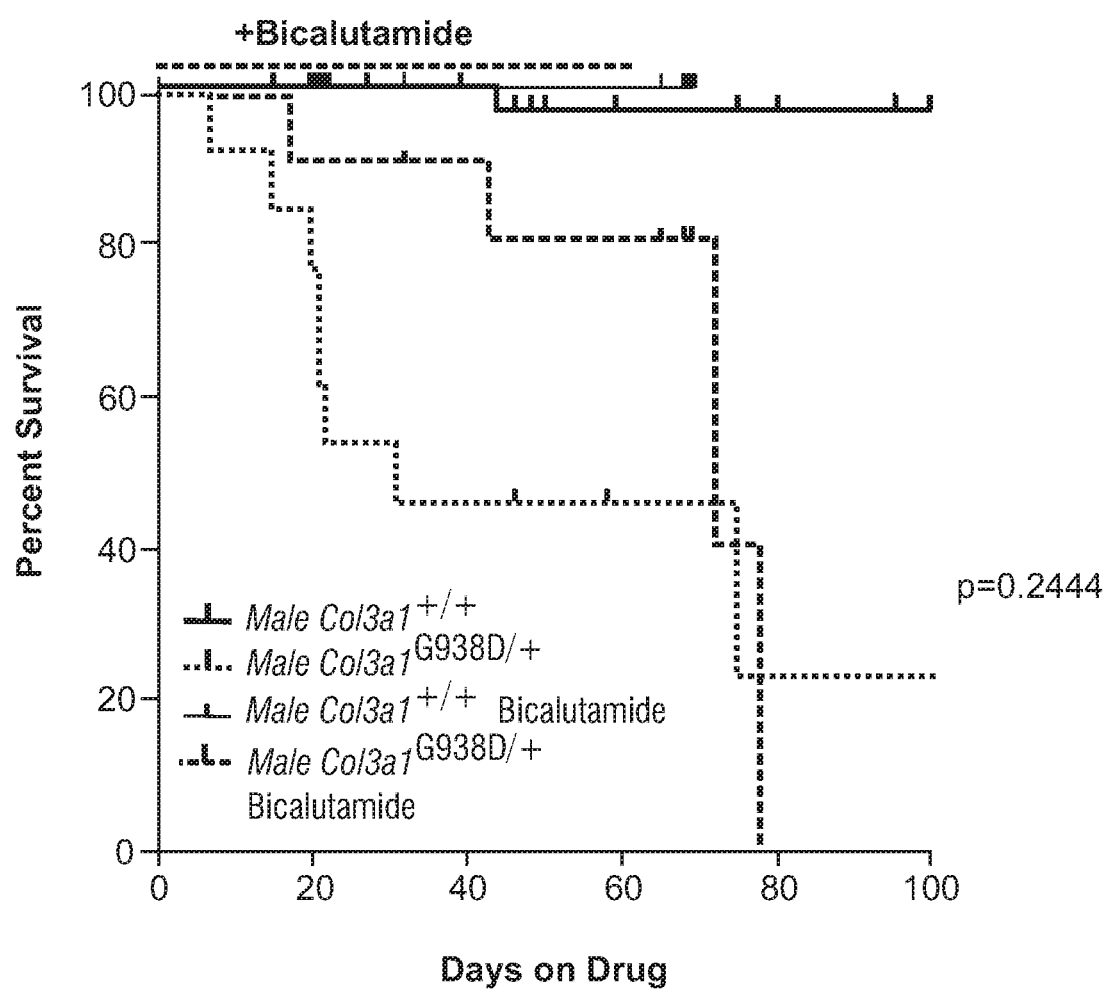

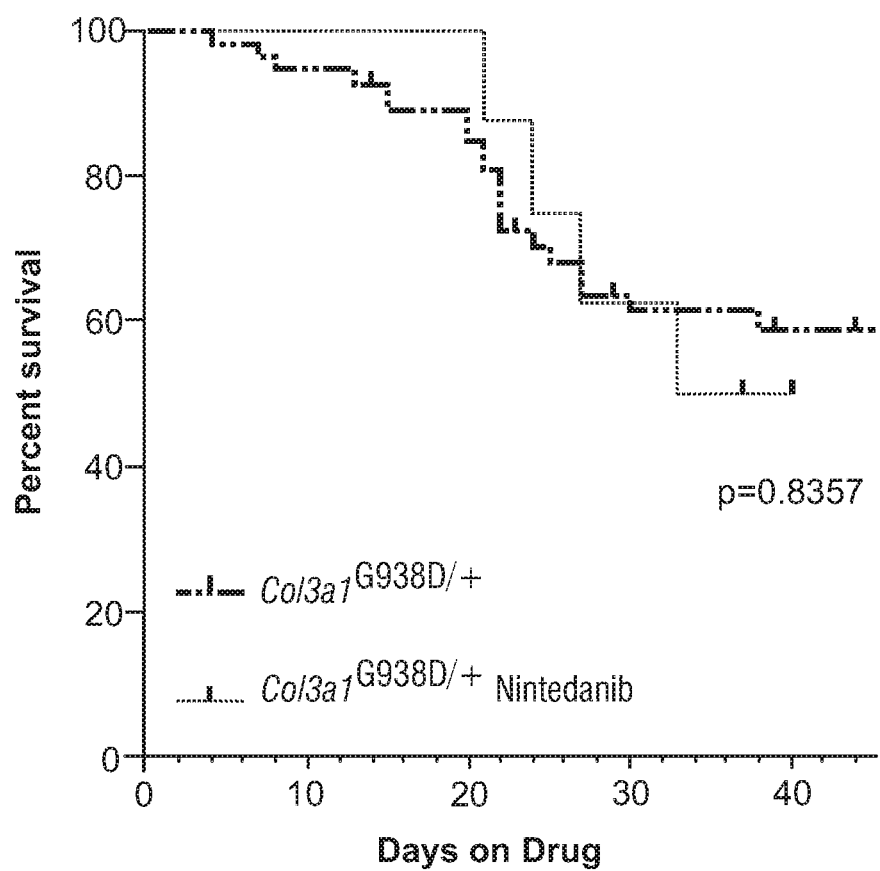

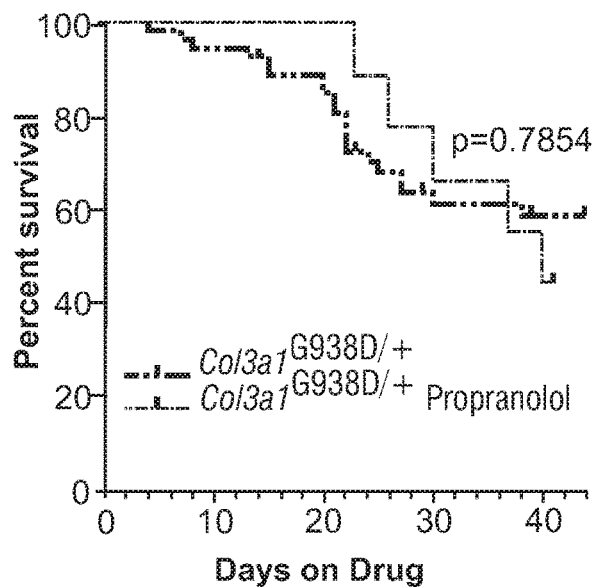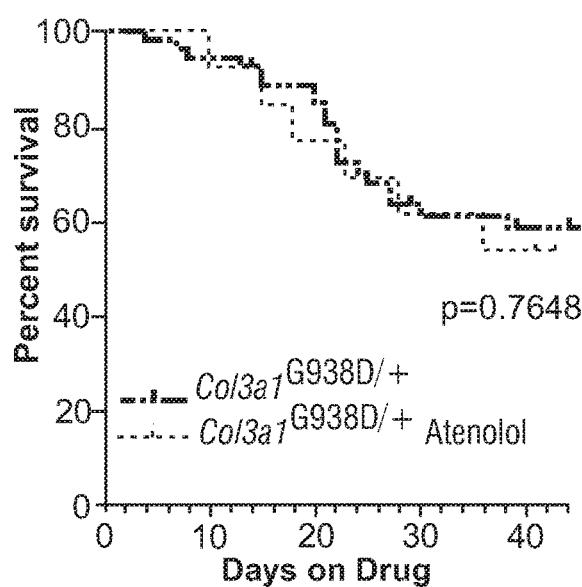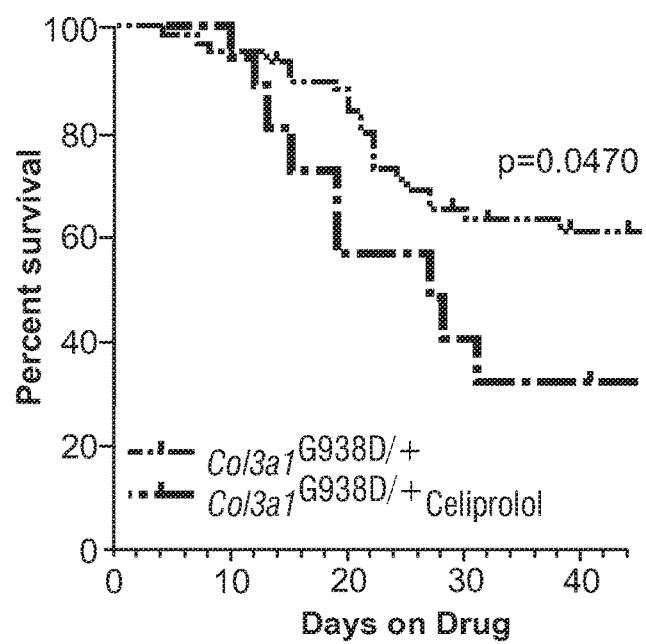

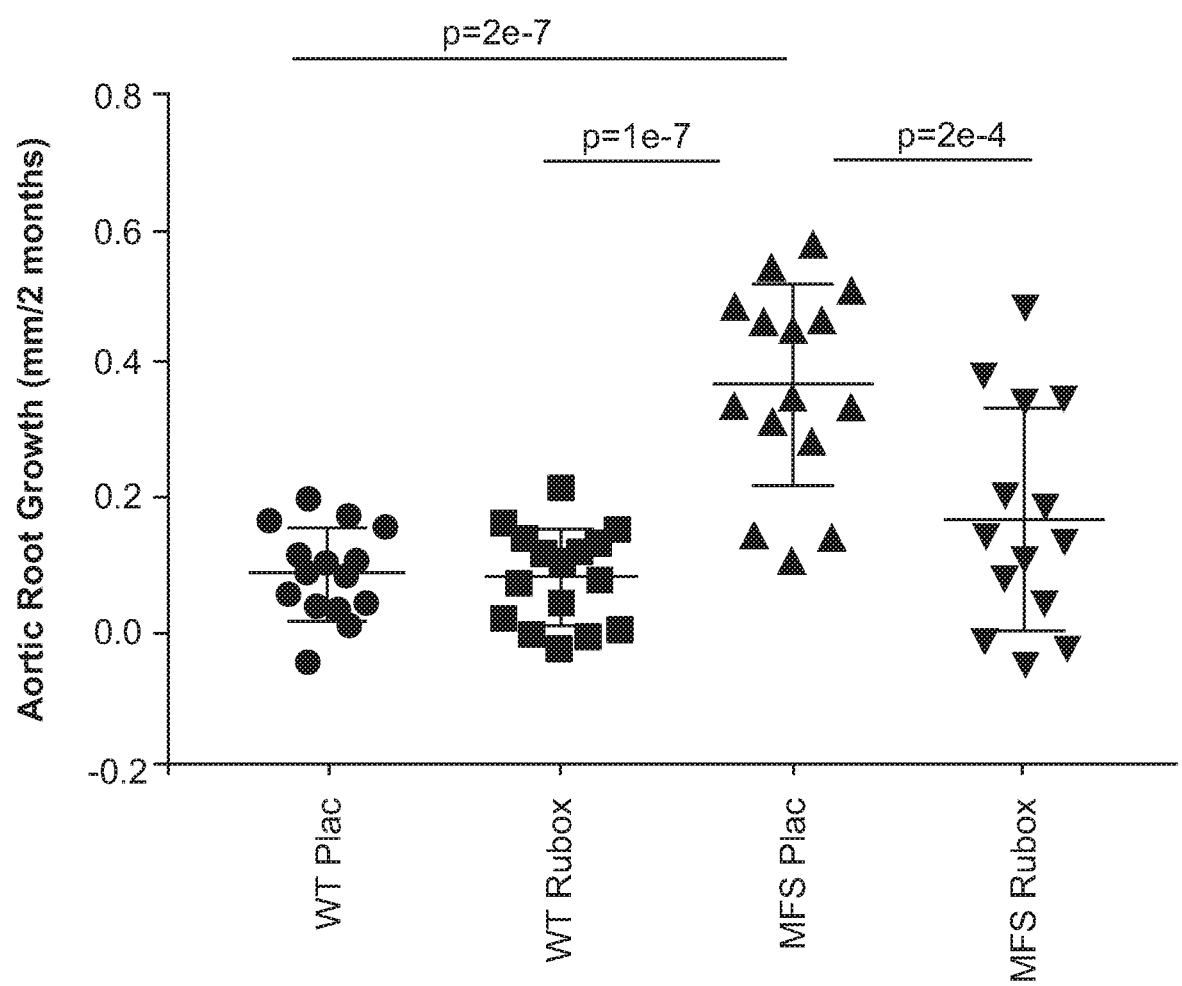

SEQUENCE LISTING

```
<160> NUMBER OF SEQ ID NOS: 8

<210> SEQ ID NO 1
<211> LENGTH: 1163
<212> TYPE: PRT
<213> ORGANISM: Homo sapiens

<400> SEQUENCE: 1

Met Met Ser Phe Val Gln Lys Gly Ser Trp Leu Leu Leu Ala Leu Leu
1               5                   10                  15

His Pro Thr Ile Ile Leu Ala Gln Gln Glu Ala Val Glu Gly Gly Cys
            20                  25                  30

Ser His Leu Gly Gln Ser Tyr Ala Asp Arg Asp Val Trp Lys Pro Glu
        35                  40                  45

Pro Cys Gln Ile Cys Val Cys Asp Ser Gly Ser Val Leu Cys Asp Asp
    50                  55                  60

Ile Ile Cys Asp Asp Gln Glu Leu Asp Cys Pro Asn Pro Glu Ile Pro
65                  70                  75                  80

Phe Gly Glu Cys Cys Ala Val Cys Pro Gln Pro Pro Thr Ala Pro Thr
                85                  90                  95

Arg Pro Pro Asn Gly Gln Gly Pro Gln Gly Pro Lys Gly Asp Pro Gly
            100                 105                 110

Pro Pro Gly Ile Pro Gly Arg Asn Gly Asp Pro Gly Ile Pro Gly Gln
        115                 120                 125

Pro Gly Ser Pro Gly Ser Pro Gly Pro Pro Gly Ile Cys Glu Ser Cys
```

```
               130                 135                 140
Pro Thr Gly Pro Gln Asn Tyr Ser Pro Gln Tyr Asp Ser Tyr Asp Val
145                 150                 155                 160

Lys Ser Gly Val Ala Val Gly Leu Ala Gly Tyr Pro Gly Pro Ala
                165                 170                 175

Gly Pro Pro Gly Pro Gly Pro Pro Gly Thr Ser Gly His Pro Gly
                180                 185                 190

Ser Pro Gly Ser Pro Gly Tyr Gln Gly Pro Pro Gly Glu Pro Gly Gln
                195                 200                 205

Ala Gly Pro Ser Gly Pro Pro Gly Pro Pro Gly Ala Ile Gly Pro Ser
        210                 215                 220

Gly Pro Ala Gly Lys Asp Gly Glu Ser Gly Arg Pro Gly Arg Pro Gly
225                 230                 235                 240

Glu Arg Gly Leu Pro Gly Pro Pro Gly Ile Lys Gly Pro Ala Gly Ile
                245                 250                 255

Pro Gly Phe Pro Gly Met Lys Gly His Arg Gly Phe Asp Gly Arg Asn
                260                 265                 270

Gly Glu Lys Gly Glu Thr Gly Ala Pro Gly Leu Lys Gly Glu Asn Gly
            275                 280                 285

Leu Pro Gly Glu Asn Gly Ala Pro Gly Pro Met Gly Pro Arg Gly Ala
        290                 295                 300

Pro Gly Glu Arg Gly Arg Pro Gly Leu Pro Gly Ala Ala Gly Ala Arg
305                 310                 315                 320

Gly Asn Asp Gly Ala Arg Gly Ser Asp Gly Gln Pro Gly Pro Pro Gly
                325                 330                 335

Pro Pro Gly Thr Ala Gly Phe Pro Gly Ser Pro Gly Ala Lys Gly Glu
                340                 345                 350

Val Gly Pro Ala Gly Ser Pro Gly Ser Asn Gly Ala Pro Gly Gln Arg
                355                 360                 365

Gly Glu Pro Gly Pro Gln Gly His Ala Gly Ala Gln Gly Pro Pro Gly
                370                 375                 380

Pro Pro Gly Ile Asn Gly Ser Pro Gly Gly Lys Gly Glu Met Gly Pro
385                 390                 395                 400

Ala Gly Ile Pro Gly Ala Pro Gly Leu Met Gly Ala Arg Gly Pro Pro
                405                 410                 415

Gly Pro Ala Gly Ala Asn Gly Ala Pro Gly Leu Arg Gly Gly Ala Gly
                420                 425                 430

Glu Pro Gly Lys Asn Gly Ala Lys Gly Glu Pro Gly Pro Arg Gly Glu
                435                 440                 445

Arg Gly Glu Ala Gly Ile Pro Gly Val Pro Gly Ala Lys Gly Glu Asp
450                 455                 460

Gly Lys Asp Gly Ser Pro Gly Glu Pro Gly Ala Asn Gly Leu Pro Gly
465                 470                 475                 480

Ala Ala Gly Glu Arg Gly Ala Pro Gly Phe Arg Gly Pro Ala Gly Pro
                485                 490                 495

Asn Gly Ile Pro Gly Glu Lys Gly Pro Ala Gly Glu Arg Gly Ala Pro
                500                 505                 510

Gly Pro Ala Gly Pro Arg Gly Ala Ala Gly Glu Pro Gly Arg Asp Gly
                515                 520                 525

Val Pro Gly Gly Pro Gly Met Arg Gly Met Pro Gly Ser Pro Gly Gly
                530                 535                 540

Pro Gly Ser Asp Gly Lys Pro Gly Pro Pro Gly Ser Gln Gly Glu Ser
545                 550                 555                 560
```

```
Gly Arg Pro Gly Pro Gly Pro Ser Gly Pro Arg Gly Gln Pro Gly
            565                 570                 575

Val Met Gly Phe Pro Gly Pro Lys Gly Asn Asp Gly Ala Pro Gly Lys
            580                 585                 590

Asn Gly Glu Arg Gly Gly Pro Gly Gly Pro Gly Pro Gln Gly Pro Pro
            595                 600                 605

Gly Lys Asn Gly Glu Thr Gly Pro Gln Gly Pro Pro Gly Pro Thr Gly
            610                 615                 620

Pro Gly Gly Asp Lys Gly Asp Thr Gly Pro Pro Gly Pro Gln Gly Leu
625                 630                 635                 640

Gln Gly Leu Pro Gly Thr Gly Gly Pro Pro Gly Glu Asn Gly Lys Pro
            645                 650                 655

Gly Glu Pro Gly Pro Lys Gly Asp Ala Gly Ala Pro Gly Ala Pro Gly
            660                 665                 670

Gly Lys Gly Asp Ala Gly Ala Pro Gly Glu Arg Gly Pro Pro Gly Leu
            675                 680                 685

Ala Gly Ala Pro Gly Leu Arg Gly Gly Ala Gly Pro Pro Gly Pro Glu
            690                 695                 700

Gly Gly Lys Gly Ala Ala Gly Pro Pro Gly Pro Pro Gly Ala Ala Gly
705                 710                 715                 720

Thr Pro Gly Leu Gln Gly Met Pro Gly Glu Arg Gly Gly Leu Gly Ser
            725                 730                 735

Pro Gly Pro Lys Gly Asp Lys Gly Glu Pro Gly Gly Pro Gly Ala Asp
            740                 745                 750

Gly Val Pro Gly Lys Asp Gly Pro Arg Gly Pro Thr Gly Pro Ile Gly
            755                 760                 765

Pro Pro Gly Pro Ala Gly Gln Pro Gly Asp Lys Gly Glu Gly Gly Ala
770                 775                 780

Pro Gly Leu Pro Gly Ile Ala Gly Pro Arg Gly Ser Pro Gly Glu Arg
785                 790                 795                 800

Gly Glu Thr Gly Pro Pro Gly Pro Ala Gly Phe Pro Gly Ala Pro Gly
            805                 810                 815

Gln Asn Gly Glu Pro Gly Gly Lys Gly Glu Arg Gly Ala Pro Gly Glu
            820                 825                 830

Lys Gly Glu Gly Gly Pro Pro Gly Val Ala Gly Pro Pro Gly Lys Asp
            835                 840                 845

Gly Thr Ser Gly His Pro Gly Pro Ile Gly Pro Pro Gly Pro Arg Gly
            850                 855                 860

Asn Arg Gly Glu Arg Gly Ser Glu Gly Ser Pro Gly His Pro Gly Gln
865                 870                 875                 880

Pro Gly Pro Pro Gly Pro Pro Gly Ala Pro Gly Pro Cys Cys Gly Gly
            885                 890                 895

Val Gly Ala Ala Ala Ile Ala Gly Ile Gly Gly Glu Lys Ala Gly Gly
            900                 905                 910

Phe Ala Pro Tyr Tyr Gly Asp Glu Pro Met Asp Phe Lys Ile Asn Thr
            915                 920                 925

Asp Glu Ile Met Thr Ser Leu Lys Ser Val Asn Gly Gln Ile Glu Ser
            930                 935                 940

Leu Ile Ser Pro Asp Gly Ser Arg Lys Asn Pro Ala Arg Asn Cys Arg
945                 950                 955                 960

Asp Leu Lys Phe Cys His Pro Glu Leu Lys Ser Gly Glu Tyr Trp Val
            965                 970                 975
```

-continued

| | | | | | | | | | | | | |
|---|---|---|---|---|---|---|---|---|---|---|---|---|
|Asp|Pro|Asn|Gln|Gly|Cys|Lys|Leu|Asp|Ala|Ile|Lys|Val|Phe|Cys|Asn|
| | |980| | | |985| | | |990| | | | | |
|Met|Glu|Thr|Gly|Glu|Thr|Cys|Ile|Ser|Ala|Asn|Pro|Leu|Asn|Val|Pro|
| |995| | | | |1000| | | | |1005| | | | |
|Arg|Lys|His|Trp|Trp|Thr|Asp|Ser|Ser|Ala|Glu|Lys|Lys|His|Val|
| |1010| | | | |1015| | | |1020| | | | |
|Trp|Phe|Gly|Glu|Ser|Met|Asp|Gly|Gly|Phe|Gln|Phe|Ser|Tyr|Gly|
| |1025| | | | |1030| | | |1035| | | | |
|Asn|Pro|Glu|Leu|Pro|Glu|Asp|Val|Leu|Asp|Val|Gln|Leu|Ala|Phe|
| |1040| | | | |1045| | | |1050| | | | |
|Leu|Arg|Leu|Leu|Ser|Ser|Arg|Ala|Ser|Gln|Asn|Ile|Thr|Tyr|His|
| |1055| | | | |1060| | | |1065| | | | |
|Cys|Lys|Asn|Ser|Ile|Ala|Tyr|Met|Asp|Gln|Ala|Ser|Gly|Asn|Val|
| |1070| | | | |1075| | | |1080| | | | |
|Lys|Lys|Ala|Leu|Lys|Leu|Met|Gly|Ser|Asn|Glu|Gly|Glu|Phe|Lys|
| |1085| | | | |1090| | | |1095| | | | |
|Ala|Glu|Gly|Asn|Ser|Lys|Phe|Thr|Tyr|Thr|Val|Leu|Glu|Asp|Gly|
| |1100| | | | |1105| | | |1110| | | | |
|Cys|Thr|Lys|His|Thr|Gly|Glu|Trp|Ser|Lys|Thr|Val|Phe|Glu|Tyr|
| |1115| | | | |1120| | | |1125| | | | |
|Arg|Thr|Arg|Lys|Ala|Val|Arg|Leu|Pro|Ile|Val|Asp|Ile|Ala|Pro|
| |1130| | | | |1135| | | |1140| | | | |
|Tyr|Asp|Ile|Gly|Gly|Pro|Asp|Gln|Glu|Phe|Gly|Val|Asp|Val|Gly|
| |1145| | | | |1150| | | |1155| | | | |
|Pro|Val|Cys|Phe|Leu|
| |1160| | | |

<210> SEQ ID NO 2
<211> LENGTH: 5490
<212> TYPE: DNA
<213> ORGANISM: Homo sapiens

<400> SEQUENCE: 2

```
ggctgagttt tatgacgggc ccggtgctga agggcaggga acaacttgat ggtgctactt      60
tgaactgctt ttcttttctc cttttgcac aaagagtctc atgtctgata tttagacatg      120
atgagctttg tgcaaaaggg gagctggcta cttctcgctc tgcttcatcc cactattatt      180
ttggcacaac aggaagctgt tgaaggagga tgttcccatc ttggtcagtc ctatgcggat      240
agagatgtct ggaagccaga accatgccaa atatgtgtct gtgactcagg atccgttctc      300
tgcgatgaca taatatgtga cgatcaagaa ttagactgcc ccaacccaga aattccattt      360
ggagaatgtt gtgcagtttg cccacagcct ccaactgctc ctactcgccc tcctaatggt      420
caaggacctc aaggccccaa gggagatcca ggccctcctg gtattcctgg agaaatggt      480
gaccctggta ttccaggaca accagggtcc cctggttctc ctggcccccc tggaatctgt      540
gaatcatgcc ctactggtcc tcagaactat tctccccagt atgattcata tgatgtcaag      600
tctggagtag cagtaggagg actcgcaggc tatcctggac cagctggccc cccaggccct      660
cccggtcccc ctggtacatc tggtcatcct ggttcccctg gatctccagg ataccaagga      720
cccccctggtg aacctgggca agctggtcct tcaggccctc aggacctcc tggtgctata      780
ggtccatctg gtcctgctgg aaaagatgga gaatcaggta gacccggacg acctggagag      840
cgaggattgc ctggacctcc aggtatcaaa ggtccagctg gataccctgg attccctggt      900
atgaaaggac acagaggctt cgatggacga atggagaaa agggtgaaac aggtgctcct      960
```

```
ggattaaagg gtgaaaatgg tcttccaggc gaaaatggag ctcctggacc catgggtcca    1020 agagggctc ctggtgagcg aggacggcca ggacttcctg gggctgcagg tgctcggggt    1080
aatgacggtg ctcgaggcag tgatggtcaa ccaggccctc ctggtcctcc tggaactgcc    1140
ggattccctg gatcccctgg tgctaagggt gaagttggac ctgcagggtc tcctggttca    1200
aatggtgccc ctggacaaag aggagaacct ggacctcagg acacgctgg tgctcaaggt    1260 cctcctggcc ctcctgggat taatggtagt cctggtggta aaggcgaaat gggtcccgct    1320
ggcattcctg gagctcctgg actgatggga gcccggggtc ctccaggacc agccggtgct    1380
aatggtgctc ctggactgcg aggtggtgca ggtgagcctg gtaagaatgg tgccaaagga    1440
gagcccggac cacgtggtga acgcggtgag gctggtattc caggtgttcc aggagctaaa    1500
ggcgaagatg gcaaggatgg atcacctgga gaacctggtg caaatgggct tccaggagct    1560
gcaggagaaa ggggtgcccc tgggttccga ggacctgctg gaccaaatgg catcccagga    1620
gaaaagggtc ctgctggaga gcgtggtgct ccaggccctg cagggcccag aggagctgct    1680
ggagaacctg gcagagatgg cgtccctgga ggtccaggaa tgaggggcat gcccggaagt    1740
ccaggaggac caggaagtga tggaaaacca gggcctcccg gaagtcaagg agaaagtggt    1800
cgaccaggtc ctcctgggcc atctggtccc cgaggtcagc ctggtgtcat gggcttcccc    1860
ggtcctaaag gaaatgatgg tgctcctggt aagaatggag aacgaggtgg ccctggagga    1920
cctggccctc agggtcctcc tggaaagaat ggtgaaactg gacctcaggg accccagggg    1980
cctactgggc ctggtggtga caaaggagac acaggacccc ctggtccaca aggattacaa    2040
ggcttgcctg gtacaggtgg tcctccagga gaaaatggaa aacctgggga accaggtcca    2100
aagggtgatg ccggtgcacc tggagctcca ggaggcaagg gtgatgctgg tgcccctggt    2160
gaacgtggac ctcctggatt ggcaggggcc ccaggactta gggtggagc tggtcccccct    2220 ggtcccgaag gaggaaaggg tgctgctggt cctcctgggc cacctggtgc tgctggtact    2280
cctggtctgc aaggaatgcc tggagaaaga ggaggtcttg gaagtcctgg tccaaagggt    2340
gacaagggtg aaccaggcgg tccaggtgct gatggtgtcc cagggaaaga tggcccaagg    2400
ggtcctactg gtcctattgg tcctcctggc ccagctggcc agcctggaga taagggtgaa    2460
ggtggtgccc ccggacttcc aggtatagct ggacctcgtg gtagccctgg tgagagaggt    2520
gaaactggcc ctccaggacc tgctggttc cctggtgctc ctggacagaa tggtgaacct    2580
ggtggtaaag gagaaagagg ggctccgggt gagaaaggtg aaggaggccc tcctggagtt    2640
gcaggacccc ctgaggttc tggacctgct ggtcctcctg gtcccaagg tgtcaaaggt    2700 gaacgtggca gtcctggtgg acctggtgct gctggcttcc ctggtgctcg tggtcttcct    2760
ggtcctcctg gtagtaatgg taacccagga ccccaggtc ccagcggttc tccaggcaag    2820
gatgggcccc caggtcctgc gggtaacact ggtgctcctg gcagccctgg agtgtctgga    2880
ccaaaaggtg atgctggcca accaggagag aagggatcgc ctggtgccca gggcccacca    2940
ggagctccag gcccacttgg gattgctggg atcactggaa cacggggtct tgcaggacca    3000
ccaggcatgc caggtcctag gggaagccct ggccctcagg gtgtcaaggg tgaaagtggg    3060
aaaccaggag ctaacggtct cagtggagaa cgtggtcccc ctggaccca gggtcttcct    3120 ggtctggctg gtacagctgg tgaacctgga agagatggaa accctggatc agatggtctt    3180
ccaggccgag atggatctcc tggtggcaag ggtgatcgtg gtgaaaatgg ctctcctggt    3240 gccctggcg ctcctggtca tccaggccca cctggtcctg tcggtccagc tggaaagagt    3300
ggtgacagag gagaaagtgg ccctgctggc cctgctggtg ctcccggtcc tgctggttcc    3360
```

```
cgaggtgctc ctggtcctca aggcccacgt ggtgacaaag gtgaaacagg tgaacgtgga    3420
gctgctggca tcaaaggaca tcgaggattc cctggtaatc caggtgcccc aggttctcca    3480
ggccctgctg gtcagcaggg tgcaatcggc agtccaggac ctgcaggccc cagaggacct    3540
gttggaccca gtggacctcc tggcaaagat ggaaccagtg gacatccagg tcccattgga    3600
ccaccagggc ctcgaggtaa cagaggtgaa agaggatctg agggctcccc aggccaccca    3660
gggcaaccag gccctcctgg acctcctggt gcccctggtc cttgctgtgg tggtgttgga    3720
gccgctgcca ttgctgggat tggaggtgaa aaagctggcg ttttgcccc gtattatgga     3780 gatgaaccaa tggatttcaa aatcaacacc gatgagatta tgacttcact caagtctgtt    3840
aatggacaaa tagaaagcct cattagtcct gatggttctc gtaaaaaccc cgctagaaac    3900
tgcagagacc tgaaattctg ccatcctgaa ctcaagagtg gagaatactg ggttgaccct    3960
aaccaaggat gcaaattgga tgctatcaag gtattctgta atatggaaac tggggaaaca    4020
tgcataagtg ccaatccttt gaatgttcca cggaaacact ggtggacaga ttctagtgct    4080
gagaagaaac acgtttggtt tggagagtcc atggatggtg ttttcagtt tagctacggc    4140 aatcctgaac ttcctgaaga tgtccttgat gtgcagctgg cattccttcg acttctctcc    4200
agccgagctt cccagaacat cacatatcac tgcaaaaata gcattgcata catggatcag    4260
gccagtggaa atgtaaagaa ggccctgaag ctgatggggt caaatgaagg tgaattcaag    4320
gctgaaggaa atagcaaatt cacctacaca gttctggagg atggttgcac gaaacacact    4380
ggggaatgga gcaaaacagt ctttgaatat cgaacacgca aggctgtgag actacctatt    4440
gtagatattg caccctatga cattggtggt cctgatcaag aatttggtgt ggacgttggc    4500
cctgtttgct ttttataaac caaactctat ctgaaatccc aacaaaaaaa atttaactcc    4560
atatgtgttc ctcttgttct aatcttgtca accagtgcaa gtgaccgaca aaattccagt    4620
tatttatttc caaatgtttt ggaaacagta taatttgaca agaaaaatg atacttctct     4680 tttttttgctg ttccaccaaa tacaattcaa atgctttttg ttttatttt ttaccaattc    4740 caatttcaaa atgtctcaat ggtgctataa taaataaact tcaacactct ttatgataac    4800
aacactgtgt tatattcttt gaatcctagc ccatctgcag agcaatgact gtgctcacca    4860
gtaaaagata accttttcttt ctgaaatagt caaatacgaa attagaaaag ccctccctat    4920
tttaactacc tcaactggtc agaaacacag attgtattct atgagtccca gaagatgaaa    4980
aaaattttat acgttgataa aacttataaa tttcattgat taatctcctg gaagattggt    5040
ttaaaaagaa aagtgtaatg caagaattta agaaatatt tttaaagcca caattatttt     5100
aatattggat atcaactgct tgtaaaggtg ctcctctttt ttcttgtcat tgctggtcaa    5160
gattactaat atttgggaag gctttaaaga cgcatgttat ggtgctaatg tactttcact    5220
tttaaactct agatcagaat tgttgacttg cattcagaac ataaatgcac aaaatctgta    5280
catgtctccc atcagaaaga ttcattggca tgccacaggg gattcctctc cttcatcctg    5340
taaaggtcaa caataaaaac caaattatgg ggctgctttt gtcacactag catagagaat    5400
gtgttgaaat ttaactttgt aagcttgtat gtggttgttg atctttttt tccttacaga    5460 cacccataat aaaatatcat attaaaattc                                     5490

<210> SEQ ID NO 3
<211> LENGTH: 379
<212> TYPE: PRT
<213> ORGANISM: Homo sapiens
```

<400> SEQUENCE: 3

```
Met Ala Ala Ala Ala Gln Gly Gly Gly Gly Glu Pro Arg Arg
1               5                   10                  15

Thr Glu Gly Val Gly Pro Gly Val Pro Gly Glu Val Glu Met Val Lys
            20                  25                  30

Gly Gln Pro Phe Asp Val Gly Pro Arg Tyr Thr Gln Leu Gln Tyr Ile
        35                  40                  45

Gly Glu Gly Ala Tyr Gly Met Val Ser Ser Ala Tyr Asp His Val Arg
    50                  55                  60

Lys Thr Arg Val Ala Ile Lys Lys Ile Ser Pro Phe Glu His Gln Thr
65                  70                  75                  80

Tyr Cys Gln Arg Thr Leu Arg Glu Ile Gln Ile Leu Leu Arg Phe Arg
                85                  90                  95

His Glu Asn Val Ile Gly Ile Arg Asp Ile Leu Arg Ala Ser Thr Leu
            100                 105                 110

Glu Ala Met Arg Asp Val Tyr Ile Val Gln Asp Leu Met Glu Thr Asp
        115                 120                 125

Leu Tyr Lys Leu Leu Lys Ser Gln Gln Leu Ser Asn Asp His Ile Cys
130                 135                 140

Tyr Phe Leu Tyr Gln Ile Leu Arg Gly Leu Lys Tyr Ile His Ser Ala
145                 150                 155                 160

Asn Val Leu His Arg Asp Leu Lys Pro Ser Asn Leu Leu Ile Asn Thr
                165                 170                 175

Thr Cys Asp Leu Lys Ile Cys Asp Phe Gly Leu Ala Arg Ile Ala Asp
            180                 185                 190

Pro Glu His Asp His Thr Gly Phe Leu Thr Glu Tyr Val Ala Thr Arg
        195                 200                 205

Trp Tyr Arg Ala Pro Glu Ile Met Leu Asn Ser Lys Gly Tyr Thr Lys
210                 215                 220

Ser Ile Asp Ile Trp Ser Val Gly Cys Ile Leu Ala Glu Met Leu Ser
225                 230                 235                 240

Asn Arg Pro Ile Phe Pro Gly Lys His Tyr Leu Asp Gln Leu Asn His
                245                 250                 255

Ile Leu Gly Ile Leu Gly Ser Pro Ser Gln Glu Asp Leu Asn Cys Ile
            260                 265                 270

Ile Asn Met Lys Ala Arg Asn Tyr Leu Gln Ser Leu Pro Ser Lys Thr
        275                 280                 285

Lys Val Ala Trp Ala Lys Leu Phe Pro Lys Ser Asp Ser Lys Ala Leu
290                 295                 300

Asp Leu Leu Asp Arg Met Leu Thr Phe Asn Pro Asn Lys Arg Ile Thr
305                 310                 315                 320

Val Glu Glu Ala Leu Ala His Pro Tyr Leu Glu Gln Tyr Tyr Asp Pro
                325                 330                 335

Thr Asp Glu Pro Val Ala Glu Glu Pro Phe Thr Phe Ala Met Glu Leu
            340                 345                 350

Asp Asp Leu Pro Lys Glu Arg Leu Lys Glu Leu Ile Phe Gln Glu Thr
        355                 360                 365

Ala Arg Phe Gln Pro Gly Val Leu Glu Ala Pro
370                 375
```

<210> SEQ ID NO 4
<211> LENGTH: 1866
<212> TYPE: DNA
<213> ORGANISM: Homo sapiens

<400> SEQUENCE: 4

```
cgttcctcgg cgccgccggg gccccagagg gcagcggcag caacagcagc agcagcagca      60
gcgggagtgg agatggcggc ggcggcggct caggggggcg ggggcgggga gccccgtaga     120
accgaggggg tcggcccggg ggtcccgggg gaggtggaga tggtgaaggg gcagccgttc     180
gacgtgggcc cgcgctacac gcagttgcag tacatcggcg agggcgcgta cggcatggtc     240
agctcggcct atgaccacgt gcgcaagact cgcgtggcca tcaagaagat cagccccttc     300
gaacatcaga cctactgcca gcgcacgctc cgggagatcc agatcctgct gcgcttccgc     360
catgagaatg tcatcggcat ccgagacatt ctgcgggcgt ccaccctgga agccatgaga     420
gatgtctaca ttgtgcagga cctgatggag actgacctgt acaagttgct gaaaagccag     480
cagctgagca atgaccatat ctgctacttc ctctaccaga tcctgcgggg cctcaagtac     540
atccactccg ccaacgtgct ccaccgagat ctaaagccct ccaacctgct cagcaacacc     600
acctgcgacc ttaagatttg tgatttcggc ctggcccgga ttgccgatcc tgagcatgac     660
cacaccggct tcctgacgga gtatgtggct acgcgctggt accgggcccc agagatcatg     720
ctgaactcca agggctatac caagtccatc gacatctggt ctgtgggctg cattctggct     780
gagatgctct ctaaccggcc catcttccct ggcaagcact acctggatca gctcaaccac     840
attctgggca tcctgggctc cccatcccag gaggacctga attgtatcat caacatgaag     900
gcccgaaact acctacagtc tctgccctcc aagaccaagg tggcttgggc caagcttttc     960
cccaagtcag actccaaagc ccttgacctg ctggaccgga tgttaacctt taaccccaat    1020
aaacggatca cagtggagga agcgctggct caccctacc tggagcagta ctatgacccg    1080
acggatgagc cagtggccga ggagcccttc accttcgcca tggagctgga tgacctacct    1140
aaggagcggc tgaaggagct catcttccag gagacagcac gcttccagcc cggagtgctg    1200
gaggcccct agcccagaca gacatctctg caccctgggg cctggacctg cctcctgcct    1260
gccctctcc cgccagactg ttagaaaatg gacactgtgc ccagcccgga ccttggcagc    1320
ccaggccggg gtggagcatg ggcctggcca cctctctcct ttgctgaggc ctccagcttc    1380
aggcaggcca aggccttctc ctccccaccc gccctcccca cggggcctcg ggagctcagg    1440
tggccccagt tcaatctccc gctgctgctg ctgctgcgcc cttaccttcc ccagcgtccc    1500
agtctctggc agttctggaa tggaagggtt ctggctgccc caacctgctg aagggcagag    1560
gtggagggtg gggggcgctg agtagggact cagggccatg cctgccccc tcatctcatt    1620
caaaccccac cctagtttcc ctgaaggaac attccttagt ctcaagggct agcatccctg    1680
aggagccagg ccgggccgaa tcccctccct gtcaaagctg tcacttcgcg tgccctcgct    1740
gcttctgtgt gtggtgagca gaagtggagc tgggggcgt ggagagcccg cgcccctgc     1800
cacctcccctg acccgtctaa tatataaata tagagatgtg tctatggctg aaaaaaaaaa    1860
aaaaaa                                                                1866
```

<210> SEQ ID NO 5
<211> LENGTH: 360
<212> TYPE: PRT
<213> ORGANISM: Homo sapiens

<400> SEQUENCE: 5

```
Met Ala Ala Ala Ala Ala Gly Ala Gly Pro Glu Met Val Arg Gly
1               5                   10                  15

Gln Val Phe Asp Val Gly Pro Arg Tyr Thr Asn Leu Ser Tyr Ile Gly
```

```
            20                  25                  30
Glu Gly Ala Tyr Gly Met Val Cys Ser Ala Tyr Asp Asn Val Asn Lys
         35                  40                  45
Val Arg Val Ala Ile Lys Lys Ile Ser Pro Phe Glu His Gln Thr Tyr
     50                  55                  60
Cys Gln Arg Thr Leu Arg Glu Ile Lys Ile Leu Leu Arg Phe Arg His
 65                  70                  75                  80
Glu Asn Ile Ile Gly Ile Asn Asp Ile Ile Arg Ala Pro Thr Ile Glu
                 85                  90                  95
Gln Met Lys Asp Val Tyr Ile Val Gln Asp Leu Met Glu Thr Asp Leu
            100                 105                 110
Tyr Lys Leu Leu Lys Thr Gln His Leu Ser Asn Asp His Ile Cys Tyr
         115                 120                 125
Phe Leu Tyr Gln Ile Leu Arg Gly Leu Lys Tyr Ile His Ser Ala Asn
     130                 135                 140
Val Leu His Arg Asp Leu Lys Pro Ser Asn Leu Leu Asn Thr Thr
145                 150                 155                 160
Cys Asp Leu Lys Ile Cys Asp Phe Gly Leu Ala Arg Val Ala Asp Pro
                 165                 170                 175
Asp His Asp His Thr Gly Phe Leu Thr Glu Tyr Val Ala Thr Arg Trp
            180                 185                 190
Tyr Arg Ala Pro Glu Ile Met Leu Asn Ser Lys Gly Tyr Thr Lys Ser
         195                 200                 205
Ile Asp Ile Trp Ser Val Gly Cys Ile Leu Ala Glu Met Leu Ser Asn
     210                 215                 220
Arg Pro Ile Phe Pro Gly Lys His Tyr Leu Asp Gln Leu Asn His Ile
225                 230                 235                 240
Leu Gly Ile Leu Gly Ser Pro Ser Gln Glu Asp Leu Asn Cys Ile Ile
                 245                 250                 255
Asn Leu Lys Ala Arg Asn Tyr Leu Leu Ser Leu Pro His Lys Asn Lys
            260                 265                 270
Val Pro Trp Asn Arg Leu Phe Pro Asn Ala Asp Ser Lys Ala Leu Asp
         275                 280                 285
Leu Leu Asp Lys Met Leu Thr Phe Asn Pro His Lys Arg Ile Glu Val
     290                 295                 300
Glu Gln Ala Leu Ala His Pro Tyr Leu Glu Gln Tyr Tyr Asp Pro Ser
305                 310                 315                 320
Asp Glu Pro Ile Ala Glu Ala Pro Phe Lys Phe Asp Met Glu Leu Asp
                 325                 330                 335
Asp Leu Pro Lys Glu Lys Leu Lys Glu Leu Ile Phe Glu Glu Thr Ala
            340                 345                 350
Arg Phe Gln Pro Gly Tyr Arg Ser
         355                 360

<210> SEQ ID NO 6
<211> LENGTH: 1514
<212> TYPE: DNA
<213> ORGANISM: Homo sapiens

<400> SEQUENCE: 6
gcccctccct ccgcccgccc gccggccggc ccgtcagtct ggcaggcagg caggcaatcg      60
gtccgagtgg ctgtcggctc ttcagctctc ccgtcggcg tcttccttcc tcctcccggt     120
cagcgtcggc ggctgcaccg gcggcggcgc agtccctgcg ggaggggcga caagagctga    180
```

| | |
|---|---:|
| gcggcggccg ccgagcgtcg agctcagcgc ggcggaggcg gcggcggccc ggcagccaac | 240 |
| atggcggcgg cggcggcggc gggcgcgggc ccggagatgg tccgcgggca ggtgttcgac | 300 |
| gtggggccgc gctacaccaa cctctcgtac atcggcgagg gcgcctacgg catggtgtgc | 360 |
| tctgcttatg ataatgtcaa caaagttcga gtagctatca agaaaatcag cccctttgag | 420 |
| caccagacct actgccagag aaccctgagg gagataaaaa tcttactgcg cttcagacat | 480 |
| gagaacatca ttggaatcaa tgacattatt cgagcaccaa ccatcgagca aatgaaagat | 540 |
| gtatatatag tacaggacct catggaaaca gatctttaca agctcttgaa gacacaacac | 600 |
| ctcagcaatg accatatctg ctattttctc taccagatcc tcagagggtt aaaatatatc | 660 |
| cattcagcta acgttctgca ccgtgacctc aagccttcca acctgctgct caacaccacc | 720 |
| tgtgatctca agatctgtga ctttggcctg gcccgtgttg cagatccaga ccatgatcac | 780 |
| acagggttcc tgacagaata tgtggccaca cgttggtaca gggctccaga aattatgttg | 840 |
| aattccaagg gctacaccaa gtccattgat atttggtctg taggctgcat tctggcagaa | 900 |
| atgctttcta acaggcccat ctttccaggg aagcattatc ttgaccagct gaaccacatt | 960 |
| ttgggtattc ttggatcccc atcacaagaa gacctgaatt gtataataaa tttaaaagct | 1020 |
| aggaactatt tgctttctct tccacacaaa ataaggtgc catggaacag ctgttccca | 1080 |
| aatgctgact ccaaagctct ggacttattg gacaaaatgt tgacattcaa cccacacaag | 1140 |
| aggattgaag tagaacaggc tctggcccac ccatatctgg agcagtatta cgacccgagt | 1200 |
| gacgagccca tcgccgaagc accattcaag ttcgacatgg aattggatga cttgcctaag | 1260 |
| gaaaagctca agaactaat ttttgaagag actgctagat tccagccagg atacagatct | 1320 |
| taaatttgtc aggtacctgg agtttaatac agtgagctct agcaagggag gcgctgcctt | 1380 |
| ttgtttctag aatattatgt tcctcaaggt ccattatttt gtattctttt ccaagctcct | 1440 |
| tattggaagg tattttttta aatttagaat taaaaattat ttagaaagtt acatataaaa | 1500 |
| aaaaaaaaaa aaaa | 1514 |

<210> SEQ ID NO 7
<211> LENGTH: 672
<212> TYPE: PRT
<213> ORGANISM: Homo sapiens

<400> SEQUENCE: 7

Met Ala Asp Val Phe Pro Gly Asn Asp Ser Thr Ala Ser Gln Asp Val
1               5                   10                  15

Ala Asn Arg Phe Ala Arg Lys Gly Ala Leu Arg Gln Lys Asn Val His
            20                  25                  30

Glu Val Lys Asp His Lys Phe Ile Ala Arg Phe Phe Lys Gln Pro Thr
        35                  40                  45

Phe Cys Ser His Cys Thr Asp Phe Ile Trp Gly Phe Gly Lys Gln Gly
    50                  55                  60

Phe Gln Cys Gln Val Cys Cys Phe Val Val His Lys Arg Cys His Glu
65                  70                  75                  80

Phe Val Thr Phe Ser Cys Pro Gly Ala Asp Lys Gly Pro Asp Thr Asp
                85                  90                  95

Asp Pro Arg Ser Lys His Lys Phe Lys Ile His Thr Tyr Gly Ser Pro
            100                 105                 110

Thr Phe Cys Asp His Cys Gly Ser Leu Leu Tyr Gly Leu Ile His Gln
        115                 120                 125

Gly Met Lys Cys Asp Thr Cys Asp Met Asn Val His Lys Gln Cys Val

-continued

```
            130                 135                 140
Ile Asn Val Pro Ser Leu Cys Gly Met Asp His Thr Glu Lys Arg Gly
145                 150                 155                 160

Arg Ile Tyr Leu Lys Ala Glu Val Ala Asp Glu Lys Leu His Val Thr
                165                 170                 175

Val Arg Asp Ala Lys Asn Leu Ile Pro Met Asp Pro Asn Gly Leu Ser
            180                 185                 190

Asp Pro Tyr Val Lys Leu Lys Leu Ile Pro Asp Pro Lys Asn Glu Ser
        195                 200                 205

Lys Gln Lys Thr Lys Thr Ile Arg Ser Thr Leu Asn Pro Gln Trp Asn
210                 215                 220

Glu Ser Phe Thr Phe Lys Leu Lys Pro Ser Asp Lys Asp Arg Arg Leu
225                 230                 235                 240

Ser Val Glu Ile Trp Asp Trp Asp Arg Thr Thr Arg Asn Asp Phe Met
                245                 250                 255

Gly Ser Leu Ser Phe Gly Val Ser Glu Leu Met Lys Met Pro Ala Ser
            260                 265                 270

Gly Trp Tyr Lys Leu Leu Asn Gln Glu Glu Gly Glu Tyr Tyr Asn Val
        275                 280                 285

Pro Ile Pro Glu Gly Asp Glu Glu Gly Asn Met Glu Leu Arg Gln Lys
    290                 295                 300

Phe Glu Lys Ala Lys Leu Gly Pro Ala Gly Asn Lys Val Ile Ser Pro
305                 310                 315                 320

Ser Glu Asp Arg Lys Gln Pro Ser Asn Asn Leu Asp Arg Val Lys Leu
                325                 330                 335

Thr Asp Phe Asn Phe Leu Met Val Leu Gly Lys Gly Ser Phe Gly Lys
            340                 345                 350

Val Met Leu Ala Asp Arg Lys Gly Thr Glu Glu Leu Tyr Ala Ile Lys
        355                 360                 365

Ile Leu Lys Lys Asp Val Val Ile Gln Asp Asp Asp Val Glu Cys Thr
    370                 375                 380

Met Val Glu Lys Arg Val Leu Ala Leu Leu Asp Lys Pro Pro Phe Leu
385                 390                 395                 400

Thr Gln Leu His Ser Cys Phe Gln Thr Val Asp Arg Leu Tyr Phe Val
                405                 410                 415

Met Glu Tyr Val Asn Gly Gly Asp Leu Met Tyr His Ile Gln Gln Val
            420                 425                 430

Gly Lys Phe Lys Glu Pro Gln Ala Val Phe Tyr Ala Ala Glu Ile Ser
        435                 440                 445

Ile Gly Leu Phe Phe Leu His Lys Arg Gly Ile Ile Tyr Arg Asp Leu
    450                 455                 460

Lys Leu Asp Asn Val Met Leu Asp Ser Glu Gly His Ile Lys Ile Ala
465                 470                 475                 480

Asp Phe Gly Met Cys Lys Glu His Met Met Asp Gly Val Thr Thr Arg
                485                 490                 495

Thr Phe Cys Gly Thr Pro Asp Tyr Ile Ala Pro Glu Ile Ile Ala Tyr
            500                 505                 510

Gln Pro Tyr Gly Lys Ser Val Asp Trp Trp Ala Tyr Gly Val Leu Leu
        515                 520                 525

Tyr Glu Met Leu Ala Gly Gln Pro Pro Phe Asp Gly Glu Asp Glu Asp
    530                 535                 540

Glu Leu Phe Gln Ser Ile Met Glu His Asn Val Ser Tyr Pro Lys Ser
545                 550                 555                 560
```

```
Leu Ser Lys Glu Ala Val Ser Ile Cys Lys Gly Leu Met Thr Lys His
            565                 570                 575

Pro Ala Lys Arg Leu Gly Cys Gly Pro Glu Gly Glu Arg Asp Val Arg
            580                 585                 590

Glu His Ala Phe Phe Arg Arg Ile Asp Trp Glu Lys Leu Glu Asn Arg
            595                 600                 605

Glu Ile Gln Pro Pro Phe Lys Pro Lys Val Cys Gly Lys Gly Ala Glu
            610                 615                 620

Asn Phe Asp Lys Phe Phe Thr Arg Gly Gln Pro Val Leu Thr Pro Pro
625                 630                 635                 640

Asp Gln Leu Val Ile Ala Asn Ile Asp Gln Ser Asp Phe Glu Gly Phe
            645                 650                 655

Ser Tyr Val Asn Pro Gln Phe Val His Pro Ile Leu Gln Ser Ala Val
            660                 665                 670

<210> SEQ ID NO 8
<211> LENGTH: 8787
<212> TYPE: DNA
<213> ORGANISM: Homo sapiens

<400> SEQUENCE: 8
```

| | | | | | |
|---|---|---|---|---|---|
| ggccgcagct | ccccggcgga | ggcaagaggt | ggttgggggg | gaccatggct | gacgttttcc | 60 |
| cgggcaacga | ctccacggcg | tctcaggacg | tggccaaccg | cttcgcccgc | aaaggggcgc | 120 |
| tgaggcagaa | gaacgtgcac | gaggtgaagg | accacaaatt | catcgcgcgc | ttcttcaagc | 180 |
| agcccacctt | ctgcagccac | tgcaccgact | tcatctgggg | gtttgggaaa | caaggcttcc | 240 |
| agtgccaagt | ttgctgtttt | gtggtccaca | agaggtgcca | tgaatttgtt | acttttcctt | 300 |
| gtccgggtgc | ggataaggga | cccgacactg | atgaccccag | gagcaagcac | aagttcaaaa | 360 |
| tccacactta | cggaagcccc | accttctgcg | atcactgtgg | gtcactgctc | tatggactta | 420 |
| tccatcaagg | gatgaaatgt | gacacctgcg | atatgaacgt | tcacaagcaa | tgcgtcatca | 480 |
| atgtccccag | cctctgcgga | atggatcaca | ctgagaagag | ggggcggatt | tacctaaagg | 540 |
| ctgaggttgc | tgatgaaaag | ctccatgtca | cagtacgaga | tgcaaaaaat | ctaatcccta | 600 |
| tggatccaaa | cgggctttca | gatccttatg | tgaagctgaa | acttattcct | gatcccaaga | 660 |
| atgaaagcaa | gcaaaaaacc | aaaaccatcc | gctccacact | aaatccgcag | tggaatgagt | 720 |
| cctttacatt | caattgaaaa | ccttcagaca | aagaccgacg | actgtctgta | gaaatctggg | 780 |
| actgggatcg | aacaacaagg | aatgacttca | tgggatccct | ttcctttgga | gtttcggagc | 840 |
| tgatgaagat | gccggccagt | ggatggtaca | agttgcttaa | ccaagaagaa | ggtgagtact | 900 |
| acaacgtacc | cattccggaa | ggggacgagg | aaggaaacat | ggaactcagg | cagaaattcg | 960 |
| agaaagccaa | acttggccct | gctggcaaca | aagtcatcag | tccctctgaa | gacaggaaac | 1020 |
| aaccttccaa | caaccttgac | cgagtgaaac | tcacggactt | caatttcctc | atggtgttgg | 1080 |
| gaaagggag | tttttggaaag | gtgatgcttg | ccgacaggaa | gggcacagaa | gaactgtatg | 1140 |
| caatcaaaat | cctgaagaag | gatgtggtga | ttcaggatga | tgacgtggag | tgcaccatgg | 1200 |
| tagaaaagcg | agtcttggcc | ctgcttgaca | aaccccgtt | cttgacgcag | ctgcactcct | 1260 |
| gcttccagac | agtggatcgg | ctgtacttcg | tcatggaata | tgtcaacggt | ggggacctca | 1320 |
| tgtaccacat | tcagcaagta | ggaaaattta | aggaaccaca | agcagtattc | tatgcggcag | 1380 |
| agatttccat | cggattgttc | tttcttcata | aagaggaat | catttatagg | gatctgaagt | 1440 |
| tagataacgt | catgttggat | tcagaaggac | atatcaaaat | tgctgacttt | gggatgtgca | 1500 |

```
aggaacacat gatggatgga gtcacgacca ggaccttctg tgggactcca gattatatcg    1560
ccccagagat aatcgcttat cagccgtatg gaaaatctgt ggactggtgg gcctatggcg    1620
tcctgttgta tgaaatgctt gccgggcagc ctccatttga tggtgaagat gaagacgagc    1680
tatttcagtc tatcatggag cacaacgttt cctatccaaa atccttgtcc aaggaggctg    1740
tttctatctg caaaggactg atgaccaaac acccagccaa gcggctgggc tgtgggcctg    1800 aggggagag ggacgtgaga gagcatgcct tcttccggag gatcgactgg gaaaaactgg     1860
agaacaggga gatccagcca ccattcaagc ccaaagtgtg tggcaaagga gcagagaact    1920
ttgacaagtt cttcacacga ggacagcccg tcttaacacc acctgatcag ctggttattg    1980
ctaacataga ccagtctgat tttgaagggt tctcgtatgt caaccccag tttgtgcacc     2040 ccatcttaca gagtgcagta tgaaactcac cagcgagaac aaaacacctcc ccagcccca    2100 gccctccccg cagtgggaag tgaatcctta accctaaaat tttaaggcca cggccttgtg    2160
tctgattcca tatggaggcc tgaaaattgt agggttatta gtccaaatgt gatcaactgt    2220
tcagggtctc tctcttacaa ccaagaacat tatcttagtg aagatggta cgtcatgctc      2280 agtgtccagt ttaattctgt agaagttacg tctggctcta ggttaaccct tcctagaaag    2340
caagcagact gttgccccat tttgggtaca atttgatata cttccatac cctccatctg      2400 tggattttc agcattggaa tcccccaacc agagatgtta aagtgagcct gtcccaggaa     2460
acatctccac ccaagacgtc tttggaatcc aagaacagga agccaagaga gtgagcaggg    2520
agggattggg ggtgggggag gcctcaaaat accgactgcg tccattctct gcctccatgg    2580
aaacagcccc tagaatctga aaggccggga taaacctaat cactgttccc aaacattgac    2640
aaatcctaac ccaaccatgg tccagcagtt accagtttaa acaaaaaaac ctcagatgag    2700
tgttgggtga atctgtcatc tggtaccctc cttggttgat aactgtcttg atactttca     2760 ttctttgtaa gaggccaaat cgtctaagga cgttgctgaa caagcgtgtg aaatcatttc    2820
agatcaagga taagccagtg tgtacatatg ttcattttaa tctctgggag attattttc     2880 catccagggt gccatcagta atcatgccac tactccaccag tgttgttcgc caacacccac   2940
ccccacacac accaacattt tgctgcctac cttgttatcc ttctcaagaa gctgaagtgt    3000
acgccctctc cccttttgtg cttatttatt taataggctg cagtgtcgct tatgaaagta    3060
cgatgtacag taacttaatg gaagtgctga ctctagcatc agcctctacc gattgatttt    3120
cctcccttct ctagccctgg atgtccactt agggataaaa agaatatggt tttggttccc    3180
atttctagtt cacgttgaat gacaggcctg gagctgtaga atcaggaaac ccggatgcct    3240
aacagctcaa agatgttttg ttaatagaag gatttaata cgttttgcaa atgcatcatg      3300
caatgaattt tgcatgttta taaaacct taataacaag tgaatctata ttattgatat       3360
aatcgtatca agtataaaga gagtattata ataatttat aagacacaat tgtgctctat      3420
ttgtgcaggt tcttgtttct aatcctcttt tctaattaag ttttagctga atcccttgct    3480
tctgtgcttt ccctccctgc acatgggcac tgtatcagat agattacttt ttaaatgtag    3540
ataaaatttc aaaaatgaat ggctagttta cgtgatagat taggctctta ctacatatgt    3600
gtgtgtatat atatgtattt gattctacct gcaaacaaat ttttattggt gaggactatt    3660
tttgagctga cactccctct tagtttcttc atgtcacctt tcgtcctggt tcctccgcca    3720
ctcttcctct tggggacaac aggaagtgtc tgattccagt ctgcctagta cgttggtaca    3780
cacgtggcat tgccgcagca cctgggctga cctttgtgtg tgcgtgtgtg tgtgtttcct    3840
```

```
tcttcccttc agcctgtgac tgttgctgac tccaggggtg ggagggatgg ggagactccc      3900
ctcttgctgt gtgtactgga cacgcaggaa gcatgctgtc ttgctgcctc tgcaacgacc      3960
tgtcgtttgc tccagcatgc acaaacttcg tgagaccaac acagccgtgc cctgcaggca      4020
ccagcacgtg cttttcagag gctgcggact ttcttccagc cattgtggca ttggcctttc      4080
cagtcttggg aggagcgcgc tgctttggtg agacaccccc atgcaaggtc ctcagagtag      4140
ccgggttcta ccacaaacag aaacagaatg aaagtagctg tcagtccttg tagagagccg      4200
ctctgtttcc tcccagaagc atctcccagc taagctcgca ttattttct cctctggctg       4260
tttgcctgaa gttcacagaa cacacaacca tgaaaggctt tttgaggtga gaggcccagg      4320
tggtcctggc aaccctgagt agaaggagag acggggtagg gaacgggccc ggccagaaaa      4380
gaaccatttc ttctgccatc ttttatgcac catagacatc gagactccag ggggtcctgg      4440
ctcccctgtc cctgcagccc tgcaggtcag tgcatgatct gggttcgtgt cctgaccagg      4500
tgctcctcct ttgatccgag gggaaaggga ctggtttata gaaagagcct aggagacaaa      4560
agggccagtc cccctgccca gaatggagca gcagcaggac agaccccac gaggccccc        4620
agagaggagg aagatcccac ggaggaacac atgaggttag ggacccttgt tcagcacccc      4680
aaacagcctg cctgtttaaa gcaggcagca ggcttaggcc ttccctgcaa ccccaacacc      4740
cacaagtttg tttctctagg aaacacattc actgtctcag ctggctgtta ctctctcaga      4800
ccatatggca aagttttcca agaaaatgcc ccgacagggg tgcccagcac actgcctgag      4860
ggacaacaga catcagaaca aacccccaga gagaaacagt caaaatcagg gcccggtgca      4920
gtgttgtcat gtggaacctg ctttatccat tgctgagtgt tgaatgtggg taatggttag     4980
ggctttccag atctcagcag ccaaagacag ttattgttgg aagactgtca tgtagataac      5040
catgagcaat ggctcgcctc agaatcagtt cataaaattc tatggtactg gccccttcgt      5100
gggtattgtg tgaaatgaga tggtggcgag gggtgcgctg tggaactgcc gcagccacgc      5160
aggaggtccc tgggggatgc tttgggaagt ccttgcccct gagcactgcc tgattgccag      5220
ggcctgtgga ggtctaggcc gcctggcaga atctagcacc gtccgaatcc ccgcaggacc      5280
catggagcta tgaccacacc aggccattca aatggctctg cattatcttc ccttggaagg      5340
tggccactcc tcggtggcag ggcctttccc tgaggctgca ggccgtgggc tggcagcccg      5400
tctcttggca tttcaattga aggtcaccag gtgctgggtt tgaaaggaag tcactggagt      5460
gctgccaggg gccgccctcc aaggttaatg agaggcccac atccaggcaa gaactaattc      5520
aaaaggcaga tcagaaacca caggagtcaa aattattgct ccggcagtgc ttcccttcct      5580
ttcatccact ggcctcgtgt ggtccatgca gggccactgt ctgcccttc tgatgccacg       5640
tattaggctt tcttactcag aattttgata gaaaaccatg gggccaagag ctctggaagc      5700
ctggccggaa agaccaaggt tcatgcagcc caacaaatga ttgttgagca cctctcggag      5760
ccaaagtcct taggcgagtg tggtgacttc ctggaaggag gatgcagact tccagagagc      5820
ccccccaacg gacgtgctga aaggagagg ggaggcgggg gctgtagtca ggaaggagcc      5880
agagaagaac agggtttggg tgcatccaga aatatgcctg cagtaggagg gagaggaagg      5940
ggtgccaccg tcaacggctt cccatcggag gtggttggtg cagatggaag tttctgtctg      6000
ctggccctca agagagtgtt ttgccaggga cacagtctgt tcctcctcag aaaacaccc       6060
ccaaatgcta acaacatccc caccagctgc tagaagcccc tttcccctcc ccaccttgaa      6120
gtagctcata gttctctggg cagagccaga ccatccagtg taccccagag gccagtaggt      6180
tcctgcccat tttcctctct ggcttcctgc caagaattat ggcagctgag gatgaatgga     6240
```

```
gaagtaaaaa caactaacac cgcacaacta acaactaaca ccgcagttcc cacctgggtt   6300
ccacttagca ggagacattt cggagggttt tttttgtttt tgttcctgtt ttttttttt    6360 ttgctggaat ttgttttctc agtactgaaa agagaaaaag tgacaatctt gtatttttaa   6420
aagcctcgga aaggtgatac catctgacag tcatttctc acgttggtct tctaaagtca    6480
cctatttctt gtgtgtgcac atcacaccat ttcctgtttc tttataaccc gacaagggta   6540
ggagtgcctg tttcccctgc tgggcacacc agacaatcgt aatcacaaaa cagacactga   6600
gccaggggcc caaagggtgt gatcatgaga gttaccggga cagcagtagg catgacagtc   6660
accaggaagg acaagggtgc tctgttgtta gtggccacac accaatttga caaggagtgt   6720
tgcgaaattt ttatttattt atttatttat tttgagatgg agtttcactc ttgttgccca   6780
ggctggagtg cggtggtaca atctcggctc actgcaacct ccacctccca ggttcaagcg   6840
attctcctgc ctcagcctcc caagtacctg ggactacagg tgcgtgccac cacacccagc   6900
taaattttgt gttttagta gagatggggt ttcaccatgt tggccaggat ggtcttgaac    6960
ccctgacctc atgatctgcc tgcctcggcc tcccaaagtg ctgggattac aggcatgagc   7020
caccacgccc agccaaaata tttttttaaa gtcattttcc ttaagctgct tgggctacat   7080
gtgaaataca ctgacggtc aacattcctg tctcctccca tttgggctga tgcagcagat    7140
ccagggaatt ttacctgttt ctgctgctag aagatccagg aaattgggaa ggttacctga   7200
cgcacacatg gatgaaggcc atcatctaga aatggggtca accacaattg tgttaattcc   7260
gtagtgtcag ggattcttcg ggaaggtcaa cagtatgaag gattctgacc cctgtgcctc   7320
ccatttatgt gatcaggtga cagttaataa ccgtggaggt cacactcagc catccaacag   7380
ccttacagtg accctacaca aaagccccca aattccaaag acttttcttt aacctaaagg   7440
aagaaattat tgttaattc cagtagagca actgaatata ctgggctatt tgtactttt     7500 tatagagaac tttaataata attctttaaa aatgagtttt tagaacaaag caactgacga   7560
tttcctaaga ttccaatgcc ctggagcttg taggaggact tagcctgggt cagctggagc   7620 accccccgacc tgatctccca ctgccagatt ttcccatgct cctagggtat ggagtccacg  7680
tgggaatgac tgcaagttca ggtggaactt ggccgactga tgctctgcga gttttaata   7740 gacactgggg acaactgctt aaggtttaga aacttccaaa ccacaggaaa gacattttta   7800
gtgtccccca tccagaggca gccctggaat aggattccca ggggtttctg ggaccccttt   7860
ccttgctccg tgaggctctg tggccatctt ttggcaggag gaggatgctt ccttggctct   7920
gtgcccagac ccgcctggtc cccaggtctc tcaccttggg tgaagattca gagatgccct   7980
gtaaggattt tgcccactgg gcaactcaga aatacttcga tctcccaaga tataagaggc   8040
agcagcaaac gtgcctattg acgtctgttt catagttacc acttacgcga gtagacagaa   8100
ctcggctttt cagaaaatag gtgtcaagtc cactttataa gaacctttt ttctaaaata    8160 agataaaagg tggctttgca ttttctgatt aaacgactgt gtctttgtca cctctgctta   8220
actttaggag tatccattcc tgtgattgta gacttttgtt gatattcttc ctggaagaat   8280
atcattcttt tcttgaaggg ttggtttact agaatattca aaatcaatca tgaaggcagt   8340
tactattttg agtctaaagg ttttctaaaa attaacctca catcccttct gttagggtct   8400
ttcagaatat cttttataaa cagaagcatt tgaagtcatt gcttttgcta catgatttgt   8460
gtgtgtgaag gacataccac gtttaaatca ttaattgaaa aacatcatat aagccccaac   8520
tttgtttgga ggaagagacg gaggttgagg ttttccttc tgtataagca cctactgaca    8580
```

-continued

```
aaatgtagag gccattcaac cgtcaaacac catttggtta tatcgcagag gagacggatg   8640
tgtaaattac tgcattgctt tttttttcag tttgtataac ctctaatctc cgtttgcatg   8700
atacgctttg ttagaaacat taattgtagt ttggaagcaa gtgtgtatga ataaagataa   8760
tgatcattcc aaaaaaaaaa aaaaaaa                                       8787
```

COMPOSITIONS AND METHODS FOR TREATING VASCULAR EHLERS DANLOS SYNDROME AND ASSOCIATED DISORDERS

CROSS-REFERENCE TO RELATED APPLICATIONS

This application is a National Stage Application filed under 35 U.S.C. § 371, of International Patent Application No PCT/US2019/056616, filed on Oct. 16, 2019, which claims the benefit of and priority to U.S. Provisional Application No. 62/746,524, filed on Oct. 16, 2018, U.S. Provisional Application No. 62/747,587, filed Oct. 18, 2018 and U.S. Provisional Application No. 62/838,049, filed Apr. 24, 2019. The entire contents of each of these application are incorporated herein by reference in their entirety.

STATEMENT AS TO FEDERALLY SPONSORED RESEARCH

This invention was made with government support under grant number 5T32GM007309-44 awarded by the National Institutes of Health. The government has certain rights in the invention.

INCORPORATION BY REFERENCE OF SEQUENCE LISTING

The contents of the sequence listing text file named "048317-559001WO_Sequence_Listing_txt", which was created on Oct. 16, 2019 and is 46,069 bytes in size, are incorporated herein by reference in its entirety.

This application claims the benefit of U.S. Provisional Application 62/838,049 filed Apr. 24, 2019, U.S. Provisional Application 62/747,587 filed on Oct. 18, 2018 and U.S. Provisional Application 62/746,524 filed on Oct. 16, 2018. The entire contents of these applications are incorporated herein by reference in their entirety.

FIELD

The present invention relates to connective tissue disorders.

BACKGROUND

Vascular Ehlers-Danlos Syndrome (vEDS) is an inherited connective tissue disorder caused by heterozygous mutations in the COL3A1 gene. Patients with vascular EDS have thin, translucent skin, easy bruising, a characteristic facial appearance, and develop spontaneous dissection in medium-to-large blood vessels and organ (uterus, colon) rupture, which results in premature death and a median survival of about 45 years[1].

Many features of vEDS are distinctly different from other heritable vasculopathies, such as Marfan syndrome (MFS) and Loeys-Dietz Syndrome (LDS), which have been associated with excessive TGF-β activity. These features include aortic dissection without prior aneurysm and rupture in any medium or large vessel, as well as in hollow organs. These features make disease prediction and monitoring difficult or impossible, and the presenting signs in the majority of adults diagnosed with vEDS are vascular dissection or organ rupture, with 25% of patients experiencing a major complication by age 20 years[1,2]. Thus, there is an unmet need for treating vEDS and related connective tissue disorders.

SUMMARY

Provided herein are, inter alia, compositions, formulations and methods for inhibiting, treating, preventing, and/or reducing the symptoms of severity of connective tissue disorders, e.g., vasculopathies. Aspects of the present subject matter relate to the use of agents for the treatment of a wide variety of connective tissue disorders. In particular embodiments, the connective tissue disorder comprises a vasculopathy, and in certain embodiments, the vasculopathy comprises vascular Ehlers-Danlos Syndrome (vEDS).

Included herein is a method for treating a vasculopathy (e.g., vEDS) in a subject. The method comprises administering to the subject, an effective amount of an agent, such that the agent decreases the activity or expression of extracellular signal-regulated kinase (ERK) or protein kinase C (PKC).

In certain embodiments, an agent inhibits the expression of mitogen activated protein kinase/extracellular signal regulated kinase (MEK), extracellular signal regulated kinase (ERK), phospholipase C (PLC), inositol triphosphate (IP3) or protein kinase C (pKC), and thereby inhibiting the activity of ERK, PLC, IP3, or PKC.

In certain embodiments, an agent inhibits the activity or expression of one or more molecules associated with the mitogen-activated protein kinase (MAPK) pathway, e.g. RAS-RAF/MEK/Extracellular signal-regulated kinase (ERK) protein kinases.

In embodiments, the agent comprises an antibody or fragment thereof, a polypeptide, a small molecule, a nucleic acid molecule, or any combination thereof. In particular embodiments, the agent comprises a small molecule.

In some cases, the agent comprises a small molecule. A small molecule is a compound that is less than 2000 Daltons in mass. The molecular mass of the small molecule is preferably less than 1000 Daltons, more preferably less than 600 Daltons, e.g., the compound is less than 500 Daltons, less than 400 Daltons, less than 300 Daltons, less than 200 Daltons, or less than 100 Daltons.

Small molecules are organic or inorganic. Exemplary organic small molecules include, but are not limited to, aliphatic hydrocarbons, alcohols, aldehydes, ketones, organic acids, esters, mono- and disaccharides, aromatic hydrocarbons, amino acids, and lipids. Exemplary inorganic small molecules comprise trace minerals, ions, free radicals, and metabolites. Alternatively, small molecules can be synthetically engineered to consist of a fragment, or small portion, or a longer amino acid chain to fill a binding pocket of an enzyme. Typically small molecules are less than one kilodalton.

In some cases, the agent comprises a nucleic acid molecule. For example, ribonucleic acid (RNA) or deoxyribonucleic acid (DNA) inhibits the expression of mitogen activated protein kinase/extracellular signal regulated kinase (MEK), extracellular signal regulated kinase (ERK), phospholipase C (PLC), inositol triphosphate (IP3) or protein kinase C (pKC), and thereby inhibiting the activity of ERK, PLC, IP3, or PKC. In some cases, the nucleic acid comprises small interfering RNA (siRNA), RNA interference (RNAi), messenger RNA (mRNA), small hairpin RNA or short hairpin RNA (shRNA), double stranded ribonucleic acid (dsRNA), antisense RNA or microRNA, or any portion thereof. However, the skilled artisan could readily identify additional nucleic acids that inhibit/antagonize or activate/agonist ERK or PKC, or IP3 or PLC.

Polynucleotides, polypeptides, or other agents, as used herein are purified and/or isolated. Specifically, as used herein, an "isolated" or "purified" nucleic acid molecule, polynucleotide, polypeptide, or protein, is substantially free of other cellular material, or culture medium when produced by recombinant techniques, or chemical precursors or other chemicals when chemically synthesized. Purified compounds are at least 60% by weight (dry weight) the compound of interest. Preferably, the preparation is at least 75%, more preferably at least 90%, and most preferably at least 99%, by weight the compound of interest. For example, a purified compound is one that is at least 90%, 91%, 92%, 93%, 94%, 95%, 98%, 99%, or 100% (w/w) of the desired compound by weight. Purity is measured by any appropriate standard method, for example, by column chromatography, thin layer chromatography, or high-performance liquid chromatography (HPLC) analysis. A purified or isolated polynucleotide (ribonucleic acid (RNA) or deoxyribonucleic acid (DNA)) is free of the genes or sequences that flank it in its naturally-occurring state. A purified or isolated polypeptide is free of the amino acids or sequences that flank it in its naturally-occurring state. Purified also defines a degree of sterility that is safe for administration to a human subject, e.g., lacking infectious or toxic agents.

In embodiments, the agent comprises cobimetinib, or a pharmaceutically acceptable salt thereof. In other embodiments, the agent comprises ruboxistaurin, or a pharmaceutically acceptable salt thereof. In other embodiments, the agent comprises enzastaurin, or a pharmaceutically acceptable salt thereof. In other contemplated embodiments, the agent comprises sotrastaurin, or a pharmaceutically acceptable salt thereof.

In alternative embodiments, the method further comprises administering an agent that decreases the activity or expression of phospholipase C (PLC) or inositol triphosphate (IP3).

In embodiments, the method comprises administering an effective amount of the agent. The effective amount of the agent is from about 0.001 mg/kg to about 250 mg/kg body weight, e.g., about 0.001 mg/kg, about 0.05 mg/kg, about 0.1 mg/kg, about 0.5 mg/kg, about 1 mg/kg, about 5 mg/kg, about 10 mg/kg, about 25 mg/kg, about 50 mg/kg, about 75 mg/kg, about 100 mg/kg, about 125 mg/kg, about 150 mg/kg, about 175 mg/kg, about 200 mg/kg, about 225 mg/kg, or about 250 mg/kg body weight. Ultimately, the attending physician or veterinarian decides the appropriate amount and dosage regimen.

In some cases, the agent is administered at least once per day, at least once per week, or at least once per month. The agent suitably may be administered for a duration of one day, one week, one month, two months, three months, six months, 9 months, or one year. In some cases, the agent is administered daily, e.g., every 24 hours. Or, the agent is administered continuously or several times per day, e.g., every 1 hour, every 2 hours, every 3 hours, every 4 hours, every 5 hours, every 6 hours, every 7 hours, every 8 hours, every 9 hours, every 10 hours, every 11 hours, or every 12 hours.

Furthermore, the methods described herein prevent or reduce the severity of a vasculopathy (vEDS) by at least about 1%, e.g., at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 99%.

A variety of administration routes are available. For example, the agent is administered topically, orally, via inhalation, or via injection.

The subject is preferably a mammal in need of such treatment or prophylaxis, e.g., a subject that has been diagnosed with a vasculopathy or a predisposition thereto. The mammal is any mammal, e.g., a human, a primate, a mouse, a rat, a dog, a cat, a horse, as well as livestock or animals grown for food consumption, e.g., cattle, sheep, pigs, chickens, and goats. In a preferred embodiment, the mammal is a human.

In aspects, a subject who has or is at risk of suffering from a connective tissue disorder, e.g., a vasculopathy (and in certain embodiments vEDS), has a level of ERK or PKC protein or mRNA that is different than a normal control. In some embodiments, a test sample obtained from the subject comprises a level of ERK or PKC protein or mRNA that is different than a normal control. For example, the test sample may comprise a level of ERK or PKC protein or mRNA that is at least about 5%, 10%, 15%, 20%, 25%, 30%, 40%, 45%, 50%, 55%, 60%, 65%, 70%, 75%, 80%, 90%, 95%, 99%, 100%, 5-50%, 50-75%, 75-100%, 1-fold, 2-fold, 3-fold, 4-fold, or 5-fold higher compared to a normal control.

In certain embodiments, the test sample may comprise a level of ERK or PKC activity that is at least about 5%, 10%, 15%, 20%, 25%, 30%, 40%, 45%, 50%, 55%, 60%, 65%, 70%, 75%, 80%, 90%, 95%, 99%, 100%, about 5 to about 50%, about 50 to about 75%, about 75 to about 100%, 1-fold, 2-fold, 3-fold, 4-fold, or 5-fold higher compared to a normal control.

A "control" sample or value refers to a sample that serves as a reference, usually a known reference, for comparison to a test sample. For example, a test sample can be taken from a test subject, e.g., a subject with a connective tissue disorder such as a vasculopathy (e.g., vEDS) or in need of diagnosis, and compared to samples from known conditions, e.g., a subject (or subjects) that does not have the disease (a negative or normal control), or a subject (or subjects) who does have the disease (positive control). A control can also represent an average value gathered from a number of tests or results. One of skill in the art will recognize that controls can be designed for assessment of any number of parameters. One of skill in the art will understand which controls are valuable in a given situation and be able to analyze data based on comparisons to control values. Controls are also valuable for determining the significance of data. For example, if values for a given parameter are variable in controls, variation in test samples will not be considered as significant.

The term, "normal amount" with respect to a compound (e.g., a protein or mRNA) refers to a normal amount of the compound in an individual who does not have a connective tissue disorder such as a vasculopathy (e.g., vEDS) or in a healthy or general population. The amount of a compound can be measured in a test sample and compared to the "normal control" level, utilizing techniques such as reference limits, discrimination limits, or risk defining thresholds to define cutoff points and abnormal values (e.g., for a particular vEDS or a symptom thereof). The normal control level means the level of one or more compounds or combined compounds typically found in a subject known not suffering from a vEDS. Such normal control levels and cutoff points may vary based on whether a compounds is used alone or in a formula combining with other compounds into an index. Alternatively, the normal control level can be a database of compounds patterns from previously tested subjects who did not develop a vEDS or a particular symptom thereof (e.g., in the event the vEDS develops or a subject already having the vEDS is tested) over a clinically relevant time horizon.

The level that is determined may be the same as a control level or a cut off level or a threshold level, or may be increased or decreased relative to a control level or a cut off level or a threshold level. In some aspects, the control subject is a matched control of the same species, gender, ethnicity, age group, smoking status, body mass index (BMI), current therapeutic regimen status, medical history, or a combination thereof, but differs from the subject being diagnosed in that the control does not suffer from the disease (or a symptom thereof) in question or is not at risk for the disease.

Relative to a control level, the level that is determined may an increased level. As used herein, the term "increased" with respect to level (e.g., protein or mRNA level) refers to any % increase above a control level. In various embodiments, the increased level may be at least or about a 5% increase, at least or about a 10% increase, at least or about a 15% increase, at least or about a 20% increase, at least or about a 25% increase, at least or about a 30% increase, at least or about a 35% increase, at least or about a 40% increase, at least or about a 45% increase, at least or about a 50% increase, at least or about a 55% increase, at least or about a 60% increase, at least or about a 65% increase, at least or about a 70% increase, at least or about a 75% increase, at least or about a 80% increase, at least or about a 85% increase, at least or about a 90% increase, at least or about a 95% increase, relative to a control level Relative to a control level, the level that is determined may a decreased level. As used herein, the term "decreased" with respect to level (e.g., protein or mRNA level) refers to any % decrease below a control level. In various embodiments, the decreased level may be at least or about a 5% decrease, at least or about a 10% decrease, at least or about a 15% decrease, at least or about a 20% decrease, at least or about a 25% decrease, at least or about a 30% decrease, at least or about a 35% decrease, at least or about a 40% decrease, at least or about a 45% decrease, at least or about a 50% decrease, at least or about a 55% decrease, at least or about a 60% decrease, at least or about a 65% decrease, at least or about a 70% decrease, at least or about a 75% decrease, at least or about a 80% decrease, at least or about a 85% decrease, at least or about a 90% decrease, at least or about a 95% decrease, relative to a control level.

In aspects, the test sample obtained from the subject comprises blood, serum, plasma, saliva, tears, vitreous, cerebrospinal fluid, sweat, cerebrospinal fluid, or urine.

Also provided herein are methods for treating a connective tissue disorder in a subject. The method comprises administering an effective amount of an agent, wherein the agent decreases the activity or expression of extracellular signal-related kinase (ERK) or protein kinase C (PKC). In embodiments, the connective tissue disorder is selected from the group consisting of a vasculopathy (e.g., vEDS), Marfan Syndrome, Loeys-Dietz Syndrome, and Familal thoracic aortic aneurysm. Other examples include, without limitation amyopathic dermatomyositis; bizzare parosteal osteochondromatous proliferation; classical Ehlers-Danlos syndrome; dermatosparaxis Ehlers-Danlos syndrome; Ehlers-Danlos syndromes; eosinophilic fasciitis; epidermolysis bullosa (EB) Legg-Calve-Perthes disease; Marfan syndrome; melorheostosis; melorheostosis with osteopoikilosis; mixed connective tissue disease; negative rheumatoid factor polyarthritis; osteosclerosis with ichthyosis and premature ovarian failure; pacman dysplasia; Paget disease of bone; Paget disease of bone, familial; polymyositis; progressive deafness with stapes fixation; ribbing disease; scleroderma; temporomandibular ankyloses; twenty-nail dystrophy; vascular Ehlers-Danlos syndrome; Weill-Marchesani syndrome; Worth type autosomal dominant osteosclerosis. In certain embodiments, the connective tissue disorder comprises vasculopathy.

In addition to the treatment of Marfan Syndrome itself, the present invention also provides methods of treating a variety of Marfan-related disorders. In some embodiments, the Marfan-related disorder is selected from the group consisting of: Loeys-Dietz Syndrome, Familial Aortic Aneurysm, Bicuspid Aortic Valve with Aortic Dilation, Familial Ectopia Lentis (dislocated lens), Mitral Valve Prolapse Syndrome, Marfan Habitus, Congenital Contractural Arachnodactyly (Beals Syndrome), Stickler syndrome, Shprintzen-Goldberg syndrome, Weill-Marchesani syndrome, and Ehlers-Danlos syndrome.

In embodiments, the method for treating a connective tissue disorder comprises administering an agent, wherein the agent comprises an antibody or fragment thereof, a polypeptide, a small molecule, a nucleic acid molecule, or any combination thereof. In preferred embodiments, the comprises a small molecule.

In embodiments, the agent comprises cobimetinib, or a pharmaceutically acceptable salt thereof. In other embodiments, the agent comprises ruboxistaurin or a pharmaceutically acceptable salt thereof. In other embodiments, the agent comprises enzastaurin or a pharmaceutically acceptable salt thereof. In other contemplated embodiments, the agent comprises sotrastaurin, or a pharmaceutically acceptable salt thereof.

In alternative embodiments, the method further comprises administering an agent that decreases the activity or expression of phospholipase C (PLC) or inositol triphosphate (IP3). Also provided herein are pharmaceutical compositions for the treatment of a vasculopathy. In embodiments, the composition comprises an effective amount of an agent that decreases the activity or expression of extracellular signal-regulated kinase (ERK) or protein kinase C (PKC). The pharmaceutical composition comprises an agent, wherein the agent comprises an antibody or fragment thereof, a polypeptide, a small molecule, a nucleic acid molecule, or any combination thereof.

The composition described herein are administered via oral administration, intravenous administration, topical administration, parenteral administration, intraperitoneal administration, intramuscular administration, intrathecal administration, intralesional administration, intracranial administration, intranasal administration, intraocular administration, intracardiac administration, intravitreal administration, intraosseous administration, intracerebral administration, intraarterial administration, intraarticular administration, intradermal administration, transdermal administration, transmucosal administration, sublingual administration, enteral administration, sublabial administration, insufflation administration, suppository administration, inhaled administration, or subcutaneous administration.

Also provided herein are kits for treating vasculopathy. In embodiments, the kits comprise 1) a pharmaceutical composition of any of the compositions described herein and 2) written instructions for treating the vasculopathy.

In other aspects, methods for treating a connective tissue disorder (e.g., Marfan Syndrome) is contemplated. In embodiments, the method comprises administering an effective amount of an agent, wherein the agent comprises an antibody or fragment thereof, a polypeptide, a small molecule, a nucleic acid molecule, or any combination thereof. In certain embodiments, therapeutically effective amounts of one or more agents are co-administered to the subject.

In certain embodiments, the method for treating a connective tissue disorder (e.g., Marfan Syndrome) comprises administering an agent that decreases the activity or expression of protein kinase C (PKC). In certain embodiments, the method for treating a connective tissue disorder (e.g., Marfan Syndrome) comprises administering an agent that decreases the activity or expression of extracellular signal-regulated kinase (ERK). In certain embodiments, the method for treating a connective tissue disorder (e.g., Marfan Syndrome) comprises administering an agent that decreases the activity or expression of protein kinase C (PKC), an extracellular signal-regulated kinase (ERK) or a combination thereof.

In certain embodiments, the method for treating a connective tissue disorder (e.g., Marfan Syndrome) comprises administering an agent that decreases or inhibits the expression of mitogen activated protein kinase/extracellular signal regulated kinase (MEK), extracellular signal regulated kinase (ERK), phospholipase C (PLC), inositol triphosphate (IP3) or protein kinase C (pKC), and thereby inhibiting the activity of ERK, PLC, IP3, or PKC.

In certain embodiments, the method for treating a connective tissue disorder (e.g., Marfan Syndrome) comprises administering an agent that decreases or inhibits the activity or expression of one or more molecules associated with the mitogen-activated protein kinase (MAPK) pathway, e.g. RAS-RAF/MEK/Extracellular signal-regulated kinase (ERK) protein kinases.

In some embodiments, the patient is a human patient. In some embodiments, the patient is 15-years old or older. In some embodiments, the patient is an adult patient. In some embodiments, the patient is a pediatric patient.

In some embodiments, the method is initiated as soon as (or soon after) vEDS is diagnosed. In some embodiments, the method is initiated when the patient is 15 years old, or when first diagnosed.

In some embodiments, the patient is diagnosed based on a phenotype of vEDS, or based on a molecular test vEDS (e.g., the patient is determined to have vEDS based on one or more genetic tests such as a test that determines that the patient has a glycine substitution within the triple helix or a splice-site variant).

In some embodiments, the patient has a COL3A1 mutation. In some embodiments, the patient has a glycine substitution within the triple helix or a splice-site variant. In some embodiments, the patient has a missense substitutions for glycine in the repeating (Gly-X-Y)n sequence of the collagen triple helix, or and splice site variants that lead to in-phase exon-skipping. In some embodiments, the patient has a glycine substitution within the triple helix (Group I). In some embodiments, the patient has a splice-site variant, in-frame insertions-deletion or duplication (Group II). In some embodiments, the patient has a variant leading to haplo-insufficiency (Group III).

In some embodiments, the patient has previously had an acute vEDS-related event (e.g., an arterial event such as a rupture or dissection, an intestinal or uterine rupture) prior to the initial dose of one or more agents embodied herein, or a pharmaceutically acceptable salt thereof.

In certain embodiments, the agent decreases the PKC protein or mRNA level by at least about 5%, 10%, 15%, 20%, 25%, 30%, 40%, 45%, 50%, 55%, 60%, 65%, 70%, 75%, 80%, 90%, 95%, 99%, 100%, 5-50%, 50-75%, 75-100%, 1-fold, 2-fold, 3-fold, 4-fold, or 5-fold compared to a normal control. In other embodiments, the agent decreases the level of PKC activity by at least about 5%, 10%, 15%, 20%, 25%, 30%, 40%, 45%, 50%, 55%, 60%, 65%, 70%, 75%, 80%, 90%, 95%, 99%, 100%, 5-50%, 5-fold, compared to a normal control.

In some embodiments, the agent decreases the extracellular signal-regulated kinase (ERK) protein or mRNA level by at least about 5%, 10%, 15%, 20%, 25%, 30%, 40%, 45%, 50%, 55%, 60%, 65%, 70%, 75%, 80%, 90%, 95%, 99%, 100%, 5-50%, 50-75%, 75-100%, 1-fold, 2-fold, 3-fold, 4-fold, or 5-fold compared to a normal control. In other embodiments, the agent decreases the level of ERK activity by at least about 5%, 10%, 15%, 20%, 25%, 30%, 40%, 45%, 50%, 55%, 60%, 65%, 70%, 75%, 80%, 90%, 95%, 99%, 100%, 5-50%, 5-fold, compared to a normal control.

In embodiments, the agent for treating a connective tissue disorder (e.g., Marfan Syndrome) comprises enzastaurin, or a pharmaceutically acceptable salt thereof. In other embodiments, the agent for treating a connective tissue disorder (e.g., Marfan Syndrome) comprises sotrastaurin, or a pharmaceutically acceptable salt thereof. In other contemplated examples, the agent for treating a connective tissue disorder (e.g., Marfan Syndrome) comprises ruboxistaurin, or a pharmaceutically acceptable salt thereof.

Definitions

Unless defined otherwise, all technical and scientific terms used herein have the meaning commonly understood by a person skilled in the art to which this disclosure belongs. The following references provide one of skill with a general definition of many of the terms used in this disclosure: The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

The term "pharmaceutical composition" is meant any composition, which contains at least one therapeutically or biologically active agent and is suitable for administration to the patient. Any of these formulations can be prepared by well-known and accepted methods of the art. See, for example, Remington: The Science and Practice of Pharmacy, 20th edition, (ed. A. R. Gennaro), Mack Publishing Co., Easton, Pa., 2000.

By "G protein-coupled receptors (GPCR)" is meant a protein receptor that senses molecules outside a cell and activates, inside the cell, signal transduction pathways and, ultimately, cellular responses. GPCRs are called seven-transmembrane receptors because they pass through the cell membrane seven times.

By "agonist" is meant a chemical that binds to a receptor and activates the receptor to produce a biological response. Whereas an agonist causes an action, an "antagonist" blocks the action of the agonist and an inverse agonist causes an action opposite to that of the agonist. As used herein, the terms "antagonist" and "inhibitor" are used interchangeably to refer to any molecule that counteracts or inhibits, decreases, or suppresses the biological activity of its target molecule. In some embodiments, an agonist is a "superagonist" when it induces or increases the biological activity of its target molecule. In some embodiments, an antagonist is a "superantagonist" when it counteracts or inhibits, decreases, or suppresses the biological activity of its target molecule. Suitable inhibitors, antagonists, agonists include soluble receptors, peptide inhibitors, small molecule inhibitors, ligand fusions, and antibodies.

As used herein, the term "salt" refers to acid or base salts of the agents used herein. Illustrative but non-limiting examples of acceptable salts are mineral acid (hydrochloric acid, hydrobromic acid, phosphoric acid, sulfuric acid, and the like) salts, organic acid (acetic acid, propionic acid, glutamic acid, citric acid, and the like) salts, and quaternary ammonium (methyl iodide, ethyl iodide, and the like) salts.

As used herein, an "antagonist" may refer to an antibody or fragment thereof, peptides, polypeptide or fragments thereof, small molecules, and inhibitory nucleic acids or fragments thereof that interferes with the activity or binding of another, for example, by competing for the one or more binding sites of an agonist, but does not induce an active response.

By "wild type" or "WT" is meant the phenotype of the typical form of a species as it occurs in nature. Alternately, the wild type is conceptualized as a product of the standard, "normal" allele at a locus, in contrast to that produced by a non-standard, "mutant" allele.

The term "administering," as used herein, refers to any mode of transferring, delivering, introducing, or transporting an agent, for example, to a subject in need of treatment for a disease or condition. Such modes include, but are not limited to, oral, topical, intravenous, intraperitoneal, intramuscular, intradermal, intranasal, and subcutaneous administration.

By "co-administer" it is meant that a composition described herein is administered at the same time, just prior to, or just after the administration of additional therapies. The agent or the composition of the disclosure can be administered alone or can be co-administered to the patient. Co-administration is meant to include simultaneous or sequential administration of the compound individually or in combination (more than one compound or agent). The preparations can also be combined, when desired, with other active substances.

As used herein, "sequential administration" includes that the administration of two agents (e.g., the agents or compositions described herein) occurs separately on the same day or do not occur on a same day (e.g., occurs on consecutive days).

As used herein, "concurrent administration" includes overlapping in duration at least in part. For example, when two agents (e.g., any of the agents described herein that has bioactivity) are administered concurrently, their administration occurs within a certain desired time. The agents' administration may begin and end on the same day. The administration of one agent can also precede the administration of a second agent by day(s) as long as both agents are taken on the same day at least once. Similarly, the administration of one agent can extend beyond the administration of a second agent as long as both agents are taken on the same day at least once. The bioactive agents/agents do not have to be taken at the same time each day to include concurrent administration.

As used herein, "intermittent administration includes the administration of an agent for a period of time (which can be considered a "first period of administration"), followed by a time during which the agent is not taken or is taken at a lower maintenance dose (which can be considered "off-period") followed by a period during which the agent is administered again (which can be considered a "second period of administration"). Generally, during the second phase of administration, the dosage level of the agent will match that administered during the first period of administration but can be increased or decreased as medically necessary.

As used herein an "alteration" also includes a 2-fold or more change in expression levels or activity of a gene or polypeptide, for example, 5-fold, 10-fold, 20-fold, 30-fold, 40-fold, 50-fold, 100-fold, 500-fold, 1000-fold or more.

As defined herein, the term "inhibition," "inhibit," "inhibiting" and the like in reference to a protein-inhibitor (e.g., an ERK or PKC inhibitor, or PLC or IP3 inhibitor) interaction means negatively affecting (e.g., decreasing) the activity or function of the protein (e.g., decreasing the activity or amount of ERK or PKC, or PLC or IP3, decreasing the ability of ERK or PKC, or PLC or IP3 to bind to a receptor, decreasing the ability of a receptor to bind ERK or PKC, or decreasing ERK or PKC signaling upon the binding of ERK or PKC, or PLC or IP3 to a receptor) relative to the activity or function of the protein in the absence of the inhibitor. In embodiments, inhibition refers to reduction of a disease or symptoms of disease (e.g., connective tissue disorder). Similarly an "inhibitor" is a compound or protein that inhibits a target by binding, partially or totally blocking, decreasing, preventing, delaying, inactivating, desensitizing, or down-regulating activity.

By "ameliorate" is meant decrease, suppress, attenuate, diminish, arrest, or stabilize the development or progression of a disease such as, for example, a pseudo-allergic-type reaction.

By "amplify" is meant to increase the number of copies of a molecule. In one example, the polymerase chain reaction (PCR) is used to amplify nucleic acids.

By "binding" is meant having a physicochemical affinity for a molecule. Binding is measured by any of the methods of the disclosure, e.g., a drug/compound with a receptor expressed on a cell.

In this disclosure, "comprises," "comprising," "containing," "having," and the like can have the meaning ascribed to them in U.S. patent law and can mean "includes," "including," and the like; the terms "consisting essentially of" or "consists essentially" likewise have the meaning ascribed in U.S. patent law and these terms are open-ended, allowing for the presence of more than that which is recited so long as basic or novel characteristics of that which is recited are not changed by the presence of more than that which is recited, but excludes prior art embodiments.

By "effective amount" is meant the amount required to ameliorate the symptoms of a disease relative to an untreated patient. The effective amount of active compound(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated, kind of concurrent treatment, complications from the disease being treated or other health-related problems. Other therapeutic regimens or agents can be used in conjunction with the methods and agents of this disclosure. Adjustment and manipulation of established dosages (e.g., frequency and duration) are well within the ability of those skilled in the art.

For any agent described herein, the therapeutically effective amount (e.g., effective dose or effective amount) can be initially determined from cell culture assays. Target concentrations will be those concentrations of therapeutic drug(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring agent's effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the therapeutic drug being employed. The dose administered to a patient should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the agent. Thereafter, the dosage is increased by small increments until the optimum effect under circumstances is reached. Dosage amounts and intervals can be adjusted individually to provide levels of the administered agent effective for the particular clinical indication being treated. This will provide a therapeutic regimen that is commensurate with the severity of the individual's disease state.

The effective dose of the agent (e.g., pharmacological inhibitor) of the present disclosure for treating vEDS, treating Marfan Syndrome, and/or altering the expression or activity of the PLC/IP3/PKC/ERK signaling pathway may be from about 0.001 mg/kg to about 0.01 mg/kg of the agent, from about 0.01 mg/kg to about 0.1 mg/kg of the agent, from about 0.1 mg/kg to about 1.0 mg/kg of the agent, from about 1.0 mg/kg to about 5.0 mg/kg of the agent, from about 5.0 mg/kg to about 10 mg/kg of the agent, from about 10 mg/kg to about 15 mg/kg of the agent, from about 15 mg/kg to about 20 mg/kg of the agent, from about 20 mg/kg to about 25 mg/kg of the agent, from about 25 mg/kg to about 30 mg/kg of the agent, from about 30 mg/kg to about 35 mg/kg of the agent, from about 35 mg/kg to about 40 mg/kg of the agent, from about 40 mg/kg to about 45 mg/kg of the agent, from about 45 mg/kg to about 50 mg/kg of the agent, from about 50 mg/kg to about 55 mg/kg of the agent, from about 55 mg/kg to about 60 mg/kg of the agent, from about 60 mg/kg to about 65 mg/kg of the agent, from about 65 mg/kg to about 70 mg/kg of the agent, from about 70 mg/kg to about 75 mg/kg of the agent, from about 75 mg/kg to about 80 mg/kg of the agent, from about 80 mg/kg to about 85 mg/kg of the agent, from about 85 mg/kg to about 90 mg/kg of the agent, from about 90 mg/kg to about 95 mg/kg of the agent, or from about 95 mg/kg to about 100 mg/kg of the agent.

In some aspects, the present disclosure includes compositions with an effective dose of an agent(s) of the present disclosure in which the agent may be from about 0.1% to about 20% w/v of the composition. A weight percent of a component, unless specifically stated to the contrary, is based on the total weight of the formulation or composition in which the component is included.

For example, the effective dose of an agent disclosed herein may be from about 0.001%-about 0.01%, from about 0.01%-about 0.1%, from about 0.1%-about 1.0%, from about 1.0%-about 2.0%, from about 2.0%-about 3.0%, from about 3.0%-about 4.0%, from about 4.0%-about 5.0%, from about 5.0%-about 6.0%, from about 6.0%-about 7.0%, from about 7.0%-about 8.0%, from about 8.0%-about 9.0%, from about 9.0%-about 10%, from about 10%-about 11%, from about 11%-about 12%, from about 12%-about 13%, from about 13%-about 14%, from about 14%-about 15%, from about 15%-about 16%, from about 16%-about 17%, from about 17%-about 18%, from about 18%-about 19%, or from about 19%-about 20% w/v of the composition.

The terms "treating" and "treatment" as used herein refer to the administration of an agent or formulation to a clinically symptomatic individual afflicted with an adverse condition, disorder, or disease, so as to effect a reduction in severity and/or frequency of symptoms, eliminate the symptoms and/or their underlying cause, and/or facilitate improvement or remediation of damage.

The terms "subject," "patient," "individual," and the like as used herein are not intended to be limiting and can be generally interchanged. An individual described as a "subject," "patient," "individual," and the like does not necessarily have a given disease, but may be merely seeking medical advice. The terms "subject," "patient," "individual," and the like as used herein include all members of the animal kingdom that may suffer from the indicated disorder. In some aspects, the subject is a mammal, and in some aspects, the subject is a human.

The term "sample" as used herein refers to a biological sample obtained for the purpose of evaluation in vitro. In embodiments, the sample may comprise a body fluid. In some embodiments, the body fluid includes, but is not limited to, whole blood, plasma, serum, lymph, breast milk, saliva, mucous, semen, cellular extracts, inflammatory fluids, cerebrospinal fluid, vitreous humor, tears, vitreous, aqueous humor, or urine obtained from the subject. In some aspects, the sample is a composite panel of two or more body fluids. In exemplary aspects, the sample comprises blood or a fraction thereof (e.g., plasma, serum, or a fraction obtained via leukapheresis).

Ranges provided herein are understood to be shorthand for all of the values within the range. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50, as well as all intervening decimal values between the aforementioned integers such as, for example, 1.1, 1.2, 1.3, 1.4, 1.5, 1.6, 1.7, 1.8, and 1.9. With respect to sub-ranges, "nested sub-ranges" that extend from either end point of the range are specifically contemplated. For example, a nested sub-range of an exemplary range of 1 to 50 may comprise 1 to 10, 1 to 20, 1 to 30, and 1 to 40 in one direction, or 50 to 40, 50 to 30, 50 to 20, and 50 to 10 in the other direction.

By "recombinant" is meant nucleic acid molecules formed by laboratory methods of genetic recombination (such as molecular cloning) to bring together genetic material from multiple sources, creating sequences that would not otherwise be found in biological organisms.

The word "expression" or "expressed" as used herein in reference to a DNA nucleic acid sequence (e.g. a gene) means the transcriptional and/or translational product of that sequence. The level of expression of a DNA molecule in a cell may be determined on the basis of either the amount of corresponding mRNA that is present within the cell or the amount of protein encoded by that DNA produced by the cell (Sambrook et al., 1989 Molecular Cloning: A Laboratory Manual, 18.7-18.88). When used in reference to polypeptides, expression includes any step involved in the production of a polypeptide including, but not limited to, transcription, post-transcriptional modification, translation, post-translational modification, and secretion. Expression can be detected using conventional techniques for detecting protein (e.g., ELISA, Western blotting, flow cytometry, immunofluorescence, immunohistochemistry, etc).

By "reduces" is meant a negative alteration of at least 10%, 25%, 50%, 75%, or 100%.

By "reference" is meant a standard or control condition.

Unless specifically stated or obvious from context, as used herein, the terms "a," "an," and "the" are understood to be singular or plural. Unless specifically stated or obvious from context, as used herein, the term "or" is understood to be inclusive.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

As used herein, the term "derivative" refers to a compound having a structure derived from the structure of a parent compound (e.g. a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides and N-oxides of a parent compound.

Each embodiment disclosed herein is contemplated as being applicable to each of the other disclosed embodiments. Thus, all combinations of the various elements described herein are within the scope of the invention.

Other features and advantages of the invention will be apparent from the following description of the preferred embodiments thereof, and from the claims. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All published foreign patents and patent applications cited herein are incorporated herein by reference. Genbank and NCBI submissions indicated by accession number cited herein are incorporated herein by reference. All other published references, documents, manuscripts and scientific literature cited herein are incorporated herein by reference. In the case of conflict, the present specification, including definitions, will control. In addition, the materials, methods, and examples are illustrative only and not intended to be limiting.

BRIEF DESCRIPTION OF THE DRAWINGS

FIG. 1G is an immunoblot and a graph that demonstrated the signature for elevations in GPCR and MAPK signaling by immunoblotting for markers of active signaling through this pathway. It was found that ERK1/2 phosphorylation and PKC phosphorylation was significantly higher in vEDS aortas.

FIG. 2A is a graph depicting the survival of mice treated with cobimetinib, an FDA-approved inhibitor of MEK. A 94% survival was observed after 45 days of treatment, compared to only 55% survival with no treatment.

FIG. 2B is a graph depicting the survival of mice treated with ruboxistaurin, a well-tolerated orally administered pharmacologic agent that specifically inhibits PKC beta. A 100% survival was observed after 39 days of treatment, compared to only 55% survival with no treatment.

FIG. 2C is a graph depicting the survival of mice treated with hydralazine, which blocks the PLC/IP3/PKC/ERK axis. A protection of 98% survival was observed at 45 days of age, the median survival for an untreated vEDS mouse.

FIG. 7 is a graph depicting that male mice treated with bicalutamide alone lead to an intermediate survival of ~80% and males did not continue to survive following removal of bicalutamide after puberty, suggesting that inhibition of androgen signaling alone was not enough to prevent aortic disease in our mouse models of vEDS.

FIG. 12 is a graph depicting that treatment of the mice with a nonspecific tyrosine kinase receptor antagonist, nintedanib (50 mg/kg/d) showed had no impact on survival, suggesting that tyrosine kinase receptor activation was not driving the activation of PLC/IP3/PKC/ERK signaling pathway in vEDS mice.

FIG. 13A-13C are graphs depicting treatment of mice with a non-specific β antagonist, propranolol (80 mg/kg/d) (FIG. 13A), a specific β1 antagonist, atenolol (120 mg/kg/d) (FIG. 13B), and a β1 antagonist/β2 agonist, celiprolol (200 mg/kg/d) (FIG. 13C) showed that none of these manipulations lead to an improvement in survival in our vEDS mouse models, despite decreases in blood pressure.

FIG. 16A: Enzastaurin (60 mg/kg/d), also rescued the risk of death from aortic dissection, with 80% of enzastaurin treated vEDS mice surviving after 40 days of treatment compared to only 50% of untreated vEDS mice (p=0.0305).

FIG. 16B: Treatment with bosentan led to 80% survival after 40 days of treatment, compared to only 50% survival in untreated vEDS mice (p=0.0298).

FIG. 17 demonstrated PKC phosphorylation in two tissue samples (iliac artery and descending thoracic aorta) from patients with vEDS.

FIG. 18 demonstrates ERK1/2 phosphorylation in two tissue samples (iliac artery and descending thoracic aorta) from patients with vEDS.

FIG. 19 is a graph demonstrating that ruboxistaurin treatment reduces aortic root growth in 129 MFS mice.

DETAILED DESCRIPTION

Figure 1A:
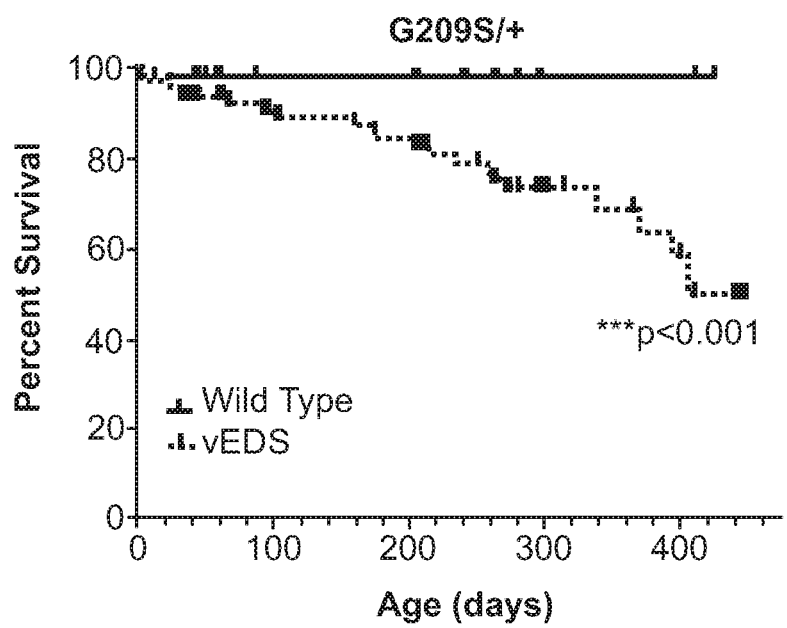
FIG. 1A is a graph demonstrating that the G209S/+ mouse model recapitulated vascular Ehlers-Danlos Syndrome (vEDS) phenotypes. The percent survival versus age is shown. The median survival was 400 days, p<0.0001.

The invention is based, at least in part, on the identification of a novel, targetable signaling abnormality that contributes to the pathogenesis of vEDS. In particular, it was observed that pharmacologic agents that inhibit ERK1/2 activation or PKC activation were able to successfully prevent death due to aortic dissection. Furthermore, agents that inhibit the activation of the PLC/IP3/PKC/ERK signaling pathway also prevent death due to aortic dissection. Taken together, these novel findings provide the first evidence for a targetable signaling abnormality that contributes to the pathogenesis of vEDS and potential other vasculopathies, as well as other connective tissue disorders.

Vasculopathy

Vasculopathy is a term used to describe a disease affecting blood vessels. It often includes vascular abnormalities caused by degenerative, metabolic and inflammatory conditions, embolic diseases, coagulative disorders, and functional disorders such as posteri or reversible encephalopathy syndrome. The etiology of vasculopathy is generally unknown and the condition is frequently not pathologically proven. Vasculitis, on the other hand, is a more specific term and is defined as inflammation of the wall of a blood vessel.

As used herein, "vasculitis (angiitis or angitis)" refers to inflammation of a blood vessel, e.g., arteritis, phlebitis, or lymphatic vessel, e.g., lymphangitis. Vasculitis can take various forms such as cutaneous vasculitis, urticarial vasculitis, leukocytoclastic vasculitis, livedo vasculitis and nodular vasculitis. Small vessel vasculitis may refer to inflammation of small or medium sized blood or lymphatic vessel, e.g., capillaries, venules, arterioles and arteries.

Vascular Ehlers-Danlos Syndrome (vEDS)

Vascular Ehlers-Danlos Syndrome (vEDS) is an inherited connective tissue disorder caused by heterozygous mutations in the collagen type III alpha 1 chain (COL3A1) gene. The major cause of mortality in vEDS is arterial dissection and/or rupture, but little is known about the pathogenesis of this disease. Effective treatment strategies for this devastating condition do not exist. The current belief is that reduced amounts of collagen III lead directly to the signs and symptoms of vEDS due to an inherent loss of structural integrity of the tissues. However, early pathogenic models of Marfan Syndrome (MFS) also singularly invoked tissue weakness imposed by failed elastogenesis, but subsequent work clearly demonstrated enhanced transforming growth factor beta (TGF-β) signaling in a mouse model deficient in fibrillin-1, the deficient gene product in MFS[3,4]. Follow-up work went on to show that TGF-β and downstream cellular signaling molecules were major mediators of disease pathology. Further, therapies that attenuate TGF-β signaling and related pathways, such as TGF-β neutralizing antibody (Nab), the angiotensin-II (Ang-II) type 1 receptor blocker (ARB) losartan, or the inhibitor of ERK1/2 activation RDEA119/trametinib, can suppress aortic disease in MFS mice[3-6].

However, similar to other heritable vasculopathies such as Marfan syndrome and Loeys-Dietz syndrome, provided herein are signaling abnormalities that are major mediators of disease pathology in vEDS. RNA-seq profiling on the aortas of mice with patient-derived Col3a1 mutations demonstrated elevated PLC/IP3/PKC/ERK signaling compared to wild-type aortas. Immunoblotting of the proximal descending thoracic aorta confirmed elevated PKC and ERK1/2 activation.

In certain embodiments, COL3A1 comprises the following amino acid sequence (NCBI Accession No: AAH28178.1 (SEQ ID NO: 1), incorporated herein by reference in its entirety):

```
   1 mmsfvqkgsw lllallhpti ilaqqeaveg gcshlgqsya drdvwkpepc qicvcdsgsv
  61 lcddiicddq eldcpnpeip fgeccavcpq pptaptrppn gqgpqgpkgd pgppgipgrn
 121 gdpgipgqpg spgspgppgi cescptgpqn yspqydsydv ksgvavggla gypgpagppg
 181 ppgppgtsgh pgspgspgyq gppgepgqag psgppgppga igpsgpagkd gesgrpgrpg
 241 erglpgppgi kgpagipgfp gmkghrgfdg rngekgetga pglkgenglp gengapgpmg
 301 prgapgergr pglpgaagar gndgargsdg qpgppgpgt agfpgspgak gevgpagspg
 361 sngapgqrge pgpqghagaq gppgppging spggkgemgp agipgapglm gargppgpag
 421 angapglrgg agepgkngak gepgprgerg eagipgvpga kgedgkdgsp gepganglpg
 481 aagergapgf rgpagpngip gekgpagerg apgpagprga agepgrdgvp ggpgmrgmpg
 541 spggpgsdgk pgppgsqges grpgppgpsg prgqpgvmgf pgpkgndgap gknerggpg
 601 gpgpqgppgk ngetgpqgpp gptgpggdkg dtgppgpqgl qglpgtggpp gengkpgepg
 661 pkgdagapga pggkgdagap gergppglag apglrggagp pgpeggkgaa gppgppgaag
 721 tpglqgmpge rgglgspgpk gdkgepggpg adgvpgkdgp rgptgpigpp gpagqpgdkg
 781 eggapglpgi agprgspger getgppgpag fpgapgqnge pggkgergap gekgeggppg
 841 vagppgkdgt sghpgpigpp gprgnrgerg segspghpgq pgppgppgap gpccggvgaa
 901 aiagiggeka ggfapyygde pmdfkintde imtslksvng qieslispdg srknparncr
 961 dlkfchpelk sgeywvdpnq gckldaikvf cnmetgetci sanpinvprk hwwtdssaek
1021 khvwfgesmd ggfqfsygnp elpedvldvq laflrllssr asqnityhck nsiaymdqas
1081 gnvkkalklm gsnegefkae gnskftytvl edgctkhtge wsktvfeyrt rkavrlpivd
1141 iapydiggpd qefgvdvgpv cfl
```

In certain embodiments, COL3A1 comprises the following nucleic acid sequence, the start and stop codons are bold and underlined (NCBI Accession No: NM_000090.3 (SEQ ID NO: 2), incorporated herein by reference in its entirety):

```
   1 ggctgagttt tatgacgggc ccggtgctga agggcaggga acaacttgat ggtgctactt
  61 tgaactgctt ttcttttctc cttttttgcac aaagagtctc atgtctgata tttagacatg
 121 atgagctttg tgcaaaaggg gagctggcta cttctcgctc tgcttcatcc cactattatt
 181 ttggcacaac aggaagctgt tgaaggagga tgttcccatc ttggtcagtc ctatgcggat
 241 agagatgtct ggaagccaga accatgccaa atatgtgtct gtgactcagg atccgttctc
 301 tgcgatgaca taatatgtga cgatcaagaa ttagactgcc ccaacccaga aattccattt
 361 ggagaatgtt gtgcagtttg cccacagcct ccaactgctc ctactcgccc tcctaatggt
 421 caaggacctc aaggccccaa gggagatcca ggccctcctg gtattcctgg gagaaatggt
 481 gaccctggta ttccaggaca accagggtcc cctggttctc tggccccccc tggaatctgt
 541 gaatcatgcc ctactggtcc tcagaactat tctccccagt atgattcata tgatgtcaag
 601 tctggagtag cagtaggagg actcgcaggc tatcctggac cagctggccc cccaggccct
 661 cccggtcccc ctggtacatc tggtcatcct ggttcccctg gatctccagg ataccaagga
 721 cccccctggtg aacctgggca agctggtcct tcaggccctc caggacctcc tggtgctata
 781 ggtccatctg gtcctgctgg aaaagatgga gaatcaggta gacccggacg acctggagag
 841 cgaggattgc ctggacctcc aggtatcaaa ggtccagctg ggatacctgg attccctggt
 901 atgaaaggac acagaggctt cgatggacga atggagaaaa gggtgaaac aggtgctcct
 961 ggattaaagg gtgaaaatgg tcttccaggc gaaaatggag ctcctggacc catgggtcca
1021 agaggggctc ctggtgagcg aggacggcca ggacttcctg gggctgcagg tgctcggggt
1081 aatgacggtg ctcgaggcag tgatggtcaa ccaggccctc tggtcctcc tggaactgcc
1141 ggattccctg gatcccctg tgctaagggt gaagttggac ctgcagggtc tcctggttca
1201 aatggtgccc ctggacaaag aggagaacct ggacctcagg acacgctgg tgctcaaggt
1261 cctcctggcc ctcctgggat taatggtagt cctggtggta aaggcgaaat gggtcccgct
1321 ggcattcctg gagctcctgg actgatggga gcccggggtc ctccaggacc agccggtgct
1381 aatggtgctc ctggactgcg aggtggtgca ggtgagcctg gtaagaatgt tgccaaagga
1441 gagcccggac acgtggtga acgcggtgag gctggtattc caggtgttcc aggagctaaa
1501 ggcgaagatg gcaaggatgg atcacctgga gaacctggtg caaatgggct tccaggagct
1561 gcaggagaaa ggggtgcccc tgggttccga ggacctgctg gaccaaatgg catcccagga
1621 gaaaagggtc ctgctggaga gcgtggtgct ccaggccctg cagggcccag aggagctgct
1681 ggagaacctg gcagagatgg cgtccctgga gtccaggaa tgagggcat gcccggaagt
1741 ccaggaggac caggaagtga tgggaaacca gggcctcccg gaagtcaagg agaaagtggt
1801 cgaccaggtc ctcctgggcc atctggtccc cgaggtcagc ctggtgtcat gggcttcccc
1861 ggtcctaaag gaaatgatgg tgctcctggt aagaatggag aacgaggtgg ccctggagga
1921 cctggccctc agggtcctcc tggaaagaat ggtgaaactg gacctcaggg accccaggg
1981 cctactgggc ctggtggtga caaaggagac acaggacccc ctggtccaca aggattacaa
2041 ggcttgcctg gtacaggtgg tcctccagga gaaaatggaa acctgggga accaggtcca
2101 aagggtgatg ccggtgcacc tggagctcca ggaggcaagg gtgatgctgg tgcccctggt
2161 gaacgtggac ctcctggatt ggcaggggcc ccaggactta gggtggagc tggtccccct
2221 ggtccgaag gaggaaaggg tgctgctggt cctcctgggc cacctggtgc tgctggtact
2281 cctggtctgc aaggaatgcc tggagaaaga ggaggtcttg gaagtcctgg tccaaagggt
```

```
-continued
2341 gacaagggtg aaccaggcgg tccaggtgct gatggtgtcc caggaaaaga tggcccaagg 2401 ggtcctactg gtcctattgg tcctcctggc ccagctggcc agcctggaga taagggtgaa 2461 ggtggtgccc ccggacttcc aggtatagct ggacctcgtg gtagccctgg tgagagaggt 2521 gaaactggcc ctccaggacc tgctggtttc cctggtgctc ctggacagaa tggtgaacct 2581 ggtggtaaag gagaaagagg ggctccgggt gagaaggtg aaggaggccc tcctggagtt 2641 gcaggacccc ctggaggttc tggacctgct ggtcctcctg gtccccaagg tgtcaaaggt 2701 gaacgtggca gtcctggtgg acctggtgct gctggcttcc ctggtgctcg tggtcttcct 2761 ggtcctcctg gtagtaatgg taacccagga cccccaggtc ccagcggttc tccaggcaag 2821 gatgggcccc caggtcctgc gggtaacact ggtgctcctg gcagccctgg agtgtctgga 2881 ccaaaaggtg atgctggcca accaggagag aagggatcgc ctggtgccca gggcccacca 2941 ggagctccag gcccacttgg gattgctggg atcactggag cacgggtct gcaggacca 3001 ccaggcatgc caggtcctag gggaagccct ggccctcagg gtgtcaaggg tgaaagtggg 3061 aaaccaggag ctaacggtct cagtggagaa cgtggtcccc ctggacccca gggtcttcct 3121 ggtctggctg gtacagctgg tgaacctgga agagatggaa accctggatc agatggtctt 3181 ccaggccgag atggatctcc tggtggcaag ggtgatcgtg gtgaaaatgg ctctcctggt 3241 gcccctggcg ctcctggtca tccaggccca cctggtcctg tcggtccagc tggaaagagt 3301 ggtgacagag gagaaagtgg ccctgctggc cctgctggtg ctcccggtcc tgctggttcc 3361 cgaggtgctc ctggtcctca aggcccacgt ggtgacaaag gtgaaacagg tgaacgtgga 3421 gctgctggca tcaaaggaca tcgaggattc cctggtaatc caggtgcccc aggttctcca 3481 ggccctgctg gtcagcaggg tgcaatcggc agtccaggac ctgcaggccc cagaggacct 3541 gttggaccca gtggacctcc tggcaaagat ggaaccagtg gacatccagg tcccattgga 3601 ccaccagggc ctcgaggtaa cagaggtgaa agaggatctg agggctcccc aggccacca 3661 gggcaaccag gccctcctgg acctcctggt gcccctggtc cttgctgtgg tggtgttgga 3721 gccgctgcca ttgctgggat tggaggtgaa aaagctggcg ttttgcccc gtattatgga 3781 gatgaaccaa tggattctcaa aatcaacacc gatgagatta tgacttcact caagtctgtt 3841 aatggacaaa tagaaagcct cattagtcct gatggttctc gtaaaaaccc cgctagaaac 3901 tgcagagacc tgaaattctg ccatcctgaa ctcaagagtg gagaatactg ggttgaccct 3961 aaccaaggat gcaaattgga tgctatcaag gtattctgta atatggaaac tgggaaaaca 4021 tgcataagtg ccaatccttt gaatgttcca cggaaacact ggtggacaga ttctagtgct 4081 gagaagaaac acgtttggtt tggagagtcc atggatggtg gttttcagtt tagctacggc 4141 aatcctgaac ttcctgaaga tgtccttgat gtgcagctgg cattccttcg acttctctcc 4201 agccgagctt cccagaacat cacatatcac tgcaaaaata gcattgcata catggatcag 4261 gccagtggaa atgtaaagaa ggccctgaag ctgatggggt caaatgaagg tgaattcaag 4321 gctgaaggaa atagcaaatt cacctacaca gttctggagg atggttgcac gaaacacact 4381 ggggaatgga gcaaaacagt ctttgaatat cgaacacgca aggctgtgag actacctatt 4441 gtagatattg caccctatga cattggtggt cctgatcaag aatttggtgt ggacgttggc 4501 cctgtttgct ttttataaac caaactctat ctgaaatccc aacaaaaaaa atttaactcc 4561 atatgtgttc ctcttgttct aatcttgtca accagtgcaa gtgaccgaca aaattccagt 4621 tatttatttc caaaatgttt ggaaacagta aatttgaca agaaaaatg atacttctct 4681 ttttttgctg ttccaccaaa tacaattcaa atgcttttg ttttatttt ttaccaattc 4741 caatttcaaa atgtctcaat ggtgctataa taaataaact tcaacactct ttatgataac
```

```
4801 aacactgtgt tatattcttt gaatcctagc ccatctgcag agcaatgact gtgctcacca 4861 gtaaaagata acctttcttt ctgaaatagt caaatacgaa attagaaaag ccctccctat 4921 tttaactacc tcaactggtc agaaacacag attgtattct atgagtccca gaagatgaaa 4981 aaaattttat acgttgataa aacttataaa tttcattgat taatctcctg gaagattggt 5041 ttaaaaagaa aagtgtaatg caagaattta aagaaatatt tttaaagcca caattatttt 5101 aatattggat atcaactgct tgtaaaggtg ctcctctttt ttcttgtcat tgctggtcaa 5161 gattactaat atttgggaag gctttaaaga cgcatgttat ggtgctaatg tactttcact 5221 tttaaactct agatcagaat tgttgacttg cattcagaac ataaatgcac aaaatctgta 5281 catgtctccc atcagaaaga ttcattggca tgccacaggg gattctcctc cttcatcctg 5341 taaaggtcaa caataaaaac caaattatgg ggctgctttt gtcacactag catagagaat 5401 gtgttgaaat ttaactttgt aagcttgtat gtggttgttg atctttttt tccttacaga 5461 cacccataat aaaatatcat attaaaattc
```

MAP/ERK Pathway

The MAPK/ERK pathway (also known as the Ras-Raf-MEK-ERK pathway) is a chain of proteins in the cell that communicates a signal from a receptor on the surface of the cell to the DNA in the nucleus of the cell.

The signal starts when a signaling molecule binds to the receptor on the cell surface and ends when the DNA in the nucleus expresses a protein and produces some change in the cell, such as cell division. The pathway includes many proteins, including MAPK (mitogen-activated protein kinases, originally called ERK, extracellular signal-regulated kinases), which communicate by adding phosphate groups to a neighboring protein, which acts as an "on" or "off" switch.

The term "ERK" refers to any human ERK1 or ERK2 gene or protein. ERK1 is known by several names including, for example, mitogen-activated protein kinase 3, extracellular signal-regulated kinase 1, insulin-stimulated MAP2 kinase, MAP kinase 1, MAPK 1, p44-ERK1, ERT2, p44-MAPK or microtubule-associated protein 2 kinase.

ERK2 is known by several names including, for example, mitogen-activated protein kinase 1, extracellular signal-regulated kinase 2, mitogen-activated protein kinase 2, MAP kinase 2, MAPK 2, p42-MAPK, or ERT1.

In certain embodiments, ERK1 comprises the following amino acid sequence (NCBI Accession No: P27361.4 (SEQ ID NO: 3), incorporated herein by reference in its entirety):

```
  1 MAAAAAQGGG GGEPRRTEGV GPGVPGEVEM VKGQPFDVGP RYTQLQYIGE GAYGMVSSAY

61 DHVRKTRVAI KKISPFEHQT YCQRTLREIQ ILLRFRHENV IGIRDILRAS TLEAMRDVYI

121 VQDLMETDLY KLLKSQQLSN DHICYFLYQI LRGLKYIHSA NVLHRDLKPS NLLINTTCDL

181 KICDFGLARI ADPEHDHTGF LTEYVATRWY RAPEIMLNSK GYTKSIDIWS VGCILAEMLS

241 NRPIFPGKHY LDQLNHILGI LGSPSQEDLN CIINMKARNY LQSLPSKTKV AWAKLFPKSD

301 SKALDLLDRM LTFNPNKRIT VEEALAHPYL EQYYDPTDEP VAEEPFTFAM ELDDLPKERL

361 KELIFQETAR FQPGVLEAP
```

In certain embodiments, the ERK1 comprises the following nucleotide sequence, the coding region is bold and underlined (NCBI Accession No: X60188.1 (SEQ ID NO: 4), incorporated herein by reference in its entirety):

```
  1 cgttcctcgg cgccgccggg gccccagagg gcagcggcag caacagcagc agcagcagca 61 gcgggagtgg agatggcggc ggcggcggct caggggggcg ggggcgggga gccccgtaga 121 accgaggggg tcggcccggg ggtcccgggg gaggtggaga tggtgaaggg gcagccgttc 181 gacgtggggcc cgcgctacac gcagttgcag tacatcggcg agggcgcgta cggcatggtc 241 agctcggcct atgaccacgt gcgcaagact cgcgtggcca tcaagaagat cagcccttc 301 gaacatcaga cctactgcca gcgcacgctc cgggagatcc agatcctgct cgcttccgc 361 catgagaatg tcatcggcat ccgagacatt ctgcgggcgt ccaccctgga agccatgaga
```

```
 421 gatgtctaca ttgtgcagga cctgatggag actgacctgt acaagttgct gaaaagccag 481 cagctgagca atgaccatat ctgctacttc ctctaccaga tcctgcgggg cctcaagtac 541 atccactccg ccaacgtgct ccaccgagat ctaaagccct ccaacctgct cagcaacacc 601 acctgcgacc ttaagatttg tgatttcggc ctggcccgga ttgccgatcc tgagcatgac 661 cacaccggct tcctgacgga gtatgtggct acgcgctggt accgggcccc agagatcatg 721 ctgaactcca agggctatac caagtccatc gacatctggt ctgtgggctg cattctggct 781 gagatgctct ctaaccggcc catcttccct ggcaagcact acctggatca gctcaaccac 841 attctgggca tcctgggctc cccatcccag gaggacctga attgtatcat caacatgaag 901 gcccgaaact acctacagtc tctgccctcc aagaccaagg tggcttgggc caagcttttc 961 cccaagtcag actccaaagc ccttgacctg ctggaccgga tgttaacctt taaccccaat 1021 aaacggatca cagtggagga agcgctggct cacccctacc tggagcagta ctatgacccg 1081 acggatgagc cagtggccga ggagcccttc accttcgcca tggagctgga tgacctacct 1141 aaggagcggc tgaaggagct catcttccag agacagcac gcttccagcc cggagtgctg 1201 gaggcccct ag cccagaca gacatctctg cacctggg cctggacctg cctcctgcct 1261 gccctctcc cgccagactg ttagaaaatg gacactgtgc ccagcccgga ccttggcagc 1321 ccaggccggg gtggagcatg ggcctggcca cctctctcct ttgctgaggc ctccagcttc 1381 aggcaggcca aggccttctc ctccccaccc gccctcccca cggggcctcg ggagctcagg 1441 tggccccagt tcaatctccc gctgctgctg ctgctgcgcc cttaccttcc ccagcgtccc 1501 agtctctggc agttctggaa tggaagggtt ctggctgccc caacctgctg aagggcagag 1561 gtggagggtg gggggcgctg agtagggact cagggccatg cctgcccccc tcatctcatt 1621 caaccccac cctagtttcc ctgaaggaac attccttagt ctcaagggct agcatccctg 1681 aggagccagg ccgggccgaa tcccctccct gtcaaagctg tcacttcgcg tgccctcgct 1741 gcttctgtgt gtggtgagca gaagtggagc tgggggggcgt ggagagcccg cgcccctgc 1801 cacctccctg acccgtctaa tatataaata tagagatgtg tctatggctg aaaaaaaaaa 1861 aaaaaa
```

In certain embodiments, ERK2 comprises the following amino acid sequence (NCBI Accession No: P28482.3 (SEQ ID NO: 5), incorporated herein by reference in its entirety):

```
  1 MAAAAAAGAG PEMVRGQVFD VGPRYTNLSY IGEGAYGMVC SAYDNVNKVR VAIKKISPFE

61 HQTYCQRTLR EIKILLRFRH ENIIGINDII RAPTIEQMKD VYIVQDLMET DLYKLLKTQH

121 LSNDHICYFL YQILRGLKYI HSANVLHRDL KPSNLLLNTT CDLKICDFGL ARVADPDHDH

181 TGFLTEYVAT RWYRAPEIML NSKGYTKSID IWSVGCILAE MLSNRPIFPG KHYLDQLNHI

241 LGILGSPSQE DLNCIINLKA RNYLLSLPHK NKVPWNRLFP NADSKALDLL DKMLTFNPHK

301 RIEVEQALAH PYLEQYYDPS DEPIAEAPFK FDMELDDLPK EKLKELIFEE TARFQPGYRS
```

In certain embodiments, the ERK2 comprises the following nucleotide sequence, the coding sequence is bold and underlined (NCBI Accession No: NM_138957.3 (SEQ ID NO: 6), incorporated herein by reference in its entirety):

```
  1 gcccctccct ccgcccgccc gccggccgc ccgtcagtct ggcaggcagg caggcaatcg 61 gtccgagtgg ctgtcggctc ttcagctctc ccgctcggcg tcttccttcc tcctcccggt 121 cagcgtcggc ggctgcaccg gcggcggcgc agtccctgcg ggaggggcga caagagctga 181 gcggcggccg ccgagcgtcg agctcagcgc ggcggaggcg gcggcggccc ggcagccaac
```

-continued

```
 241 atggcggcgg cggcggcggc gggcgcgggc ccggagatgg tccgcgggca ggtgttcgac 301 gtggggccgc gctacaccaa cctctcgtac atcggcgagg gcgcctacgg catggtgtgc 361 tctgcttatg ataatgtcaa caaagttcga gtagctatca agaaaatcag ccccttgag 421 caccagacct actgccagag aaccctgagg gagataaaaa tcttactgcg cttcagacat 481 gagaacatca ttggaatcaa tgacattatt cgagcaccaa ccatcgagca aatgaaagat 541 gtatatatag tacaggacct catggaaaca gatctttaca agctcttgaa gacacaacac 601 ctcagcaatg accatatctg ctattttctc taccagatcc tcagagggtt aaaatatatc 661 cattcagcta acgttctgca ccgtgacctc aagccttcca acctgctgct caacaccacc 721 tgtgatctca agatctgtga ctttggcctg gcccgtgttg cagatccaga ccatgatcac 781 acagggttcc tgacagaata tgtggccaca cgttggtaca gggctccaga aattatgttg 841 aattccaagg gctacaccaa gtccattgat atttggtctg taggctgcat tctggcagaa 901 atgctttcta acaggcccat ctttccaggg aagcattatc ttgaccagct gaaccacatt 961 ttgggtattc ttggatcccc atcacaagaa gacctgaatt gtataataaa tttaaaagct 1021 aggaactatt tgctttctct tccacacaaa aataaggtgc catgaacag gctgttccca 1081 aatgctgact ccaaagctct ggacttattg gacaaaatgt tgacattcaa cccacacaag 1141 aggattgaag tagaacaggc tctggcccac ccatatctgg agcagtatta cgacccgagt 1201 gacgagccca tcgccgaagc accattcaag ttcgacatgg aattggatga cttgcctaag 1261 gaaaagctca aagaactaat ttttgaagag actgctagat tccagccagg atacagatct 1321 taaatttgtc aggtacctgg agtttaatac agtgagctct agcaagggag gcgctgcctt 1381 ttgtttctag aatattatgt tcctcaaggt ccattatttt gtattctttt ccaagctcct 1441 tattggaagg tatttttta aatttagaat taaaaattat ttagaaagtt acatataaaa 1501 aaaaaaaaaa aaaa
```

In certain embodiments, the disclosure provides methods for treating vasculopathies (e.g., vEDS) in a subject in need thereof, the methods comprising administering to the subject a pharmaceutical composition comprising a therapeutically effective amount of an agent that decreases the activity or expression of ERK. Examples of ERK inhibitors include ASN007 (Asana BioSciences, Bridgewater, New Jersey), Ulixertinib (BVD-523) (BioMed Valley Discoveries, Kansas City, MO), CC-90003 (Celgene Corporation, Summit, New Jersey), GDC-0994 (Array BioPharma, Boulder, CO), KO-947 (Kura Oncology, San Diego, California), LTT462 (Novartis, Basel, Switzerland), LY3214996 (Eli Lilly and Company, Indianapolis, IN), MK-8353 (Merck Sharp and Dohme Corp, Kenilworth, NJ).

MEK Inhibitors

In embodiments, the disclosure provides methods for treating vasculopathies (e.g., vEDS) in a subject in need thereof, the methods comprising administering to the subject a pharmaceutical composition comprising a therapeutically effective amount of an agent that decreases the activity or expression of ERK or PKC. For example, a Ras/Raf/MEK/ERK pathway inhibitor. In embodiments, the Ras pathway inhibitor is selected from a Raf inhibitor such as vemurafenib, sorafenib, or dabrafenib, a MEK inhibitor such as AZD6244 (Selumetinib), PD0325901, GSK1120212 (Trametinib), U0126-EtOH, PD184352, RDEA119 (Rafametinib), PD98059, BIX 02189, MEK162 (Binimetinib), AS-703026 (Pimasertib), SL-327, BIX02188, AZD8330, TAK-733, cobimetinib or PD318088, and an ERK inhibitor such as LY3214996, BVD-523 or GDC-0994.

In embodiments, the MEK inhibitor is selected from the group consisting of Trametinib, Refametinib, Cobimetinib, TAK-733, PD0325901, PD184352 (CI-10-40), R05126766, RO-4987655; E6201; GDC-0623; CH5126766; G-573; WX-554; Selumetinib, Binimetinib and Pimasertib. In embodiments, the MEK inhibitor comprises cobimetinib. In embodiments, the MEK inhibitor comprises trametinib. In embodiments, the MEK inhibitor comprises trametinib and cobimetinib. In embodiments the MEK inhibitors, or pharmaceutically acceptable salts thereof are also contemplated herewith.

In certain embodiments, the MEK inhibitor can be administered in a concentration from about 0.001 mg/kg to about 250 mg/kg body weight, e.g., 0.001 mg/kg, 0.05 mg/kg 0.01 mg/kg, 0.05 mg/kg, 1 mg/kg, 5 mg/kg, 10 mg/kg, 25 mg/kg, 50 mg/kg, 75 mg/kg, 100 mg/kg, 125 mg/kg, 150 mg/kg, 175 mg/kg, 200 mg/kg, 225 mg/kg, or 250 mg/kg body weight.

Protein Kinase C (PKC) Inhibitors

Protein kinase C, commonly abbreviated to PKC, is a family of protein kinase enzymes that are involved in controlling the function of other proteins through the phosphorylation of hydroxyl groups of serine and threonine amino acid residues on these proteins, or a member of this family. PKC enzymes in turn are activated by signals such as increases in the concentration of diacylglycerol (DAG) or calcium ions ($Ca^{2+}$). Thus, PKC enzymes play important roles in several signal transduction cascades. The PKC family consists of fifteen isozymes in humans, and are divided into three subfamilies, based on their second messenger requirements: conventional (or classical), novel, and atypical. Conventional PKCs contain the isoforms α, $β_I$, $β_{II}$, and γ. These require $Ca^{2+}$, DAG, and a phospholipid such as phosphatidylserine for activation. Novel (n) PKCs include the δ, ε, η, and θ isoforms, and require DAG, but do not require $Ca^{2+}$ for activation. Thus, conventional and novel PKCs are activated through the same signal transduction pathway as phospholipase C. On the other hand, atypical (a) PKCs (including protein kinase Mζ and ι/λ isoforms) require neither $Ca^{2+}$ nor diacylglycerol for activation. The term "protein kinase C" as used herein generally refers to the entire family of isoforms.

Exemplary PKC agents include, but are not limited to ruboxistaurin, chelerythrine, miyabenol C, myricitrin, gossypol, verbascoside, BIM-1, or Bryostatin 1. In embodiments, the PKC inhibitor comprises enzastaurin. In embodiments, the PKC inhibitor comprises ruboxistaurin. In embodiments, the PKC agents, or pharmaceutically acceptable salts thereof are also contemplated herewith.

In some embodiments, the PKC inhibitor may have the structure of:

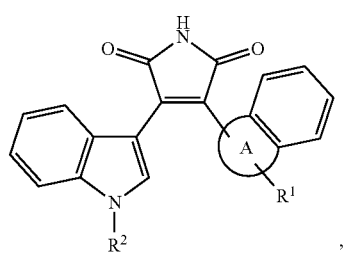

(I)

or a salt thereof,
wherein:
Ring A is a substituted or unsubstituted $C_5$-$C_6$cycloalkyl, substituted or unsubstituted 5 to 6 membered heterocycloalkyl and having oe more more N, O or S ring members, substituted or unsubstituted phenyl, or substituted or unsubstituted 5 to 6 membered heteroaryl and having oe more more N, O or S ring members;

each $R^1$ and $R^2$ is independently hydrogen, halogen, —$N_3$, —CN, —$NO_2$, —$NR^AR^B$, —$C(O)R^C$, —$C(O)$—$OR^C$, —$C(O)NR^AR^B$, —$OR^D$, —$NR^AC(O)R^C$, —$NR^AC(O)OR^C$, substituted or unsubstituted alkyl (e.g., $C_1$-$C_2$, $C_1$-$C_4$, $C_1$-$C_8$, or $C_1$-$C_{10}$) substituted or unsubstituted heteroalkyl (e.g., 2 to 8 membered, 2 to 6 membered, 4 to 6 membered, 2 to 3 membered, or 4 to 5 membered having one or more N, O or S ring members), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered having one or more N, O or S ring members), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered having one or more N, O or S ring members); or $R^1$ and $R^2$ are connected together to form a substituted or unsubstituted alkylene (e.g., $C_1$-$C_2$, $C_1$-$C_4$, $C_1$-$C_8$, $C_1$-$C_{10}$), or substituted or unsubstituted heteroalkylene (e.g., 2 to 8 membered, 2 to 6 membered, 4 to 6 membered, 2 to 3 membered, or 4 to 5 membered having or more N, O or S in the heteroalkylene chain), substituted or unsubstituted cycloalkylene (e.g., $C_3$-$C_8$, $C_3$-$C_6$, $C_4$-$C_6$, or $C_5$-$C_6$), substituted or unsubstituted heterocycloalkylene (e.g., 3 to 8 membered, 3 to 6 membered, 4 to 6 membered, 4 to 5 membered, or 5 to 6 membered having one or more N, O or S ring members)), substituted or unsubstituted arylene (e.g., $C_6$-$C_{10}$ or phenylene), or substituted or unsubstituted heteroarylene (e.g., 5 to 10 membered, 5 to 9 membered, or 5 to 6 membered having one or more N, O or S ring members)) linker;

wherein each $R^A$, $R^B$, $R^C$, and $R^D$ at each occurrence is independently hydrogen, substituted or unsubstituted alkyl, substituted or unsubstituted heteroalkyl (e.g. 2 to 8 membered with one or more N, O or S atoms), substituted or unsubstituted cycloalkyl (e.g. 2 to 3 membered), substituted or unsubstituted heterocycloalkyl ((e.g., 3 to 8 membered with one or more N, O or S ring members), substituted or unsubstituted aryl such as phenyl, or substituted or unsubstituted heteroaryl (e.g. e.g., 5 to 10 membered, with one or more N, O or S ring members).

In some embodiments, the Ring A is 5-6 membered heteroaryl that may include one or more nitrogens as ring members.

In some embodiments, the PKC inhibitor may have the structure of:

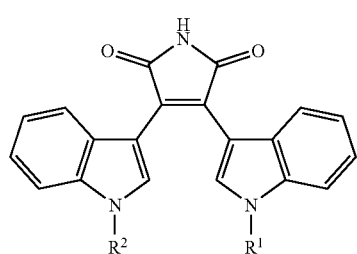

(II)

$R^1$ and $R^2$ are as described above.

In some embodiments, the PKC inhibitor may have the structure of:

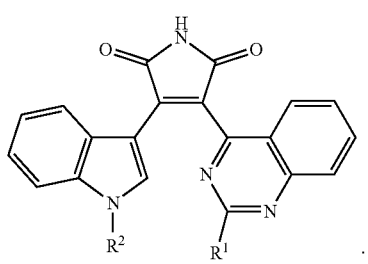

(III)

$R^1$ and $R^2$ are as described above.

In some embodiments, the PKC inhibitor may have the structure of:

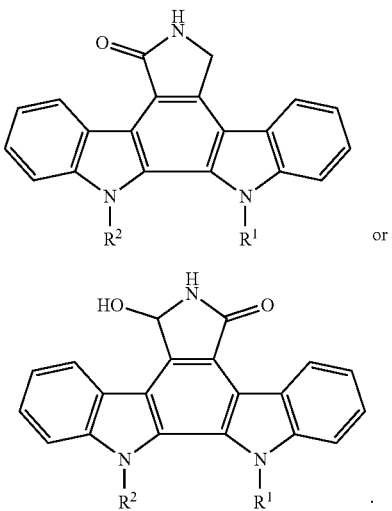

(IV-A)

or (IV-B)

$R^1$ and $R^2$ are as described above.

In some embodiments, for the PKC inhibitor of formula (I), (II), (III), (IV-A) or (IV-B), each $R^1$ and $R^2$ is hydrogen, substituted or unsubstituted $C_1$-$C_4$ alkyl, substituted or unsubstituted 2 to 6 membered heteroalkyl (e.g. having one or more N, O or S members), substituted or unsubstituted $C_3$-$C_6$ cycloalkyl, substituted or unsubstituted 5 to 10 membered heterocycloalkyl (e.g. having one or more N, O or S ring members), substituted or unsubstituted phenyl, or substituted or unsubstituted 5 to 10 membered heteroaryl (e.g. having one or more N, O or S ring members). In some embodiments, each $R^1$ and $R^2$ is independently hydrogen, substituted or unsubstituted $C_1$-$C_4$ alkyl, or substituted heterocycloalkyl having oe more more N, O or S ring membera. In some embodiments, each $R^1$ and $R^2$ is independently hydrogen, or unsubstituted $C_1$-$C_4$ alkyl.

In some embodiments, for the PKC inhibitor of formula (II), $R^1$ is substituted or unsubstituted piperidinyl, piperazinyl, pyridyl, or pyrimidyl. For example, $R^1$ is

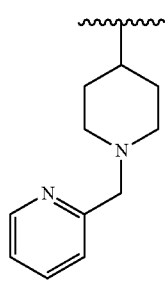

In some embodiments, $R^2$ is hydrogen or unsubstituted $C_1$-$C_4$ alkyl. In some embodiments, $R^2$ is hydrogen. In some embodiments, $R^2$ is methyl. In some embodiments, $R^2$ is ethyl. In some embodiments, $R^2$ is propyl. In embodiment, $R^2$ is butyl. In some embodiments, $R^2$ is t-butyl.

In some embodiments, for the PKC inhibitor of formula (I), (II), (III), (IV-A) or (IV-B), $R^1$ and $R^2$ are connected to each other to form a substituted or unsubstituted $C_1$-$C_8$ alkylene, or substituted or unsubstituted 2 to 8 membered heteroalkylene linker having one or more N, O or S atoms in the heteroalkylene chain. In some embodiments, $R^1$ and $R^2$ are connected to each other to form a substituted or unsubstituted $C_1$-$C_8$ alkylene linker. In some embodiments, $R^1$ and $R^2$ are connected to each other to form a substituted $C_1$-$C_8$ alkylene linker. In some embodiments, $R^1$ and $R^2$ are connected to each other to form an unsubstituted $C_1$-$C_8$ alkylene linker. In some embodiments, $R^1$ and $R^2$ are connected to each other to form 2 to 8 membered heteroalkylene linker having one or more N, O or S atoms in the heteroalkylene chain. In some embodiments, $R^1$ and $R^2$ are connected to each other to form unsubstituted 2 to 8 membered heteroalkylene linker having one or more N, O or S atoms in the heteroalkylene linker chain.

In some embodiments, $R^1$ and $R^2$ are connected to each other to form

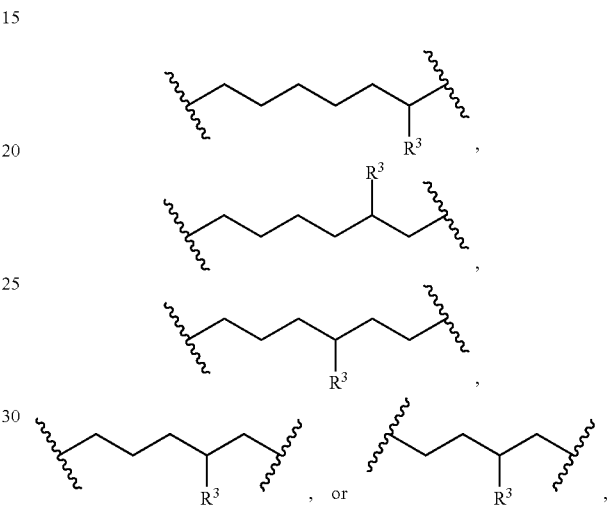

wherein $R^3$ is hydrogen, halogen, —$N_3$, —CN, —$NO_2$, —$NR^AR^B$, —$C(O)R^C$, —$C(O)$—$OR^C$, —$C(O)NR^AR^B$, —$OR^D$, —$NR^AC(O)R^C$, —$NR^AC(O)OR^C$, substituted or unsubstituted alkyl (e.g., $C_1$-$C_2$, $C_1$-$C_4$, $C_1$-$C_8$, or $C_1$-$C_{10}$) substituted or unsubstituted heteroalkyl (e.g., 2 to 8 membered, 2 to 6 membered, 4 to 6 membered, 2 to 3 membered, or 4 to 5 membered having one or more N, O or S members), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered and having one or more N, O or S ring members), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered and having one or more N, O or S ring members). $R^A$, $R^B$, $R^C$, and $R^D$ are described as above.

In some embodiments, $R^1$ and $R^2$ are connected to each other to form

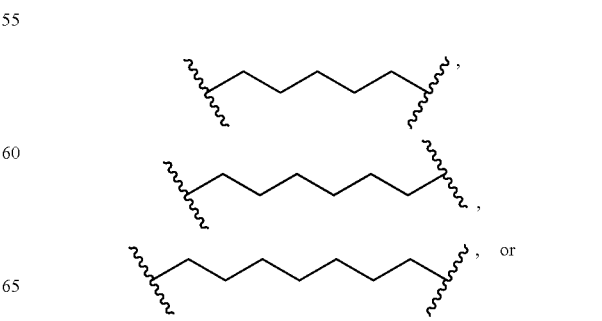

-continued

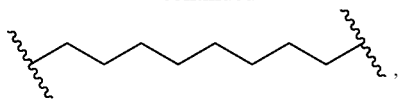

which may be substituted with one or more of R³ described above.

In some embodiments, R¹ and R² are connected to each other to form

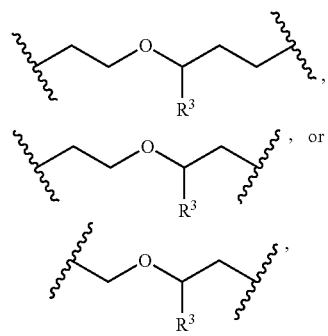

R³ is described as above.

In some embodiments, R¹ and R² are connected to each other to form

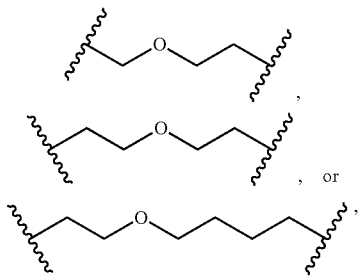

which may be substituted with one or more of R³ described above.

In some embodiments, for the PKC inhibitor of formula (IV-A) or (IV-B), R¹ and R² are connected to each other to form substituted or unsubstituted $C_5$-$C_6$ cycloalkylene linker.

In some embodiments, R¹ and R² are connected to each other to form substituted $C_5$-$C_6$ cycloalkylene linker, for example, which may be substituted with one or more R³ described above. In some embodiments, R¹ and R² are connected to each other to form unsubstituted $C_5$-$C_6$ cycloalkylene linker.

In some embodiments, R¹ and R² are connected to each other to form substituted or unsubstituted 5 to 6 membered heterocycloalkylene linker (e.g. having one or more N, O or S atoms in the linker chain). In some embodiments, R¹ and R² are connected to each other to form substituted 5 to 6 membered heterocycloalkylene linker having one or more N, O or S atoms in the linker chain, for example, which may be substituted with R³ described above. In some embodiments, R¹ and R² are connected to each other to form unsubstituted 5 to 6 membered heterocycloalkylene linker having one or more N, O or S atoms in the linker chain.

In some embodiments, R¹ and R² are connected to each other to form

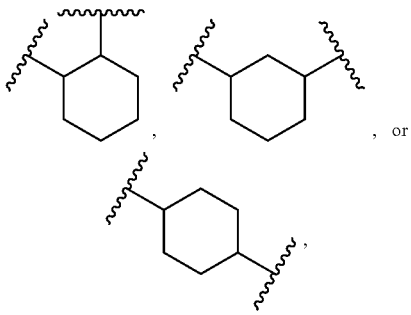

which may be substituted with one or more of R³ described above. In some embodiments, R¹ and R² are connected to each other to form

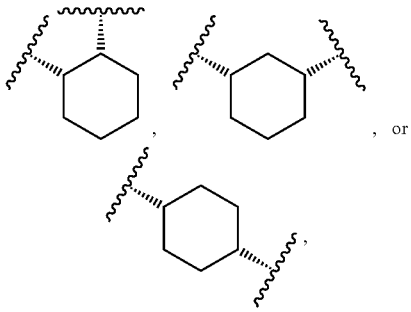

which may be substituted with one or more of R³ described above. In some embodiments, R¹ and R² are connected to each other to form

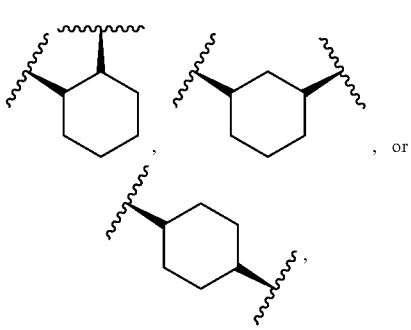

which may be substituted with one or more of R³ described above.

In some embodiments, R¹ and R² are connected to each other to form

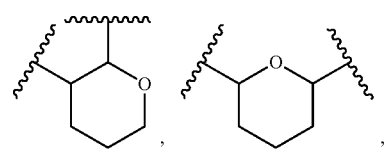

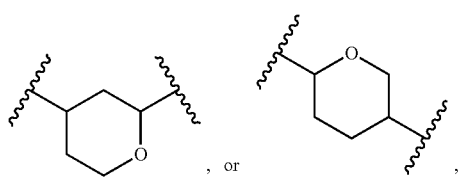

, or which may be substituted with one or more of $R^3$ described above. In some embodiments, $R^1$ and $R^2$ are connected to each other to form

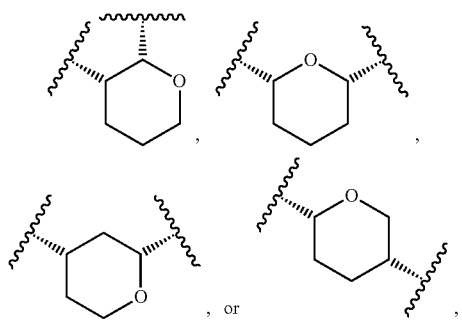

, or which may be substituted with one or more of $R^3$ described above. In some embodiments, $R^1$ and $R^2$ are connected to each other to form

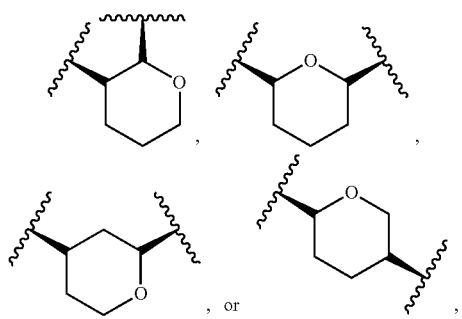

, or which may be substituted with one or more of $R^3$ described above.

In some embodiments, for the PKC inhibitor of formula (III), each $R^1$ and $R^2$ is independently hydrogen, substituted or unsubstituted $C_1$-$C_4$ alkyl, or substituted or unsubstituted 5 to 6 membered heterocycloalkyl and having one or more N, O or S ring members. In some embodiments, $R^1$ is unsubstituted $C_1$-$C_4$ alkyl. In some embodiments, $R^1$ is substituted 5 to 6 membered heterocycloalkyl having one or more N, O or S ring members, which may be substituted one or more of $R^3$ described above. In some embodiments, $R^1$ is substituted 5 to 6 membered heterocycloalkyl having one or more N, O or S ring members, which may be substituted one or more of $R^3$ described above. In some embodiment, $R^1$ is substituted or unsubstituted piperidinyl or piperazinyl. In some embodiment, $R^1$ is substituted piperidinyl or piperazinyl, which may be substituted one or more of $R^3$ described above. In some embodiment, $R^1$ is unsubstituted piperidinyl or piperazinyl. In some embodiments, $R^1$

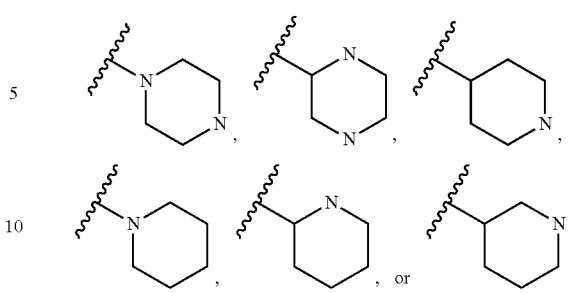

, or which may be substituted with one or more of $R^3$ described above. In some embodiments, $R^1$ is

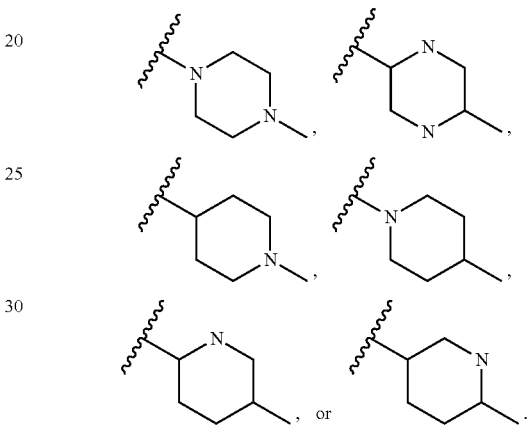

, or

In some embodiments, $R^2$ is hydrogen. In embodiment, $R^2$ is methyl.

As discussed above, group that are "substituted" are substituted by other than hydrogen at one or more available positions, typically 1, 2, 3, 4 or 5 positions, by one or more suitable groups (which may be the same or different), for example, halogen, cyano, amino, hydroxy, nitro, azido, carboxamido, —COOH, $SO_2NH_2$, alkyl (e.g., $C_1$-$C_8$alkyl), alkenyl (e.g., $C_2$-$C_8$alkenyl), alkynyl (e.g., $C_2$-$C_8$alkynyl), alkoxy (e.g., $C_1$-$C_8$alkoxy), alkyl ether (e.g., $C_2$-$C_8$alkyl ether), alkylthio (e.g., $C_1$-$C_8$alkylthio), mono- or di-($C_1$-$C_8$alkyl)amino, haloalkyl (e.g., $C_1$-$C_6$haloalkyl), hydroxyalkyl (e.g., $C_1$-$C_6$hydroxyalkyl), aminoalkyl (e.g., $C_1$-$C_6$aminoalkyl), haloalkoxy (e.g., $C_1$-$C_6$haloalkoxy), alkanoyl (e.g., $C_1$-$C_8$alkanoyl), alkanone (e.g., $C_1$-$C_8$alkanone), alkanoyloxy (e.g., $C_1$-$C_8$alkanoyloxy), alkoxycarbonyl (e.g., $C_1$-$C_8$alkoxycarbonyl), mono- and di-($C_1$-$C_8$alkyl)amino, mono- and di-($C_1$-$C_8$alkyl)amino$C_1$-$C_8$alkyl, mono- and di-($C_1$-$C_8$alkyl)carboxamido, mono- and di-($C_1$-$C_8$alkyl)sulfonamido, alkylsulfinyl (e.g., $C_1$-$C_8$alkylsulfinyl), alkylsulfonyl (e.g., $C_1$-$C_8$alkylsulfonyl), aryl (e.g., phenyl), arylalkyl (e.g., ($C_6$-$C_{18}$aryl)$C_1$-$C_8$alkyl, such as benzyl and phenethyl), aryloxy (e.g., $C_6$-$C_{18}$aryloxy such as phenoxy), arylalkoxy (e.g., ($C_6$-$C_{18}$aryl)$C_1$-$C_8$alkoxy) and/or 3- to 8-membered heterocyclic groups having one or more N, O or S ring members.

As referred to herein, a group having a specified number of "members or "membered" refers to a specified number of atoms of the group.

Exemplary PKC inhibitors may include

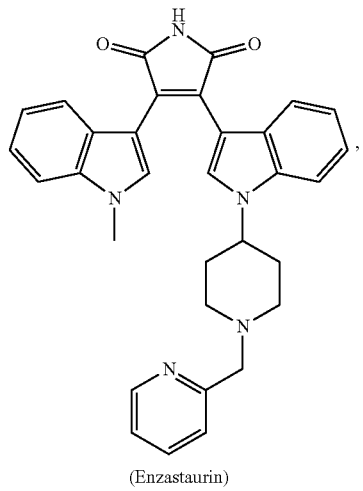
(Enzastaurin)

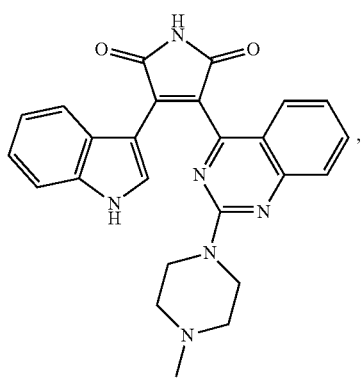
(Sotrastaurin)

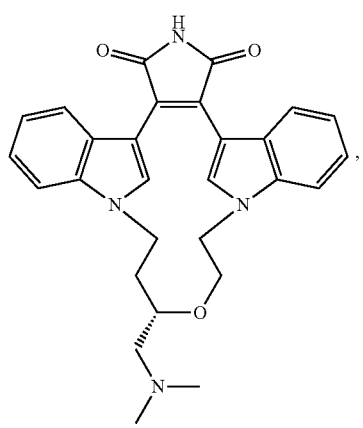
(Ruboxistaurin)

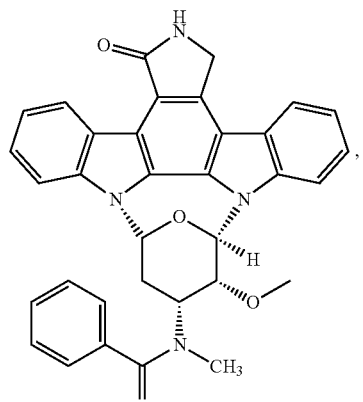

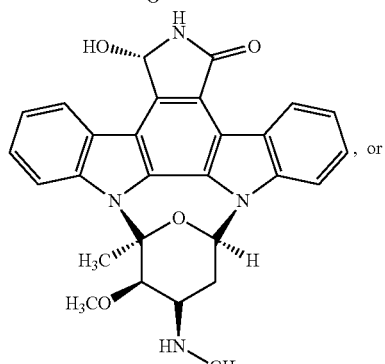
, or

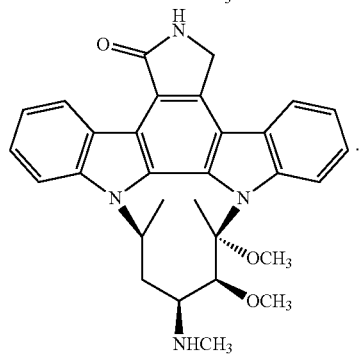

In certain embodiments, a protein kinase inhibitor or a monoclonal antibody that inhibits receptors involved in protein kinase or growth factor signaling pathways such as an EGFR, VEGFR, AKT, Erb1, Erb2, ErbB, Syk, Bcr-Abl, JAK, Src, GSK-3, PI3K, Ras, Raf, MAPK, MAPKK, mTOR, c-Kit, eph receptor or BRAF inhibitors is administered to a subject. Nonlimiting examples of protein kinase or growth factor signaling pathways inhibitors include Afatinib, Axitinib, Bevacizumab, Bosutinib, Cetuximab, Crizotinib, Dasatinib, Erlotinib, Fostamatinib, Gefitinib, Imatinib, Lapatinib, Lenvatinib, Mubritinib, Nilotinib, Panitumumab, Pazopanib, Pegaptanib, Ranibizumab, Ruxolitinib, Saracatinib, Sorafenib, Sunitinib, Trastuzumab, Vandetanib, AP23451, Vemurafenib, MK-2206, GSK690693, A-443654, VQD-002, Miltefosine, Perifosine, CAL101, PX-866, LY294002, rapamycin, temsirolimus, everolimus, ridaforolimus, Alvocidib, Genistein, Selumetinib, AZD-6244, Vatalanib, P1446A-05, AG-024322, ZD1839, P276-00, GW572016 or a mixture thereof.

In certain embodiments, the agent that decreases the activity or expression of PKC can be administered in a concentration from about 0.001 mg/kg to about 250 mg/kg body weight, e.g., 0.001 mg/kg, 0.05 mg/kg 0.01 mg/kg, 0.05 mg/kg, 1 mg/kg, 5 mg/kg, 10 mg/kg, 25 mg/kg, 50 mg/kg, 75 mg/kg, 100 mg/kg, 125 mg/kg, 150 mg/kg, 175 mg/kg, 200 mg/kg, 225 mg/kg, or 250 mg/kg body weight.

In certain embodiments, PKC comprises the following amino acid sequence (NCBI Accession No: NP_002728.1 (SEQ ID NO: 7), incorporated herein by reference in its entirety):

```
  1 MADVFPGNDS TASQDVANRF ARKGALRQKN VHEVKDHKFI ARFFKQPTFC SHCTDFIWGF
 61 GKQGFQCQVC CFVVHKRCHE FVTFSCPGAD KGPDTDDPRS KHKFKIHTYG SPTFCDHCGS
121 LLYGLIHQGM KCDTCDMNVH KQCVINVPSL CGMDHTEKRG RIYLKAEVAD EKLHVTVRDA
181 KNLIPMDPNG LSDPYVKLKL IPDPKNESKQ KTKTIRSTLN PQWNESFTFK LKPSDKDRRL
241 SVEIWDWDRT TRNDFMGSLS FGVSELMKMP ASGWYKLLNQ EEGEYYNVPI PEGDEEGNME
301 LRQKFEKAKL GPAGNKVISP SEDRKQPSNN LDRVKLTDFN FLMVLGKGSF GKVMLADRKG
361 TEELYAIKIL KKDVVIQDDD VECTMVEKRV LALLDKPPFL TQLHSCFQTV DRLYFVMEYV
421 NGGDLMYHIQ QVGKFKEPQA VFYAAEISIG LFFLHKRGII YRDLKLDNVM LDSEGHIKIA
481 DFGMCKEHMM DGVTTRTFCG TPDYIAPEII AYQPYGKSVD WWAYGVLLYE MLAGQPPFDG
541 EDEDELFQSI MEHNVSYPKS LSKEAVSICK GLMTKHPAKR LGCGPEGERD VREHAFFRRI
601 DWEKLENREI QPPFKPKVCG KGAENFDKFF TRGQPVLTPP DQLVIANIDQ SDFEGFSYVN
661 PQFVHPILQS AV
```
25

In certain embodiments, the PKC comprises the following nucleotide sequence, the coding sequence is bold and underlined (NCBI Accession No: NM_002737.2 (SEQ ID NO: 8), incorporated herein by reference in its entirety):

```
   1 ggccgcagct ccccggcgga ggcaagaggt ggttgggggg gaccatggct gacgttttcc
  61 cgggcaacga ctccacggcg tctcaggacg tggccaaccg cttcgcccgc aaaggggcgc
 121 tgaggcagaa gaacgtgcac gaggtgaagg accacaaatt catcgcgcgc ttcttcaagc
 181 agcccacctt ctgcagccac tgcaccgact tcatctgggg gtttgggaaa caaggcttcc
 241 agtgccaagt ttgctgtttt gtggtccaca agaggtgcca tgaatttgtt acttttctct
 301 gtccgggtgc ggataaggga cccgacactg atgacccag gagcaagcac aagttcaaaa
 361 tccacactta cggaagcccc accttctgcg atcactgtgg gtcactgctc tatggactta
 421 tccatcaagg gatgaaatgt gacacctgcg atatgaacgt tcacaagcaa tgcgtcatca
 481 atgtccccag cctctgcgga atggatcaca ctgagaagag ggggcggatt tacctaaagg
 541 ctgaggttgc tgatgaaaag ctccatgtca cagtacgaga tgcaaaaaat ctaatcccta
 601 tggatccaaa cgggctttca gatccttatg tgaagctgaa acttattcct gatcccaaga
 661 atgaaagcaa gcaaaaaacc aaaaccatcc gctccacact aaatccgcag tggaatgagt
 721 cctttacatt caaattgaaa ccttcagaca agaccgacg actgtctgta gaaatctggg
 781 actgggatcg aacaacaagg aatgacttca tgggatccct ttccttttgga gtttcggagc
 841 tgatgaagat gccggccagt ggatggtaca agttgcttaa ccaagaagaa ggtgagtact
 901 acaacgtacc cattccggaa ggggacgagg aaggaaacat ggaactcagg cagaaattcg
 961 agaaagccaa acttggccct gctggcaaca aagtcatcag tccctctgaa gacaggaaac
1021 aaccttccaa caaccttgac cgagtgaaac tcacggactt caatttcctc atggtgttgg
1081 gaaaggggag ttttggaaag gtgatgcttg ccgacaggaa gggcacagaa gaactgtatg
1141 caatcaaaat cctgaagaag gatgtggtga ttcaggatga tgacgtggag tgcaccatgg
1201 tagaaaagcg agtcttggcc ctgcttgaca acccccgtt cttgacgcag ctgcactcct
1261 gcttccagac agtggatcgg ctgtacttcg tcatggaata tgtcaacggt ggggacctca
```

-continued

```
1321  tgtaccacat tcagcaagta ggaaaattta aggaaccaca agcagtattc tatgcggcag
1381  agatttccat cggattgttc tttcttcata aaagaggaat catttatagg gatctgaagt
1441  tagataacgt catgttggat tcagaaggac atatcaaaat tgctgacttt gggatgtgca
1501  aggaacacat gatggatgga gtcacgacca ggaccttctg tgggactcca gattatatcg
1561  ccccagagat aatcgcttat cagccgtatg gaaaatctgt ggactggtgg gcctatggcg
1621  tcctgttgta tgaaatgctt gccgggcagc ctccatttga tggtgaagat gaagacgagc
1681  tatttcagtc tatcatggag cacaacgttt cctatccaaa atccttgtcc aaggaggctg
1741  tttctatctg caaaggactg atgaccaaac acccagccaa gcggctgggc tgtgggcctg
1801  aggggggagag ggacgtgaga gagcatgcct tcttccggag gatcgactgg gaaaaactgg
1861  agaacaggga gatccagcca ccattcaagc ccaaagtgtg tggcaaagga gcagagaact
1921  ttgacaagtt cttcacacga ggacagcccg tcttaacacc acctgatcag ctggttattg
1981  ctaacataga ccagtctgat tttgaagggt tctcgtatgt caaccccag tttgtgcacc
2041  ccatcttaca gagtgcagta tgaaactcac cagcgagaac aaacacctcc ccagccccca
2101  gccctccccg cagtgggaag tgaatcctta accctaaaat tttaaggcca cggccttgtg
2161  tctgattcca tatggaggcc tgaaaattgt agggttatta gtccaaatgt gatcaactgt
2221  tcagggtctc tctcttacaa ccaagaacat tatcttagtg gaagatggta cgtcatgctc
2281  agtgtccagt ttaattctgt agaagttacg tctggctcta ggttaaccct tcctagaaag
2341  caagcagact gttgccccat tttgggtaca atttgatata cttccatac cctccatctg
2401  tggatttttc agcattggaa tcccccaacc agagatgtta aagtgagcct gtcccaggaa
2461  acatctccac ccaagacgtc tttggaatcc aagaacagga agccaagaga gtgagcaggg
2521  agggattggg ggtgggggag gcctcaaaat accgactgcg tccattctct gcctccatgg
2581  aaacagcccc tagaatctga aaggccggga taaacctaat cactgttccc aaacattgac
2641  aaatcctaac ccaaccatgg tccagcagtt accagtttaa acaaaaaaac ctcagatgag
2701  tgttgggtga atctgtcatc tggtaccctc cttggttgat aactgtcttg atacttttca
2761  ttctttgtaa gaggccaaat cgtctaagga cgttgctgaa caagcgtgtg aaatcatttc
2821  agatcaagga taagccagtg tgtacatatg ttcatttta tctctgggag attattttc
2881  catccagggt gccatcagta atcatgccac tactcaccag tgttgttcgc caacacccac
2941  ccccacacac accaacattt tgctgcctac cttgttatcc ttctcaagaa gctgaagtgt
3001  acgccctctc ccctttgtg cttatttatt taataggctg cagtgtcgct tatgaaagta
3061  cgatgtacag taacttaatg gaagtgctga ctctagcatc agcctctacc gattgatttt
3121  cctcccttct ctagccctgg atgtccactt agggataaaa agaatatggt tttggttccc
3181  atttctagtt cacgttgaat gacaggcctg gagctgtaga atcaggaaac ccggatgcct
3241  aacagctcaa agatgttttg ttaatagaag gatttttaata cgttttgcaa atgcatcatg
3301  caatgaattt tgcatgttta taataaacct taataacaag tgaatctata ttattgatat
3361  aatcgtatca agtataaaga gagtattata ataattttat aagcacacaat tgtgctctat
3421  ttgtgcaggt tcttgtttct aatcctcttt tctaattaag ttttagctga atcccttgct
3481  tctgtgcttt ccctcccctgc acatgggcac tgtatcagat agattacttt ttaaatgtag
3541  ataaaatttc aaaaatgaat ggctagttta cgtgatagat taggctctta ctacatatgt
3601  gtgtgtatat atatgtatt gattctacct gcaaacaaat ttttattggt gaggactatt
3661  tttgagctga cactccctct tagtttcttc atgtcacctt tcgtcctggt tcctccgcca
```

-continued

```
3721 ctcttcctct tggggacaac aggaagtgtc tgattccagt ctgcctagta cgttggtaca
3781 cacgtggcat tgccgcagca cctgggctga cctttgtgtg tgcgtgtgtg tgtgtttcct
3841 tcttcccttc agcctgtgac tgttgctgac tccaggggtg ggagggatgg ggagactccc
3901 ctcttgctgt gtgtactgga cacgcaggaa gcatgctgtc ttgctgcctc tgcaacgacc
3961 tgtcgtttgc tccagcatgc acaaacttcg tgagaccaac acagccgtgc cctgcaggca
4021 ccagcacgtg cttttcagag gctgcggact ttcttccagc cattgtggca ttggccttc
4081 cagtcttggg aggagcgcgc tgctttggtg agacaccccc atgcaaggtc ctcagagtag
4141 ccgggttcta ccacaaacag aaacagaatg aaagtagctg tcagtccttg tagagagccg
4201 ctctgtttcc tcccagaagc atctcccagc taagctcgca ttatttttct cctctggctg
4261 tttgcctgaa gttcacagaa cacacaacca tgaaaggctt tttgaggtga gaggcccagg
4321 tggtcctggc aaccctgagt agaaggagag acggggtagg gaacgggccc ggccagaaaa
4381 gaaccatttc ttctgccatc ttttatgcac catagacatc gagactccag ggggtcctgg
4441 ctcccctgtc cctgcagccc tgcaggtcag tgcatgatct gggttcgtgt cctgaccagg
4501 tgctcctcct ttgatccgag gggaaaggga ctggtttata gaaagagcct aggagacaaa
4561 agggccagtc cccctgccca gaatggagca gcagcaggac agaccccccac gaggcccccc
4621 agagaggagg aagatcccac ggaggaacac atgaggttag ggacccttgt tcagcacccc
4681 aaacagcctg cctgtttaaa gcaggcagca ggcttaggcc ttccctgcaa ccccaacacc
4741 cacaagtttg tttctctagg aaacacattc actgtctcag ctggctgtta ctctctcaga
4801 ccatatggca aagttttcca agaaaatgcc ccgacagggg tgcccagcac actgcctgag
4861 ggacaacaga catcagaaca aaccccccaga gagaaacagt caaaatcagg gcccggtgca
4921 gtgttgtcat gtggaacctg ctttatccat tgctgagtgt tgaatgtggg taatggttag
4981 ggcttccag atctcagcag ccaaagacag ttattgttgg aagactgtca tgtagataac
5041 catgagcaat ggctcgcctc agaatcagtt cataaaattc tatggtactg gccccttcgt
5101 gggtattgtg tgaaatgaga tggtggcgag gggtgcgctg tggaactgcc gcagccacgc
5161 aggaggtccc tggggggatgc tttgggaagt ccttgcccct gagcactgcc tgattgccag
5221 ggcctgtgga ggtctaggcc gcctggcaga atctagcacc gtccgaatcc ccgcaggacc
5281 catggagcta tgaccacacc aggccattca aatggctctg cattatcttc ccttggaagg
5341 tggccactcc tcggtggcag ggcctttccc tgaggctgca ggccgtgggc tggcagcccg
5401 tctcttggca tttcaattga aggtcaccag gtgctgggtt tgaaaggaag tcactggagt
5461 gctgccaggg gccgccctcc aaggttaatg agaggcccac atccaggcaa gaactaattc
5521 aaaaggcaga tcagaaacca caggagtcaa aattattgct ccggcagtgc ttcccttcct
5581 ttcatccact ggcctcgtgt ggtccatgca gggccactgt ctgcccttc tgatgccacg
5641 tattaggctt tcttactcag aattttgata gaaaaccatg gggcaagag ctctggaagc
5701 ctggccggaa agaccaaggt tcatgcagcc caacaaatga ttgttgagca cctctcggag
5761 ccaaagtcct taggcgagtg tggtgacttc ctggaaggag gatgcagact tccagagagc
5821 cccccccaacg gacgtgctga aagggagag ggaggcgggg gctgtagtca ggaaggagcc
5881 agagaagaac aggggtttggg tgcatccaga aatatgcctg cagtaggagg gagaggaagg
5941 ggtgccaccg tcaacggctt cccatcggag gtggttggtg cagatgaag tttctgtctg
6001 ctggccctca agagagtgtt ttgccaggga cacagtctgt tcctcctcag aaaacacccc
6061 ccaaatgcta acaacatccc caccagctgc tagaagcccc tttcccctcc ccaccttgaa
6121 gtagctcata gttctctggg cagagccaga ccatccagtg taccccagag gccagtaggt
```

-continued

```
6181 tcctgcccat tttcctctct ggcttcctgc caagaattat ggcagctgag gatgaatgga
6241 gaagtaaaaa caactaacac cgcacaacta acaactaaca ccgcagttcc cacctgggtt
6301 ccacttagca ggagacattt cggagggttt ttttgtttt tgttcctgtt tttttttttt
6361 ttgctggaat ttgttttctc agtactgaaa agagaaaaag tgacaatctt gtatttttaa
6421 aagcctcgga aaggtgatac catctgacag tcattttctc acgttggtct tctaaagtca
6481 cctatttctt gtgtgtgcac atcacaccat ttcctgtttc tttataaccc gacaagggta
6541 ggagtgcctg tttcccctgc tgggcacacc agacaatcgt aatcacaaaa cagacactga
6601 gccaggggcc caaagggtgt gatcatgaga gttaccggga cagcagtagg catgacagtc
6661 accaggaagg acaagggtgc tctgttgtta gtggccacac accaatttga caaggagtgt
6721 tgcgaaattt ttatttattt atttatttat tttgagatgg agtttcactc ttgttgccca
6781 ggctggagtg cggtggtaca atctcggctc actgcaacct ccacctccca ggttcaagcg
6841 attctcctgc ctcagcctcc caagtacctg ggactacagg tgcgtgccac cacacccagc
6901 taaattttgt gtttttagta gagatggggt ttcaccatgt tggccaggat ggtcttgaac
6961 ccctgacctc atgatctgcc tgcctcggcc tcccaaagtg ctgggattac aggcatgagc
7021 caccacgccc agccaaaata tttttttaaa gtcattttcc ttaagctgct tgggctacat
7081 gtgaaataca ctggacggtc aacattcctg tctcctccca tttgggctga tgcagcagat
7141 ccagggaatg ttacctgttt ctgctgctag aagatccagg aaattgggaa ggttacctga
7201 cgcacacatg gatgaaggcc atcatctaga aatggggtca accacaattg tgttaattcc
7261 gtagtgtcag ggattcttcg ggaaggtcaa cagtatgaag gattctgacc cctgtgcctc
7321 ccatttatgt gatcaggtga cagttaataa ccgtggaggt cacactcagc catccaacag
7381 ccttacagtg accctacaca aaagccccca aattccaaag acttttctt aacctaaagg
7441 aagaaattat tgttaattc cagtagagca actgaatata ctgggctatt tgtactttt
7501 tatagagaac tttaataata attctttaaa aatgagtttt tagaacaaag caactgacga
7561 tttcctaaga ttccaatgcc ctgagcttg taggaggact tagcctgggt cagctggagc
7621 accccgacc tgatctccca ctgccagatt ttcccatgct cctagggtat ggagtccacg
7681 tgggaatgac tgcaagttca ggtggaactt ggccgactga tgctctgcga gtttttaata
7741 gacactgggg acaactgctt aaggtttaga aacttccaaa ccacaggaaa gacattttta
7801 gtgtccccca tccagaggca gccctggaat aggattccca ggggtttctg ggaccccttt
7861 ccttgctccg tgaggctctg tggccatctt ttggcaggag gaggatgctt ccttggctct
7921 gtgcccagac ccgcctggtc cccaggtctc tcaccttggg tgaagattca gagatgccct
7981 gtaaggattt tgcccactgg gcaactcaga aatacttcga tctcccaaga tataagaggc
8041 agcagcaaac gtgcctattg acgtctgttt catagttacc acttacgcga gtagacagaa
8101 ctcggctttt cagaaaatag gtgtcaagtc cactttataa gaacctttt ttctaaaata
8161 agataaaagg tggctttgca ttttctgatt aaacgactgt gtctttgtca cctctgctta
8221 actttaggag tatccattcc tgtgattgta acttttgtt gatattcttc ctggaagaat
8281 atcattcttt tcttgaaggg ttggtttact agaatattca aaatcaatca tgaaggcagt
8341 tactattttg agtctaaagg ttttctaaaa attaacctca catcccttct gttagggtct
8401 ttcagaatat cttttataaa cagaagcatt tgaagtcatt gcttttgcta catgatttgt
8461 gtgtgtgaag acataccac gtttaaatca ttaattgaaa aacatcatat aagccccaac
8521 tttgtttgga ggaagagacg gaggttgagg tttttccttc tgtataagca cctactgaca
```

```
8581 aaatgtagag gccattcaac cgtcaaacac catttggtta tatcgcagag gagacggatg 8641 tgtaaattac tgcattgctt tttttttcag tttgtataac ctctaatctc cgtttgcatg 8701 atacgctttg ttagaaacat taattgtagt ttggaagcaa gtgtgtatga ataaagataa 8761 tgatcattcc aaaaaaaaaa aaaaaa
```

Agents that decrease the expression or activity of phospholipase C (PLC) or Inositol Triphosphate (IP3)

In some examples, certain agents that act as vasodilators are used that block the activity or expression of PLC or IP3. In embodiments, the PLC inhibitors comprise U-73122, U73343, and ET-18-OCH$_3$. In embodiments, IP3 inhibitors comprise 2-APB and Xestospongin C. In embodiments, the agent comprises hydralazine. It is contemplated that the inhibitors can be used alone or in any combination. In embodiments, the PLC or IP3 inhibitors, or pharmaceutically acceptable salts thereof are also contemplated herewith.

In certain embodiments, the agent that decreases the activity or expression of PLC or IP3 can be administered in a concentration from about 0.001 mg/kg to about 250 mg/kg body weight, e.g., 0.001 mg/kg, 0.05 mg/kg 0.01 mg/kg, 0.05 mg/kg, 1 mg/kg, 5 mg/kg, 10 mg/kg, 25 mg/kg, 50 mg/kg, 75 mg/kg, 100 mg/kg, 125 mg/kg, 150 mg/kg, 175 mg/kg, 200 mg/kg, 225 mg/kg, or 250 mg/kg body weight. In other embodiments, it is contemplated that the agent can be administered in a concentration higher, e.g., up to 1000 mg/kg body weight.

In some embodiments, combination therapy with an androgen antagonist is contemplated (e.g., antiandrogen). Antiandrogens are a class of drugs that prevent androgens like testosterone and dihydrotestosterone (DHT) from mediating their biological effects in the body. They act by blocking the androgen receptor (AR) and/or inhibiting or suppressing androgen production. Exemplary antiandrogens include:

Androgen receptor antagonists: Drugs that bind directly to and block the AR. These drugs include the steroidal antiandrogens cyproterone acetate, megestrol acetate, chlormadinone acetate, spironolactone, oxendolone, and osaterone acetate (veterinary) and the nonsteroidal antiandrogens flutamide, bicalutamide, nilutamide, topilutamide, enzalutamide, and apalutamide. Aside from cyproterone acetate and chlormadinone acetate, a few other progestins used in oral contraceptives and/or in menopausal HRT including dienogest, drospirenone, medrogestone, nomegestrol acetate, promegestone, and trimegestone also have varying degrees of AR antagonistic activity;

Androgen synthesis inhibitors: drugs that directly inhibit the enzymatic biosynthesis of androgens like testosterone and/or DHT. Examples include the CYP17A1 inhibitors ketoconazole, abiraterone acetate, and seviteronel, the CYP11A1 (P450scc) inhibitor aminoglutethimide, and the 5α-reductase inhibitors finasteride, dutasteride, epristeride, alfatradiol, and saw palmetto extract (Serenoa repens). A number of other antiandrogens, including cyproterone acetate, spironolactone, medrogestone, flutamide, nilutamide, and bifluranol, are also known to weakly inhibit androgen synthesis.

Antigonadotropins: Drugs that suppress the gonadotropin-releasing hormone (GnRH)-induced release of gonadotropins and consequent activation of gonadal androgen production. Examples include GnRH modulators like leuprorelin (a GnRH agonist) and cetrorelix (a GnRH antagonist), progestogens like allylestrenol, chlormadinone acetate, cyproterone acetate, gestonorone caproate, hydroxyprogesterone caproate, medroxyprogesterone acetate, megestrol acetate, osaterone acetate (veterinary), and oxendolone, and estrogens like estradiol, estradiol esters, ethinylestradiol, conjugated estrogens, and diethylstilbestrol.

Additional Examples: Drugs that oppose the effects of androgens by means other than the above. Examples include estrogens, especially oral and synthetic (e.g., ethinylestradiol, diethylstilbestrol), which stimulate sex hormone-binding globulin (SHBG) production in the liver and thereby decrease free and hence bioactive levels of testosterone and DHT; anticorticotropins such as glucocorticoids, which suppress the adrenocorticotropic hormone (ACTH)-induced production of adrenal androgens; and immunogens and vaccines against androstenedione like ovandrotone albumin and androstenedione albumin, which decrease levels of androgens via the generation of antibodies against the androgen and androgen precursor androstenedione (used only in veterinary medicine).

Connective Tissue Disorders

Connective tissue disease refers to a group of disorders involving the protein-rich tissue that supports organs and other parts of the body. Examples of connective tissue are fat, bone, and cartilage. These disorders often involve the joints, muscles, and skin, but they can also involve other organs and organ systems, including the eyes, heart, lungs, kidneys, gastrointestinal tract, and blood vessels. There are more than 200 disorders that affect the connective tissue. Causes and specific symptoms vary by the different types.

Examples of tissue diseases (e.g. epithelial, connective, muscle and nervous tissue) potentially treatable with the compositions and methods include, but are not limited to the following: autoimmune, degenerative, inflammatory, infectious, cancerous, viral, fungal, injured or trauma derived. These tissue and/or organ diseases may be the primary disease or may be caused by an existing disease and/or illness. Examples include amyloidosis, atiral fibrillation, convulsion, cramp, dermatomyositis, enchondroma, fibroma, lumbao, heritable connective tissue disorder (e.g., Marfan syndrome, Peyronie's disease, Ehlers-Danlos syndrome, Osteogenesis imperfecta, Stickler syndrome, Alport syndrome, Congenital contractural arachnodactyly), autoimmune connective tissue disorder (e.g., systemic lupus erythematosus (SLE), rheumatoid arthritis, Scleroderma, Sjogren's syndrome, mixed connective tissue disease, psoriatic arthritis), scurvy, muscle disease (e.g., muscle tumour, muscular dystrophy, disuse atrophy, denervation atrophy, Duchenne muscular dystrophy, facioscapulohumoral muscular dystrophy), hepatic diseasemyasthenia gravis, myopathy, myositis, myositis ossificans, cancer, fibromyalgia, muscle fatigue, spasm, spasticity, sprain, strain, brain injury, spinal cord injury, gliomas, neuroepitheliomatous, hypertension, cardiovascular disease, diabetes, Alzheimer's disease, cystitis, AIDS, rickets, and nerve sheath tumors. Examples of tissues, organs and/or body systems affected by disease and may be treated with the compositions, and methods described therein, but are not limited to the following: Immune system, sensory organs (e.g., organs of tase, smell, sight, hearing), digestive system (e.g., mouth, fauces, pharynx, esophagus, abdomen, stomach, small intestine, large intestine, liver, pancreas), urogenital apparatus, endocrinological systemt, metabolism, cardiovascular system (e.g., heart, blood pressure, arteries), hematology (e.g., blood chemistry), urinary organs (e.g., kidneys, ureters, urinary bladder, male urethra, female urethra, male gential organs (e.g., testes and their covering, ductus deferens, vesiculae seminales, ejaculatory ducts, penis, prostate, bulbourethral glands), female genital organs (e.g., ovaries, uterine tube, uterus, vagina, clitoris, Bartholin's glands, external organs, mammae)), ductless glands (e.g., thyroid, parathyroid, thymus, hypophysis cerebri, pineal body, chromaphil and corticol systems, spleen), reproduction, respiratory (e.g., larynx, trachea, bonchi, pleurae, mediastinum, lungs), central nervous system (e.g., nerves, nerve fibers), skin, epithelial (e.g., simple, stratified, pseudostratified columnar, glandular), connective (e.g., loose connective (e.g., areolar, adipose, reticular), and dense connective (e.g., dense regular, dense irregular)), cartilage (e.g., Hyaline, elastic, fibrous), muscle (e.g., skeletal muscle (e.g., type I, II, IIa, IIx, IIb), cardiac muscle, smooth muscle), nervous (e.g., neuron (e.g., motor neurons, interneuron, sensory neuron), neuroglia, spinal cord, nerves, brain).

In embodiments, the connective tissue disorder comprises a vasculopathy (e.g., vascular Ehlers-Danlos Syndrome), Marfan Syndrome, Loeys-Dietz Syndrome, or Familal thoracic aortic aneurysm.

Ehlers-Danlos Syndromes (EDSs)

Ehlers-Danlos syndromes (EDSs) are a group of genetic connective tissue disorders. Symptoms may include loose joints, stretchy skin, and abnormal scar formation. These can be noticed at birth or in early childhood. Complications may include aortic dissection, joint dislocations, scoliosis, chronic pain, or early osteoarthritis.

EDSs are due to a mutation in one of more than a dozen different genes. The specific gene affected determines the specific EDS. Some cases result from a new mutation occurring during early development, while others are inherited in an autosomal dominant or recessive manner. This results in defects in the structure or processing of collagen. The diagnosis may be confirmed with genetic testing or a skin biopsy. People may be misdiagnosed with hypochondriasis, depression, or chronic fatigue syndrome.

To date, no cure is known, however, physical therapy and bracing may help strengthen muscles and support joints. While some disorders result in a normal life expectancy, those that affect blood vessels generally result in a shorter life expectancy. EDSs affect about one in 5,000 people globally, and the prognosis depends on the specific disorder.

EDS Classification

Hypermobile EDS (type 3 hEDS) is characterized primarily by joint hypermobility affecting both large and small joints, which may lead to recurrent joint dislocations and subluxations (partial dislocation). In general, people with this type have soft, smooth, and velvety skin with easy bruising and chronic pain of the muscles and/or bones. The mutation that causes this type of EDS is unknown. Less skin involvement is seen than other types. No genetic test for this type is available.

Classical EDS (type 1 cEDS) is associated with extremely elastic (stretchy), smooth skin that is fragile and bruises easily; wide, atrophic scars (flat or depressed scars); and joint hypermobility. Molluscoid pseudotumors (calcified hematomas over pressure points such as the elbow) and spheroids (fat-containing cysts on forearms and shins) are also frequently seen. Hypotonia and delayed motor development may occur. The mutation that causes this type of EDS is in the genes COL5A1, COL5A2, and COL1A1. It involves the skin more than hEDS.

Vascular EDS (type 4 vEDS) is characterized by thin, translucent skin that is extremely fragile and bruises easily. Arteries and certain organs such as the intestines and uterus are also fragile and prone to rupture. People with this type typically have short stature, and thin scalp hair. It also has characteristic facial features including large eyes, an undersized chin, sunken cheeks, a thin nose and lips, and ears without lobes. Joint hypermobility is present, but generally confined to the small joints (fingers, toes). Other common features include club foot, tendon and/or muscle rupture, acrogeria (premature aging of the skin of the hands and feet), early onset varicose veins, pneumothorax (collapse of a lung), recession of the gums, and a decreased amount of fat under the skin. Is can be caused by the mutations in the COL3A1 gene.

Kyphoscoliosis EDS (type 6 kEDS) is associated with severe hypotonia at birth, delayed motor development, progressive scoliosis (present from birth), and scleral fragility. Affected people may also have easy bruising, fragile arteries that are prone to rupture, unusually small corneas, and osteopenia (low bone density). Other common features include a "marfanoid habitus" which is characterized by long, slender fingers (arachnodactyly), unusually long limbs, and a sunken chest (pectus excavatum) or protruding chest (pectus carinatum). It can be caused by mutations in the gene PLOD1.

Arthrochalasia EDS (types 7A & B aEDS) is characterized by severe joint hypermobility and congenital hip dislocation. Other common features include fragile, elastic skin with easy bruising, hypotonia, kyphoscoliosis (kyphosis and scoliosis), and mild osteopenia. Type-I collagen is usually affected. It is very rare, with about 30 cases reported. It is more severe than the hypermobility type. Mutations in the genes COL1A1 and COL1A2 cause it.

Dermatosparaxis EDS (type 7C dEDS) is associated with extremely fragile skin leading to severe bruising and scarring; saggy, redundant skin, especially on the face; and hernias. It is extremely rare, with around 10 cases reported.

Brittle cornea syndrome is characterized by thin corneaa, early-onset progressive keratoglobus or keratoconus, and blue sclerae. Classic symptoms, such as hypermobile joints and hyperelastic skin, are also seen often.

Classical-like EDS (type 1 cEDS) is characterized by skin hyperextensibility with velvety skin texture and absence of atrophic scarring, generalized joint hypermobility with or without recurrent dislocations (most often shoulder and ankle), and easily bruised skin or spontaneous ecchymoses (discolorations of the skin resulting from bleeding underneath).

Spondylodysplastic EDS (spEDS) is characterized by short stature (progressive in childhood), muscle hypotonia (ranging from severe congenital, to mild later-onset), and bowing of limbs.

Musculocontractural EDS (mcEDS) is characterized by congenital multiple contractures, characteristically adduction-flexion contractures and/or talipes equinovarus (clubfoot), characteristic craniofacial features, which are evident at birth or in early infancy, and skin features such as skin hyperextensibility, bruising, skin fragility with atrophic scars, and increased palmar wrinkling.

Myopathic EDS (mEDS) is characterized by congenital muscle hypotonia and/or muscle atrophy that improves with age, proximal joint contractures (joints of the knee, hip and elbow), and hypermobility of distal joints (joints of the ankles, wrists, feet and hands).

Periodontal EDS (pEDS) is characterized by severe and intractable periodontitis of early onset (childhood or adolescence), lack of attached gingiva, pretibial plaques, and family history of a first-degree relative who meets clinical criteria.

Cardiac-valvular EDS (cvEDS) is characterized by severe progressive cardiac-valvular problems (aortic valve, mitral valve), skin problems (hyperextensibility, atrophic scars, thin skin, easy bruising), and joint hypermobility (generalized or restricted to small joints).

Methods of Treatment

The present disclosure provides methods for the treatment of vasopathy (e.g., vEDS) or connective tissue disorders in a subject in need thereof by administering to the subject a therapeutically effective amount of an agent, wherein the agent decreases the activity or expression of extracellular signal-regulated kinase (ERK) or protein kinase C (PKC). The method further comprises administering an agent that decreases the activity or expression of phospholipase C (PLC) or inositol triphosphate (IP3). In embodiments, the agent comprises an antibody or fragment thereof, a polypeptide, a small molecule, a nucleic acid molecule, or any combination, for the preparation of a medicament useful for the treatment of vasopathy (e.g., vEDS) or connective tissue disorders.

The present disclosure also provides methods comprising combination therapy. As used herein, "combination therapy" or "co-therapy" includes the administration of a therapeutically effective amount of an agent (e.g., an agent that decreases the activity or expression of ERK, PKC and/or PLC or IP3), or a pharmaceutically acceptable salt thereof, with at least one additional active agent, also referred to herein as an "active pharmaceutical ingredient" ("API"), as part of a treatment regimen intended to provide a beneficial effect from the co-action of the agent (e.g., an agonist, antagonist or inhibitor) and the additional active agent.

In accordance with the embodiments described below, "the additional API" is understood to refer to the at least one additional API administered in a combination therapy regimen with agent (e.g., an agent that decreases the activity or expression of ERK, PKC and/or PLC or IP3). In addition, it is understood that more than one of the additional APIs described below may be utilized in the regimen. The terms "combination therapy" or "combination therapy regimen" are not intended to encompass the administration of two or more therapeutic compounds as part of separate monotherapy regimens that incidentally and arbitrarily result in a beneficial effect that was not intended or predicted.

Preferably, the administration of a composition comprising agent (e.g., e.g., an agent that decreases the activity or expression of ERK, PKC and/or PLC or IP3) in combination with one or more additional APIs as discussed herein provides a synergistic response in the subject being treated. In this context, the term "synergistic" refers to the efficacy of the combination being more effective than the additive effects of either single therapy alone.

The present disclosure also provides methods comprising combination therapy for the treatment of vasopathy (e.g., vEDS) or connective tissue disorders. As used herein, "combination therapy" or "co-therapy" includes the administration of a compound described herein, with at least one additional agent, as disclosed herein, as part of a specific treatment regimen intended to provide the beneficial effect from the co-action of these therapeutic compounds. The at least one additional agent may be a therapeutic agent or a non-therapeutic agent. The beneficial effect of the combination includes, but is not limited to, pharmacokinetic or pharmacodynamic co-action resulting from the combination of therapeutic compounds. The beneficial effect of the combination may also relate to the mitigation of a toxicity, side effect, or adverse event associated with another agent in the combination. "Combination therapy" may be, but generally is not, intended to encompass the administration of two or more of these therapeutic compounds as part of separate monotherapy regimens that incidentally and arbitrarily result in the combinations of the present disclosure.

Accordingly, in certain embodiments, a subject in need thereof is administered one or more agents that inhibit the expression or activity of mitogen activated protein kinase/extracellular signal regulated kinase (MEK), extracellular signal regulated kinase (ERK), phospholipase C (PLC), inositol triphosphate (IP3) or protein kinase C (pKC), and thereby inhibiting the activity of ERK, PLC, IP3, or PKC.

In certain embodiments, a subject in need thereof is administered one or more agents that inhibit the activity or expression of one or more molecules associated with the mitogen-activated protein kinase (MAPK) pathway, e.g. RAS-RAF/MEK/Extracellular signal-regulated kinase (ERK) protein kinases.

In the context of combination therapy, administration of antagonist may be simultaneous with or sequential to the administration of the one or more additional agents. In another aspect, administration of the different components of a combination therapy may be at different frequencies. The one or more additional agents may be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a compound of the present disclosure.

The one or more additional agents can be formulated for co-administration with an agent of the present disclosure in a single dosage form, as described in greater detail herein. The one or more additional agents can be administered separately from the dosage form that comprises the compound of the present disclosure. When the additional agent is administered separately from a compound of the present disclosure, it can be by the same or a different route of administration as the compound of the instant disclosure.

Preferably, the administration of a composition comprising an agent of the present disclosure in combination with one or more additional agents provides a synergistic response in the subject having a disorder, disease or condition of the present disclosure. In this context, the term "synergistic" refers to the efficacy of the combination being more effective than the additive effects of either single therapy alone. The synergistic effect of combination therapy according to the disclosure can permit the use of lower dosages and/or less frequent administration of at least one agent in the combination compared to its dose and/or frequency outside of the combination. The synergistic effect can be manifested in the avoidance or reduction of adverse or unwanted side effects associated with the use of either therapy in the combination alone.

"Combination therapy" also embraces the administration of the compounds of the present disclosure in further combination with non-drug therapies (e.g., surgery or radiation treatment). Where the combination therapy further comprises a non-drug treatment, the non-drug treatment may be conducted at any suitable time so long as a beneficial effect from the co-action of the combination of the therapeutic compounds and non-drug treatment is achieved. For example, in appropriate cases, the beneficial effect is still achieved when the non-drug treatment is temporally removed from the administration of the therapeutic compounds, perhaps by days or even weeks.

In embodiments of the methods described herein, agents (e.g., an agent that decreases the activity or expression of ERK, PKC and/or PLC or IP3), may be administered alone or in combination with at least one additional agent in a method for treating vasopathy (e.g., vEDS) or connective tissue disorders. In embodiments, the agent, and the at least one additional agent are administered in a single dosage form. In another aspect, the agent and the at least one additional agent are administered in separate dosage forms. In embodiments, the at least one additional agent is a therapeutic agent. In embodiments, the therapeutic agent is indicated for the treatment of vasopathy (e.g., vEDS) or connective tissue disorders. In another aspect, the agent is administered in combination with at least one additional agent that is not for the treatment of vasopathy (e.g., vEDS) or connective tissue disorders, e.g., a second agent that serves to mitigate a toxicity or adverse event associated with another active agent being administered in the combination therapy.

In embodiments, the at least one additional agent is directed towards targeted therapy, wherein the treatment targets vasopathy (e.g., vEDS) or connective tissue disorders, proteins, or the tissue environment that contributes to vasopathy (e.g., vEDS) or connective tissue disorder progression.

In some embodiments, combination therapy with an androgen antagonist is contemplated (e.g., antiandrogen). Antiandrogens are a class of drugs that prevent androgens like testosterone and dihydrotestosterone (DHT) from mediating their biological effects in the body. They act by blocking the androgen receptor (AR) and/or inhibiting or suppressing androgen production.

In embodiments, exemplary combinations comprise androgen antagonists plus PLC, IP3, PKC, or ERK inhibitors.

The term "therapeutically effective amount" refers to an amount sufficient to treat, ameliorate a symptom of, reduce the severity of, or reduce the duration of the disease, disorder or condition, or enhance or improve the therapeutic effect of another therapy, or to prevent an identified disease, disorder or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic or combination of therapeutics selected for administration.

An effective amount of the agent can be administered once daily, from two to five times daily, up to two times or up to three times daily, or up to eight times daily. In embodiments, the agent is administered thrice daily, twice daily, once daily, fourteen days on (four times daily, thrice daily or twice daily, or once daily) and 7 days off in a 3-week cycle, up to five or seven days on (four times daily, thrice daily or twice daily, or once daily) and 14-16 days off in 3 week cycle, or once every two days, or once a week, or once every 2 weeks, or once every 3 weeks.

An effective amount of an agent (e.g., an agent that decreases the activity or expression of ERK, PKC and/or PLC or IP3) can range from about 0.001 mg/kg to about 1000 mg/kg, from about 0.01 mg/kg to about 100 mg/kg, from about 0.1 mg/kg to about 10 mg/kg; or any range in which the low end of the range is any amount from 0.001 mg/kg and 900 mg/kg and the upper end of the range is any amount from 0.1 mg/kg and 1000 mg/kg (e.g., 0.005 mg/kg and 200 mg/kg, 0.5 mg/kg and 20 mg/kg). Effective doses will also vary, as recognized by those skilled in the art, depending on the diseases treated, route of administration, excipient usage, and the possibility of co-usage with other therapeutic treatments such as use of other agents.

In more specific aspects, an agent of the disclosure (e.g., an agent that decreases the activity or expression of ERK, PKC and/or PLC or IP3) is administered at a dosage regimen of 30-300 mg/day (e.g., 30, 35, 40, 45, 50, 55, 60, 65, 70, 75, 80, 85, 90, 95, 100, 125, 150, 175, 200, 225, 250, 275, or 300 mg/day) for at least 1 week (e.g., 1, 2, 3, 4, 5, 6, 7, 8, 9, 10, 11, 12, 36, 48, or more weeks). In certain embodiments, a compound(s) embodied herein is administered at a dosage regimen of 100-300 mg/day for 4 or 16 weeks. Alternatively or subsequently, an agent embodied herein is administered at a dosage regimen of 100 mg twice a day for 8 weeks, or optionally, for 52 weeks.

As used herein, a "subject in need thereof" is a subject having a disease, disorder or condition, or a subject having an increased risk of developing a disease, disorder or condition relative to the population at large. In a preferred aspect, the subject in need thereof is a subject having vasopathy (e.g., vEDS) or connective tissue disorders or having an increased risk of developing vasopathy (e.g., vEDS) or connective tissue disorders relative to the population at large. The subject in need thereof can be one that is "non-responsive" or "refractory" to a currently available therapy for the disease or disorder. In this context, the terms "non-responsive" and "refractory" refer to the subject's response to therapy as not clinically adequate to relieve one or more symptoms associated with the disease or disorder.

A "subject" includes a mammal. The mammal can be e.g., any mammal, e.g., a human, primate, vertebrate, bird, mouse, rat, fowl, dog, cat, cow, horse, goat, camel, sheep or a pig. Preferably, the mammal is a human. The terms "subject" and "patient" are used interchangeably herein.

The present disclosure provides a monotherapy for the treatment of a disease, disorder or condition as described herein. As used herein, "monotherapy" refers to the administration of a single active or therapeutic compound to a subject in need thereof. Preferably, monotherapy will involve administration of a therapeutically effective amount of an active compound. For example, monotherapy with an agent of the disclosure, can be administered in a therapeutically effective amount to a subject in need of treatment. Monotherapy may be contrasted with combination therapy, in which a combination of multiple active compounds is administered, preferably with each component of the combination present in a therapeutically effective amount. In one aspect, monotherapy with an agent of the disclosure is more effective than combination therapy in inducing a desired biological effect.

As used herein, "treatment", "treating" or "treat" describes the management and care of a patient for the purpose of combating a disease, condition, or disorder and includes the administration of an agent of the disclosure to alleviate the symptoms or complications of a disease, condition or disorder, or to eliminate the disease, condition or disorder.

As used herein, "prevention", "preventing" or "prevent" describes reducing or eliminating the onset of the symptoms or complications of the disease, condition or disorder and includes the administration of an agent of the disclosure to reduce the onset, development or recurrence of symptoms of the disease, condition or disorder.

As used herein, the term "alleviate" is meant to describe a process by which the severity of a sign or symptom of a disorder is decreased. Importantly, a sign or symptom can be alleviated without being eliminated. In a preferred embodiment, the administration of an agent of the disclosure leads to the elimination of a sign or symptom, however, elimination is not required. Effective dosages are expected to decrease the severity of a sign or symptom.

As used herein the term "symptom" is defined as an indication of disease, illness, injury, or that something is not right in the body. Symptoms are felt or noticed by the individual experiencing the symptom, but may not easily be noticed by others. Others are defined as non-health-care professionals.

Treating a disorder, disease or condition according to the methods described herein can result in a decrease in vasopathy (e.g., vEDS) or connective tissue disorder progression rate. Preferably, after treatment, vasopathy (e.g., vEDS) or connective tissue disorder progression rate is reduced by at least 5% relative to number prior to treatment; more preferably, vasopathy (e.g., vEDS) or connective tissue disorder progression rate is reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Vasopathy (e.g., vEDS) or connective tissue disorders progression rate may be measured by any reproducible means of measurement.

As used herein, the term "selectively" means tending to occur at a higher frequency in one population than in another population. The compared populations can be cell populations. Preferably, an agent of the present disclosure acts selectively on a hyper-proliferating cells but not on a normal cell. An agent of the present disclosure acts selectively to modulate one molecular target but does not significantly modulate another molecular target.

Combination Therapy

In embodiments, the disclosure also provides methods comprising combination therapy of hydralazine and at least one additional active agent. In embodiments, the at least one additional active agent is a therapeutic agent, e.g., an antiandrogen compound such as bicalutamide or spironolactone.

As used herein, "combination therapy" or "co-therapy" includes the administration of a therapeutically effective amount of an agent described herein with at least one additional active agent, as part of a specific treatment regimen intended to provide a beneficial effect from the co-action of the agent and the additional active agent. The beneficial effect of the combination includes, but is not limited to, pharmacokinetic or pharmacodynamic co-action resulting from the combination of therapeutically active compounds. "Combination therapy" is not intended to encompass the administration of two or more therapeutic compounds as part of separate monotherapy regimens that incidentally and arbitrarily result in a beneficial effect that was not intended or predicted.

Preferably, the combination therapy provides a synergistic response in the subject being treated. In this context, the term "synergistic" refers to the efficacy of the combination being more effective than the additive effects of either single therapy alone. The synergistic effect of a combination therapy according to the invention can permit the use of lower dosages and/or less frequent administration of at least one agent in the combination compared to its dose and/or frequency outside of the combination. Additional beneficial effects of the combination can be manifested in the avoidance or reduction of adverse or unwanted side effects associated with the use of either therapy in the combination alone (also referred to as monotherapy).

"Combination therapy" also embraces the administration of the agent that inhibits or reduces the biological activity and/or expression of a signaling pathway (e.g., PLC/IP3/PKC/ERK) of the present invention in further combination with non-drug therapies (e.g., surgery or radiation treatment). Where the combination therapy further comprises a non-drug treatment, the non-drug treatment may be conducted at any suitable time so long as a beneficial effect from the co-action of the combination of the therapeutic compounds and non-drug treatment is achieved. For example, in appropriate cases, the beneficial effect is still achieved when the non-drug treatment is temporally removed from the administration of the therapeutic compounds, perhaps by days or even weeks. The non-drug treatment can be selected from chemotherapy, radiation therapy, hormonal therapy, anti-estrogen therapy, gene therapy, and surgery.

In the context of the methods described herein, the amount of an agent administered to the subject is a therapeutically effective amount. The term "therapeutically effective amount" refers to an amount sufficient to treat, ameliorate a symptom of, reduce the severity of, or reduce the duration of the disease being treated (e.g., vEDS), or enhance or improve the therapeutic effect of another therapy, or sufficient to exhibit a detectable therapeutic effect in the subject. In one embodiment, the therapeutically effective amount of agent is the amount effective in reducing a signaling pathway (e.g., PLC/IP3/PKC/ERK).

In embodiments, the administration of hydralazine and an antiandrogen agent according to the methods described here leads to the elimination of a symptom or complication of the disease (e.g., vEDS) being treated; however, elimination is not required. In one embodiment, the severity of the symptom or complication is decreased.

Pharmaceutical Compositions

In certain embodiments, the present invention provides for a pharmaceutical composition comprising an agent (e.g., an agent that decreases the activity or expression of ERK, PKC and/or PLC or IP3) are employed in the present invention. The agent can be suitably formulated and introduced into a subject or the environment of a cell by any means recognized for such delivery.

A "pharmaceutical composition" is a formulation containing the agents described herein in a pharmaceutically acceptable form suitable for administration to a subject. As used herein, the phrase "pharmaceutically acceptable" refers to those compounds, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Such compositions typically include the agent and a pharmaceutically acceptable carrier. As used herein the language "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions.

As used herein, the term "pharmaceutically acceptable salt," is a salt formed from, for example, an acid and a basic group of an agent described herein. Illustrative salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, besylate, gentisinate, fumarate, gluconate, glucaronate, saccharate, formate, benzoate, glutamate, methanesulfonate, ethanesulfonate, benzenesulfonate, p-toluenesulfonate, and pamoate (e.g., 1,1'-methylene-bis-(2-hydroxy-3-naphthoate)) salts.

A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in a selected solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

The compositions of the invention could also be formulated as nanoparticle formulations. The compounds of the invention can be administered for immediate-release, delayed-release, modified-release, sustained-release, pulsed-release and/or controlled-release applications. The pharmaceutical compositions of the invention may contain from 0.01 to 99% weight-per volume of the active material. For administration by inhalation, the compounds are delivered in the form of an aerosol spray from pressured container or dispenser which contains a suitable propellant, e.g., a gas such as carbon dioxide, or a nebulizer. Such methods include those described in U.S. Pat. No. 6,468,798.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art. The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers.

These can be prepared according to methods known to those skilled in the art, for example, as described in U.S. Pat. No. 4,522,811.

Toxicity and therapeutic efficacy of such compounds can be determined by standard pharmaceutical procedures in cell cultures or experimental animals, e.g., for determining the LD50 (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For a compound used in a method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of an agent (i.e., an effective dosage) depends on the agent selected. For instance, single dose amounts of an agent in the range of approximately 1 pg to 1000 mg may be administered; in some embodiments, 10, 30, 100, or 1000 pg, or 10, 30, 100, or 1000 ng, or 10, 30, 100, or 1000 µg, or 10, 30, 100, or 1000 mg may be administered. In some embodiments, 1-5 g of the compositions can be administered.

A therapeutically effective amount of the compound of the present invention can be determined by methods known in the art. In addition to depending on the agent and selected/pharmaceutical formulation used, the therapeutically effective quantities of a pharmaceutical composition of the invention will depend on the age and on the general physiological condition of the patient and the route of administration. In certain embodiments, the therapeutic doses will generally be from about 10 and 2000 mg/day and preferably from about 30 and 1500 mg/day. Other ranges may be used, including, for example, 50-500 mg/day, 50-300 mg/day, 100-200 mg/day.

Administration may be once a day, twice a day, or more often, and may be decreased during a maintenance phase of the disease or disorder, e.g. once every second or third day instead of every day or twice a day. The dose and the administration frequency will depend on the clinical signs, which confirm maintenance of the remission phase, with the reduction or absence of at least one or more preferably more than one clinical signs of the acute phase known to the person skilled in the art. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of an agent can include a single treatment or, optionally, can include a series of treatments.

It can be appreciated that the method of introducing an agent into the environment of a cell will depend on the type of cell and the makeup of its environment. Suitable amounts of an agent must be introduced and these amounts can be empirically determined using standard methods. Exemplary effective concentrations of an individual agent in the environment of a cell can be 500 millimolar or less, 50 millimolar or less, 10 millimolar or less, 1 millimolar or less, 500 nanomolar or less, 50 nanomolar or less, 10 nanomolar or less, or even compositions in which concentrations of 1 nanomolar or less can be used.

The pharmaceutical compositions can be included in a kit, container, pack, or dispenser together with instructions for administration.

EXAMPLES

The following examples are put forth so as to provide those of ordinary skill in the art with a complete disclosure and description of how to make and use the assay, screening, and therapeutic methods of the invention, and are not intended to limit the scope of what the inventors regard as their invention.

Example 1: Generation of Knock-in Glycine Substitution vEDS Mice

Novel knock-in glycine substitution (Col3a1 G209S/+ and Col3a1 G938D/+) vEDS mice were created using CRISPR/Cas9. The mouse model recapitulated human vascular phenotypes, and a molecular basis for ultimate failure of the vessel wall was uncovered, through exploitation of environmental effects on the disease phenotype.

To introduce each mutation, 3 guide RNAs (tracrRNA+crRNA) were designed to target the DNA regions flanking the intended mutation site. A DNA oligo repair template (ssDNA oligo) was also designed that included homologous sequences upstream and downstream of the target region, as well as the intended mutation. Pronuclear injection of one-cell $C_{57}BL/6J$ embryos was performed by the JHU Transgenic Core using standard microinjection techniques using a mix of Cas9 protein, tracrRNA, crRNA, and ssDNA oligo diluted in RNAse free injection buffer. Injected embryos were transferred into the oviducts of pseudopregnant ICR females using established techniques. Sanger sequencing of the site was utilized to confirm introduction of the mutation, and the mice were backcrossed for at least 4 generations to eliminate off-target effects. For the G209S mouse, the mutation introduced was c.625_626 GG>TC, corresponding to p.Gly210Ser in humans. For the G938D mouse, the mutation introduced was c.2813G>A, corresponding to p.Gly939Ser in humans. The Wild-type Human Col3a1 mRNA NCBI Accession No: NM_000090.3; the wild-type Mouse Col3a1 mRNA NCBI Accession No.: NM_009930.2.

Figure 1B:
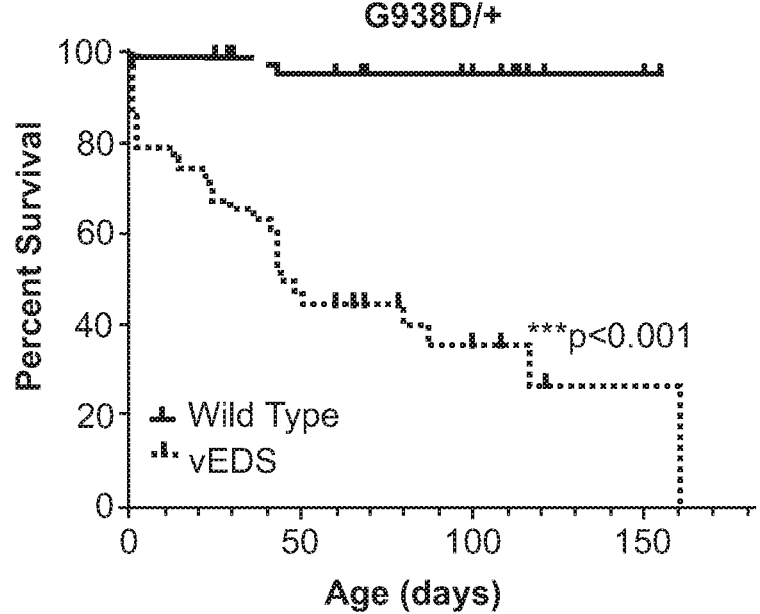
FIG. 1B is a graph demonstrating that the G938D/+ mouse model recapitulated vEDS phenotypes. The percent survival versus age is shown. The median survival was 45 days, p<0.0001.
Figure 1C:
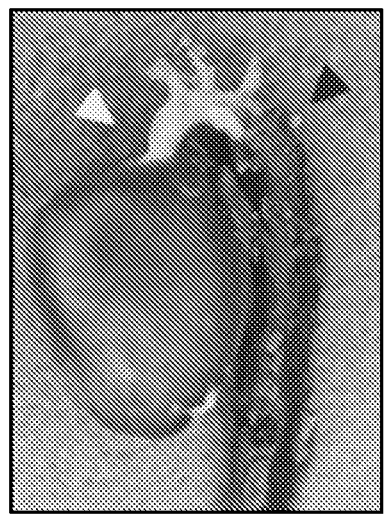
FIG. 1C is an image depicting the heart and aorta of a vEDS mouse. The arrowhead (left side) indicates the ascending aorta and the red arrowheard (right side) indicates the site of aortic dissection in the descending aorta.

Example 2: Col3a1 G209S/+ and Col3a1 G938D/+ Mouse Models Recapitulated vEDS Phenotypes Both the Col3a1 G209S/+ and Col3a1 G938D/+ mouse models recapitulated vEDS phenotypes. Mice with vEDS die suddenly due to aortic rupture, aortic dissection or organ rupture, most often presenting with hemothorax or hemoperitoneum at necropsy. The mice with the Col3a1 G938D/+ mutation present with a more severe phenotype (median survival=45 days versus 400 days for the Col3a1 G209S/+ model, p<0.0001, FIG. 1A-1C). FIG. 1A is a graph demonstrating that the G209S/+ mouse model recapitulated vEDS phenotypes, and the median survival was 400 days, p<0.0001. In FIG. 1B, survival of the G938D/+ mouse model is shown, and recapitulated vEDS, and the median survival was 45 days, p<0.0001.

In either mouse model, no evidence of aortic root aneurysm via echocardiography was observed.

Example 3: Signaling Abnormalities were Mediators of Disease Pathology in vEDS

Figure 1D:
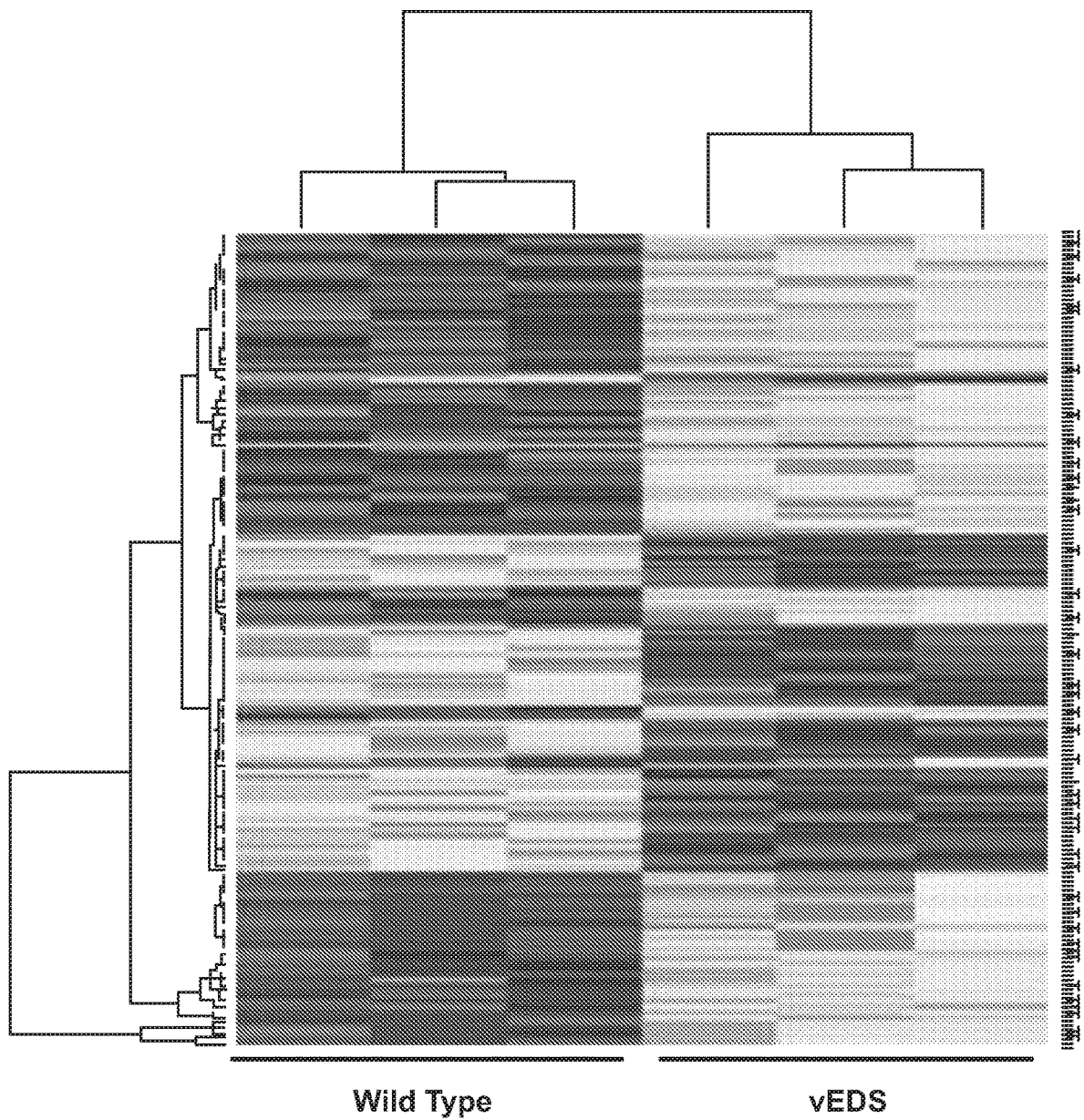
FIG. 1D is a graph demonstrating that the vEDS samples clustered separately from controls, indicating a significant difference in the transcriptome of vEDS aortas.

It was hypothesized that signaling abnormalities could be major mediators of disease pathology in vEDS. To test this hypothesis, RNA-seq was performed on the proximal descending thoracic aortas of three Col3a1 G209S/+ mice, three Col3a1 G938D/+ mice, and three Col3a1+/+ (wild type) mice, given that the proximal descending aorta is the most common location of aortic dissection in this model. Unsupervised hierarchical clustering using the most differentially expressed genes (FDR <0.10) was performed. vEDS samples clustered separately from controls (FIG. 1D), indicating significant differences in the transcriptome of vEDS aortas.

Figures 1E, 1F:
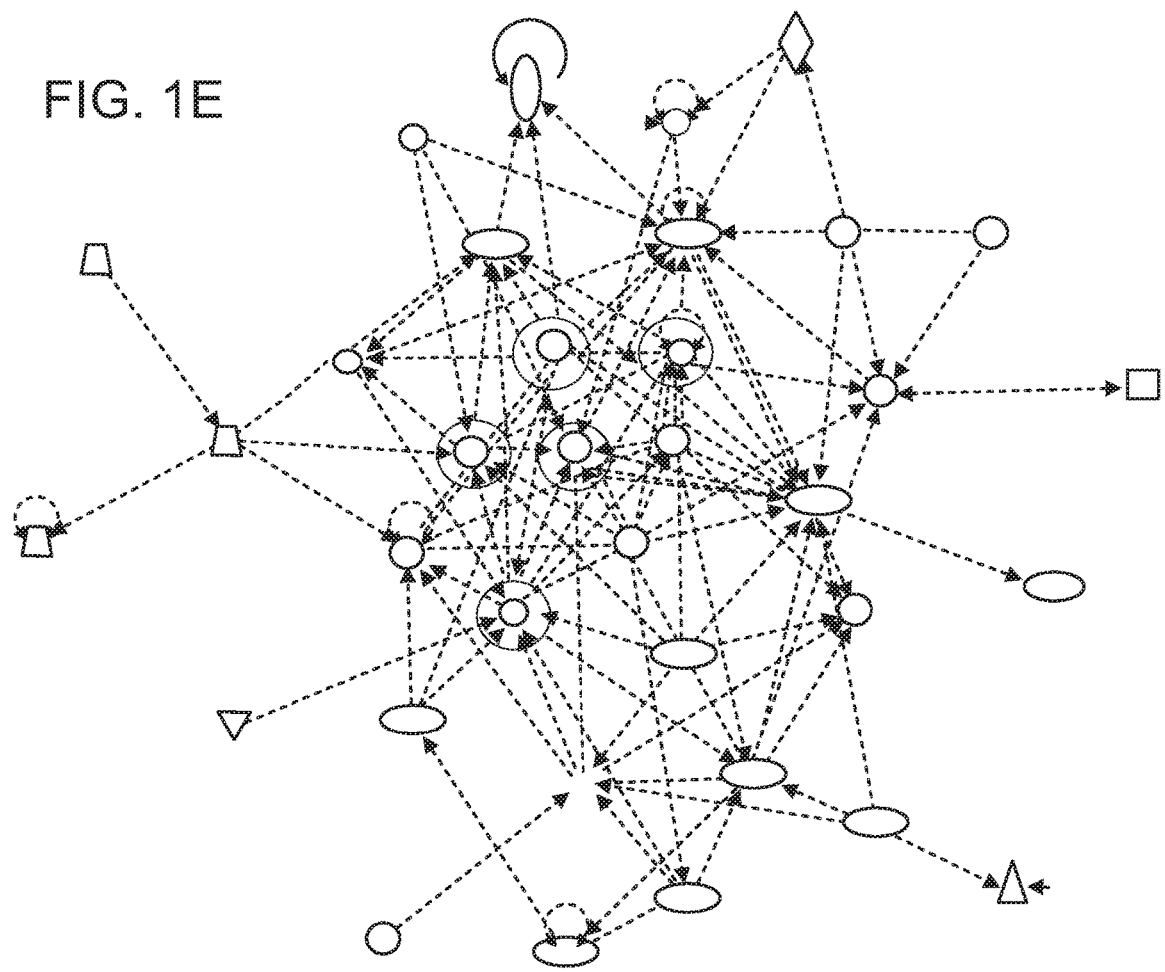
FIG. 1E is an illustration demonstrating a network analysis which indicated that vEDS aortas exhibited gene expression signatures for elevations in mitogen-activated protein kinase (MAPK) activity (P38, JNK, AKT, ERK, ERK1/2).
FIG. 1F is a table illustrating that upstream analysis predicted that the transcriptional differences in vEDS aortas were driven by G protein coupled receptor (GPCR) activation, which signaled through the related PLC/IP3/PKC/ERK axis.

Network analysis indicated that vEDS aortas exhibited gene expression signatures for elevations in mitogen-activated protein kinase (MAPK) activity [P38, JNK, AKT, ERK, ERK1/2] (FIG. 1E).

Furthermore, upstream analysis predicted that the transcriptional differences in vEDS aortas were driven by G protein coupled receptor (GPCR) activation, which signals through the related PLC/IP3/PKC/ERK axis (FIG. 1F).

The signature for elevations in GPCR and MAPK signaling were confirmed by immunoblotting for markers of active signaling through this pathway, and found ERK1/2 phosphorylation and PKC phosphorylation to be significantly higher in vEDS aortas (FIG. 1G).

In contrast to Marfan syndrome (MFS) or Loeys-Dietz syndrome (LDS), expression profiling of vEDS aorta does not show a synthetic repertoire typical for high TGFβ signaling, however evidence of increased ERK activation (similar to MFS and LDS) was observed. A small human study suggested that the beta-blocker celiprolol has the potential to delay adverse events in patients with vEDS, while angiotensin receptor blockers such as losartan afford dramatic protection in mouse models of MFS or LDS.

Furthermore, there is no evidence of protection from dissection or death in losartan-treated vEDS mice, while celiprolol associates with significant acceleration of dissection and death in both vEDS models; both drugs achieved the predicted lowering of hemodynamic stress. While early data show that hydralazine, which inhibits the PLC/IP3/PKC/ERK axis, affords some protection in vEDS mice, these data highlight the need for discovery-based methods to reveal unanticipated therapeutic strategies.

The vEDS mutations were introduced onto pure 129 and BL6 backgrounds to assess for modulation of phenotypic severity. Both mutations are associated with early death due to aortic dissection on the BL6 background. Quite remarkably, the 129-background lead to complete protection from dissection for both vEDS genotypes, with a fully normal lifespan. Rescue associates with normalization of gene expression profiles for the aortic wall. These data provide rationale and incentive to perform genetic studies to identify the source and mechanism of modification in vEDS mice, with the hope and intention to mimic nature's successful strategies using pharmacologic agents.

Example 4: Pharmacological Inhibition of the PLC/IP3/PKC/ERK Axis Decreased the Risk of Aortic Rupture in vEDS Mice Since activation of the PLC/IP3/PKC/ERK axis has been shown to be pathogenic in MFS[7], it was hypothesized that pharmacological inhibition of this axis would decrease the risk of aortic rupture in vEDS mice.

Pharmacological ERK Antagonist Increased Survival

Pharmacological ERK antagonists were tested to support the role of ERK activation in the pathogenesis of vEDS and as a method to identify therapeutic strategies for vEDS. Mice were treated with cobimetinib [GDC-0973, RO5514041] (2 mg/kg/day), an FDA-approved inhibitor of MEK, the kinase that activates ERK[8]. It was hypothesized that if ERK activation was truly driving disease risk, ERK inhibition would rescue the risk of death from aortic dissection.

In keeping with this hypothesis, a 94% survival was observed after 45 days of treatment, compared to only 55% survival with no treatment (FIG. 2A).

Pharmacological PKC Inhibition Increased Survival

Next, further studies were performed to test agents that inhibit PKC activation. Mice were treated with ruboxistaurin [LY 333531] (10 mg/kg/day), a well-tolerated orally administered pharmacologic agent that specifically inhibits PKC beta[9]. It was hypothesized that if ERK activation, and thereby disease risk, was driven by PLC/IP3/PKC activation, a pharmacologic PKC inhibitor would also rescue the risk of death from aortic dissection.

In keeping with this hypothesis, 100% survival was observed after 39 days of treatment, compared to only 55% survival with no treatment (FIG. 2B).

Agents that Inhibit the PLC/IP3/PKC/ERK Signaling Cascade Increased Survival

Further studies were performed to test other medications that inhibit this signaling cascade. The mice were treated by administration of hydralazine (32 mg/kg/d), which blocks the PLC/IP3/PKC/ERK axis, hypothesizing that this medication would target the same pathway and thereby afford similar protection[10]. A remarkable protection was observed, 98% survival at 45 days of age, the median survival for an untreated vEDS mouse (FIG. 2C).

While the survival was affected at puberty, this risk was seen almost exclusively in male mice and so, treatment with an androgen antagonist may be beneficial to these mice. Furthermore, the dose of hydralazine may be insufficient to completely inhibit this pathway in this mouse model, and a higher dose of hydralazine may prove beneficial.

The mice are treated with combination therapy of hydralazine and an androgen antagonist.

Furthermore, the mice are treated with higher doses of hydralazine.

These results suggest that inhibition of excessive PLC/IP3/PKC/ERK signaling in the aorta rescues risk of death due to aortic dissection in the mouse model of vEDS.

Example 5: Oxytocin-Induced ERK Signaling Activated the PLC/IP3/OKC/ERK Axis and Worsened the Risk of Aortic Dissection Patients with vascular Ehlers Danlos Syndrome (vEDS) experience dissection of medium-to-large arteries. Many features of vEDS are distinctly different from other heritable vasculopathies, such as Marfan Syndrome (MFS) and Loeys-Dietz Syndrome (LDS) which have been associated with excessive TGFβ activity. These include no particular predisposition for involvement of the aortic root and dissection without prior vessel dilation. Vascular rupture in patients with vEDS is difficult to anticipate or prevent. Pregnancy specifically increases the risk of dissection, with complications occurring in over 50% of pregnancies, and death in about 12-25% of pregnancies. The predominant postpartum occurrence of vascular dissection is not consistent with a mechanism that singularly invokes hemodynamic stress. Instead, it was hypothesized that oxytocin, a hormone which initiates uterine contraction and is sustained postpartum during lactation, may contribute to pregnancy-associated risk. Expression of the oxytocin receptor is induced in the aorta during pregnancy and the hormone stimulates peripheral tissues through the activation of ERK, a signaling cascade previously implicated in the pathogenesis of MFS and LDS.

Previously, it was shown that pregnancy-associated aortic dissection is largely driven by lactation-associated oxytocin release and oxytocin-induced ERK signaling in MFS mouse aortas[11]. Thus, oxytocin-induced ERK signaling was used as a method to test whether activation of the PLC/IP3/PKC/ERK axis would worsen the risk of aortic dissection.

Figure 3A:
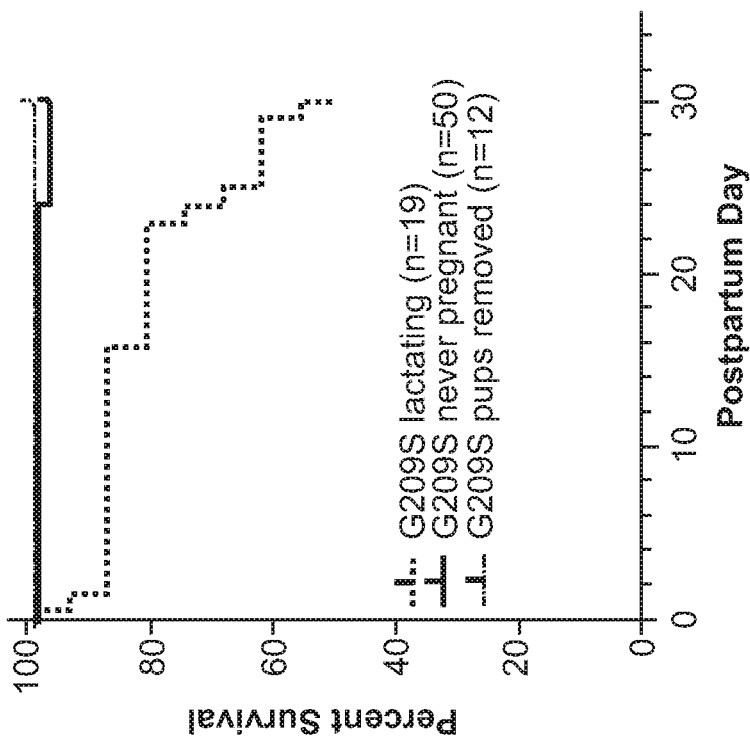
FIG. 3A is a graph depicting that in the vEDS mouse model described herein, the pregnancy and lactation is associated with 60% lethality due to arterial dissection in the first 30 days post-partum in vEDS mice.
Figure 3B:
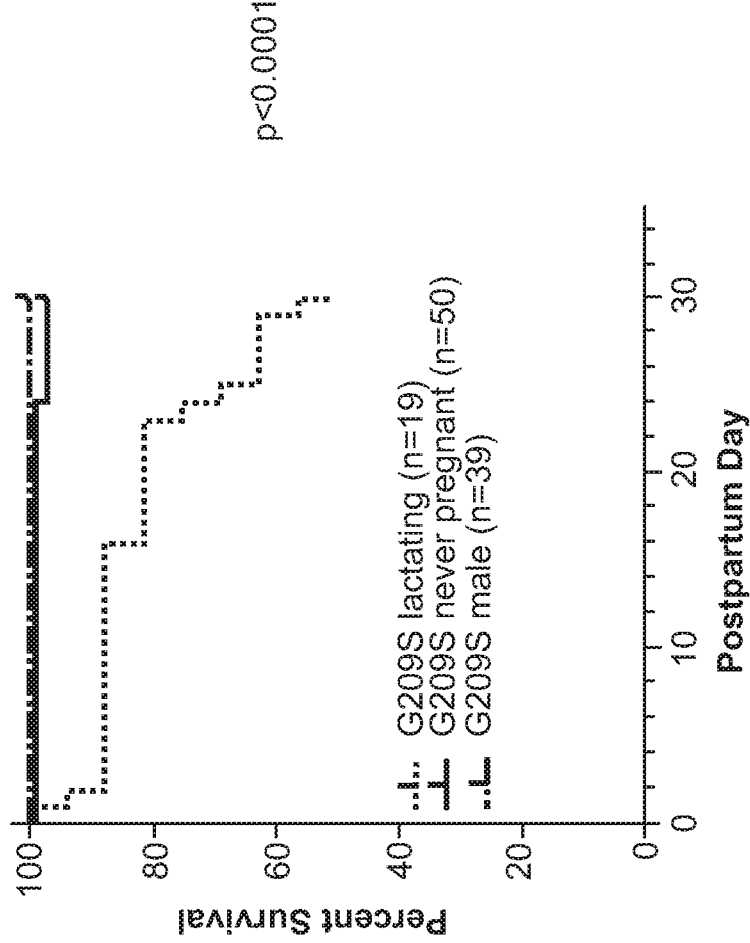
FIG. 3B is a graph depicting that prevention of lactation through pup removal after birth was able to prevent dissection and death in vEDS mice, 100% survival was observed.
Figure 3C:
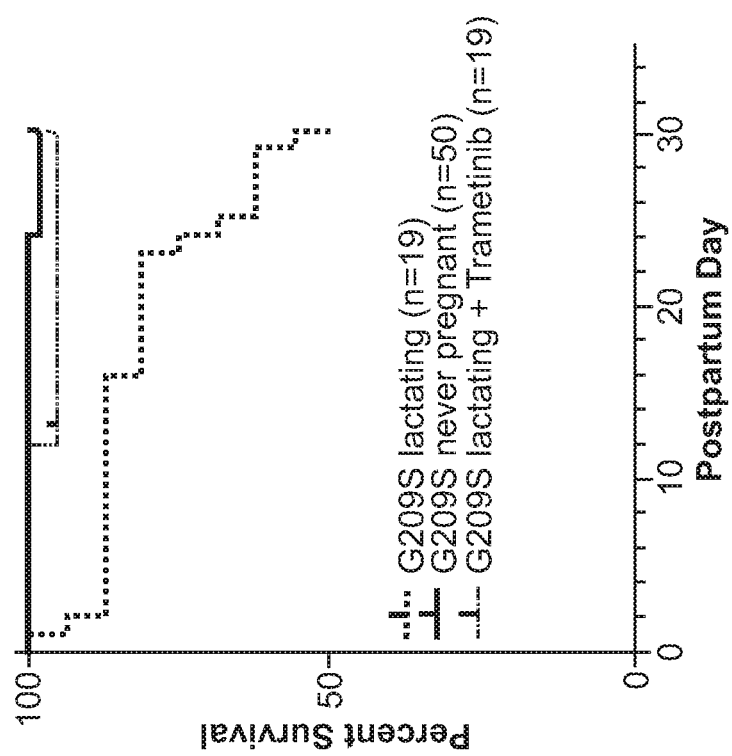
FIG. 3C is a graph depicting that near-complete survival (95%) was achieved upon treatment with hydralazine (16 mg/kg/day), which blocks the PLC/IP3/PKC/ERK axis that is activated by oxytocin.
Figure 3D:
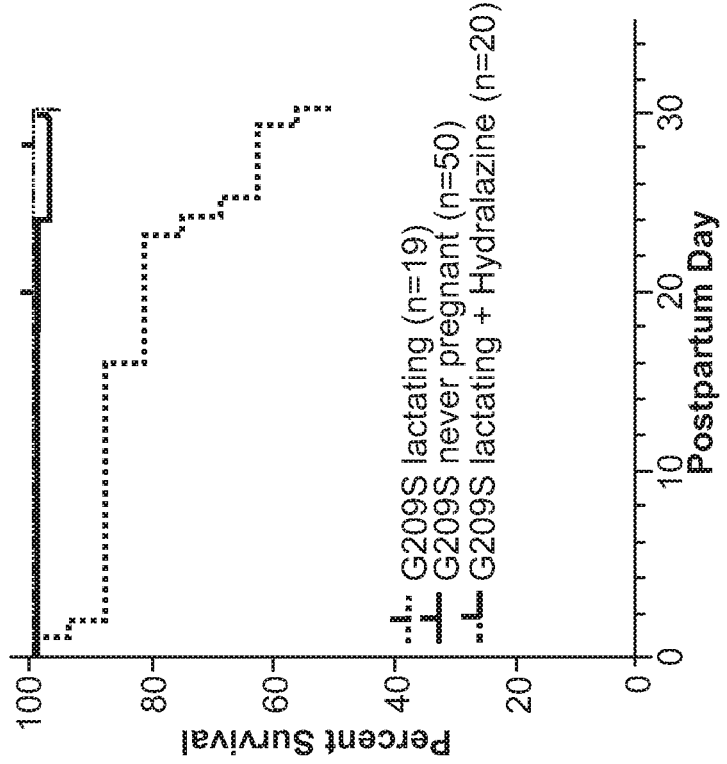
FIG. 3D is a graph depicting that protection (95% survival) was observed upon treatment with trametinib (GSK-1120212) at 1 mg/kg/day, an FDA-approved inhibitor of MEK, the kinase that activates ERK.

In the vEDS mouse model, it was identified that pregnancy and lactation was associated with 60% lethality due to arterial dissection in the first 30 days postpartum in vEDS mice (FIG. 3A). Also, prevention of lactation through pup removal after birth was able to prevent dissection and death in vEDS mice (100% survival, FIG. 3B). Further, near-complete survival (95%) was achieved upon treatment with hydralazine (16 mg/kg/day), which blocks the PLC/IP3/PKC/ERK axis that is activated by oxytocin (FIG. 3C). Similar protection (95% survival) was observed upon treatment with trametinib [GSK-1120212] (1 mg/kg/day), an FDA-approved inhibitor of MEK, the kinase that activates ERK (FIG. 3D).

Figure 3E:
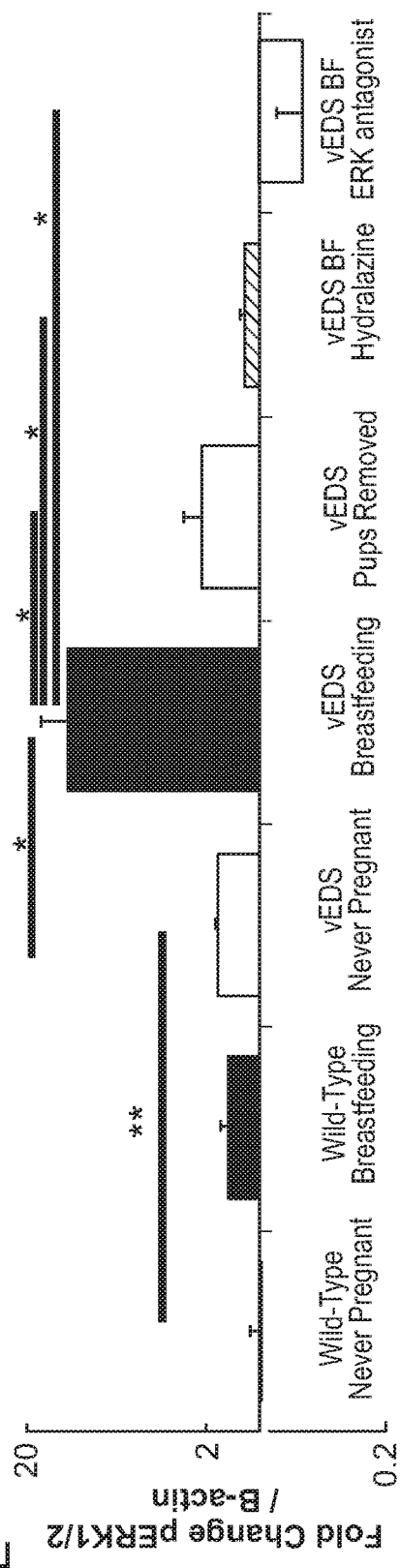
FIG. 3E is a bar graph depicting that an increased risk of death was correlated with an increase in ERK activation, while protection from aortic dissection correlated with a decrease in ERK activation, as measured by immunoblotting.
Figure 3F:
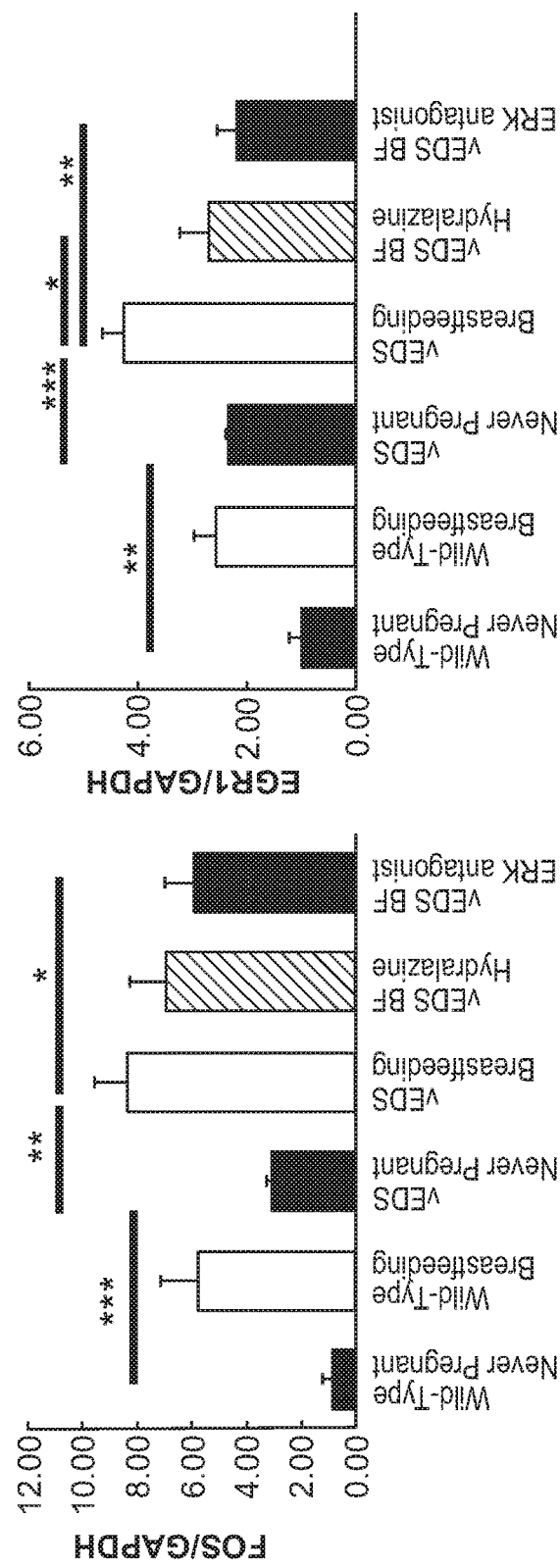
FIG. 3F is a bar graph depicting that an increased risk of death was correlated with an increase in ERK activation, while protection from aortic dissection correlated with a decrease in ERK activation, as measured by ERK target gene expression.

This increased risk of death correlated with an increase in ERK activation, while protection from aortic dissection correlated with a decrease in ERK activation, as measured by immunoblotting and by ERK target gene expression (FIG. 3E and FIG. 3F). This data further supports that increasing activation of the PLC/IP3/PKC/ERK signaling pathway lead to a significantly elevated risk of death due to aortic dissection in the mouse model of vEDS, and, further, inhibiting the PLC/IP3/PKC/ERK signaling pathway ameliorated this risk.

Example 6: Compositions and Methods for Treating Vascular Ehlers Danlos Syndrome and Associated Disorders The use of both pharmacological MEK/ERK antagonists and PKC antagonists rescues the risk of death from aortic dissection, demonstrating that PKC dependent ERK activation is a critical component of aortic disease in vEDS and that targeting this signaling pathway is beneficial in reducing aortic disease in vEDS mouse models.

Figure 16A:
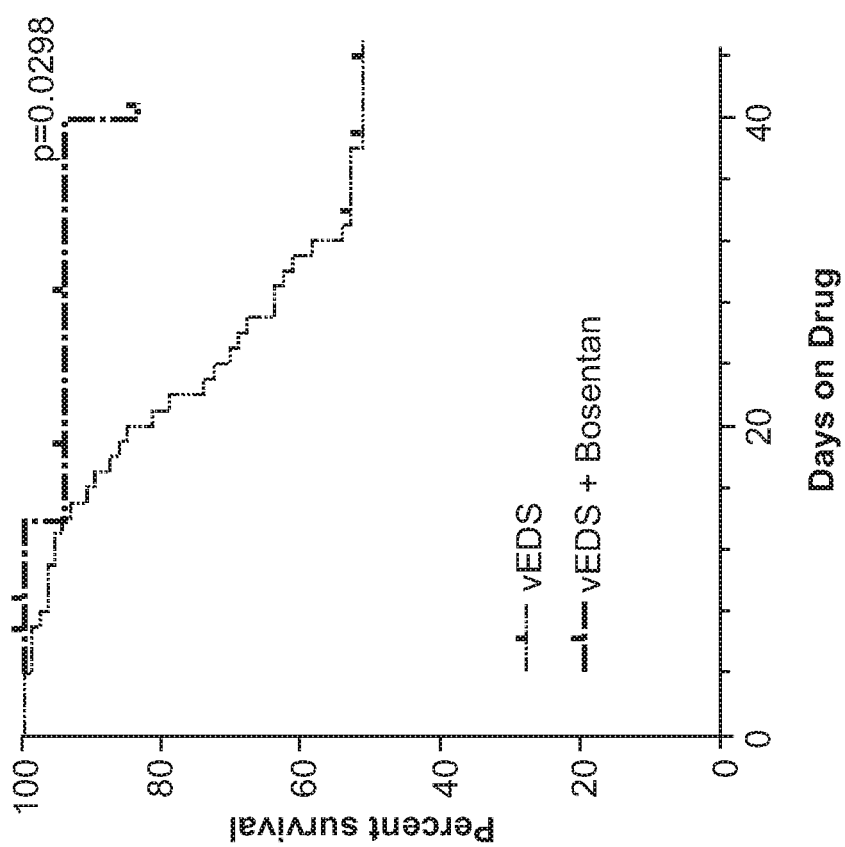
FIG. 16A is a graph demonstrating the pharmacologic inhibition of PKCβ using a second specific PKCβ inhibitor, enzastaurin.

Here it is demonstrated that pharmacologic inhibition of PKCβ using a second specific PKCβ inhibitor, enzastaurin (60 mg/kg/d), also rescued the risk of death from aortic dissection, with 80% of enzastaurin treated vEDS mice surviving after 40 days of treatment compared to only 50% of untreated vEDS mice (p=0.0305, FIG. 16A). This provides further evidence that PKCβ phosphorylation is a critical component of aortic disease in vEDS mice.

Since it was identified herein, that activation of the PLC/IP3/PKC/ERK signaling pathway is pathogenic in vEDS, the identity of the receptor which might be activating this abnormal signaling pathway was examined. GPCRs (Gq) signal through this pathway—common Gq receptors in the aorta include the angiotensin II receptor, thrombin receptor, endothelin-1 receptor, vasopressin receptor 1, sphingosine-1-phosphate receptor, alpha-1 adrenergic receptor, and serotonin receptor. However, there are also orphan GPCRs, such as GPR56 which has been shown to interact with collagen 33,4, that are also expressed in the aorta.

Figure 16B:
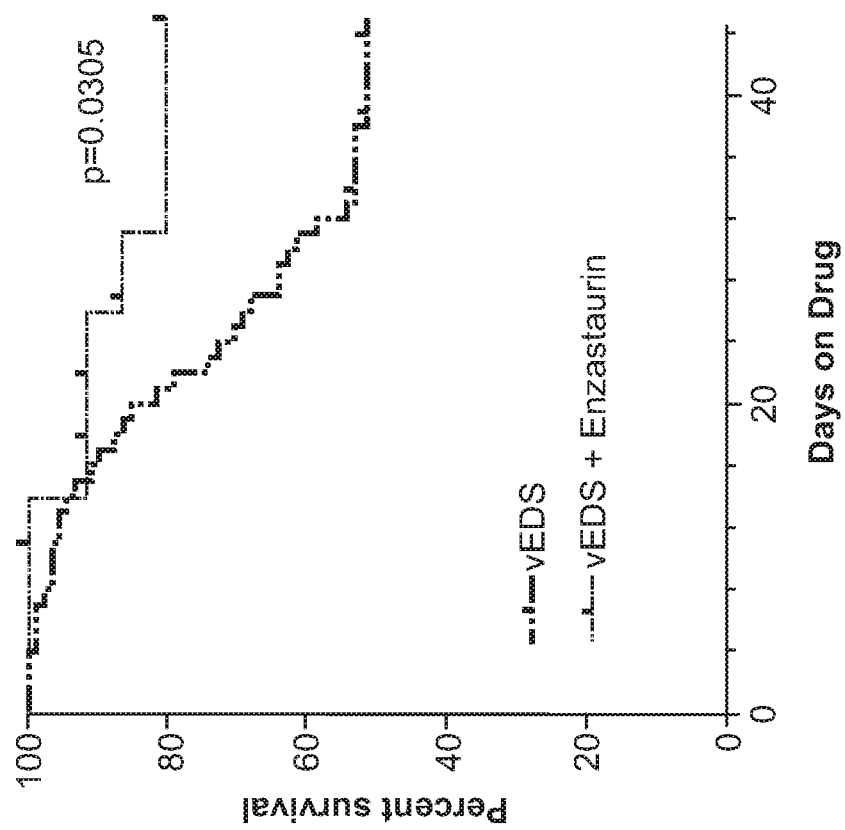
FIG. 16B is a graph demonstrating that treatment of the mice with an endothelin-receptor antagonist, bosentan, improved survival.

Without wishing to be bound by theory, it was hypothesized that if the receptor that is abnormally activated is inhibited, one would be able to identify exactly how the signaling pathway is being activated. Additionally the mice were treated mice with bosentan (100 mg/kg/d), an orally bioavailable nonspecific endothelin receptor antagonist. Treatment with bosentan led to 80% survival after 40 days of treatment, compared to only 50% survival in untreated vEDS mice (p=0.0298, FIG. 16B). This suggests that endothelin receptor signaling contributes to vEDS pathogenesis.

Figure 17:
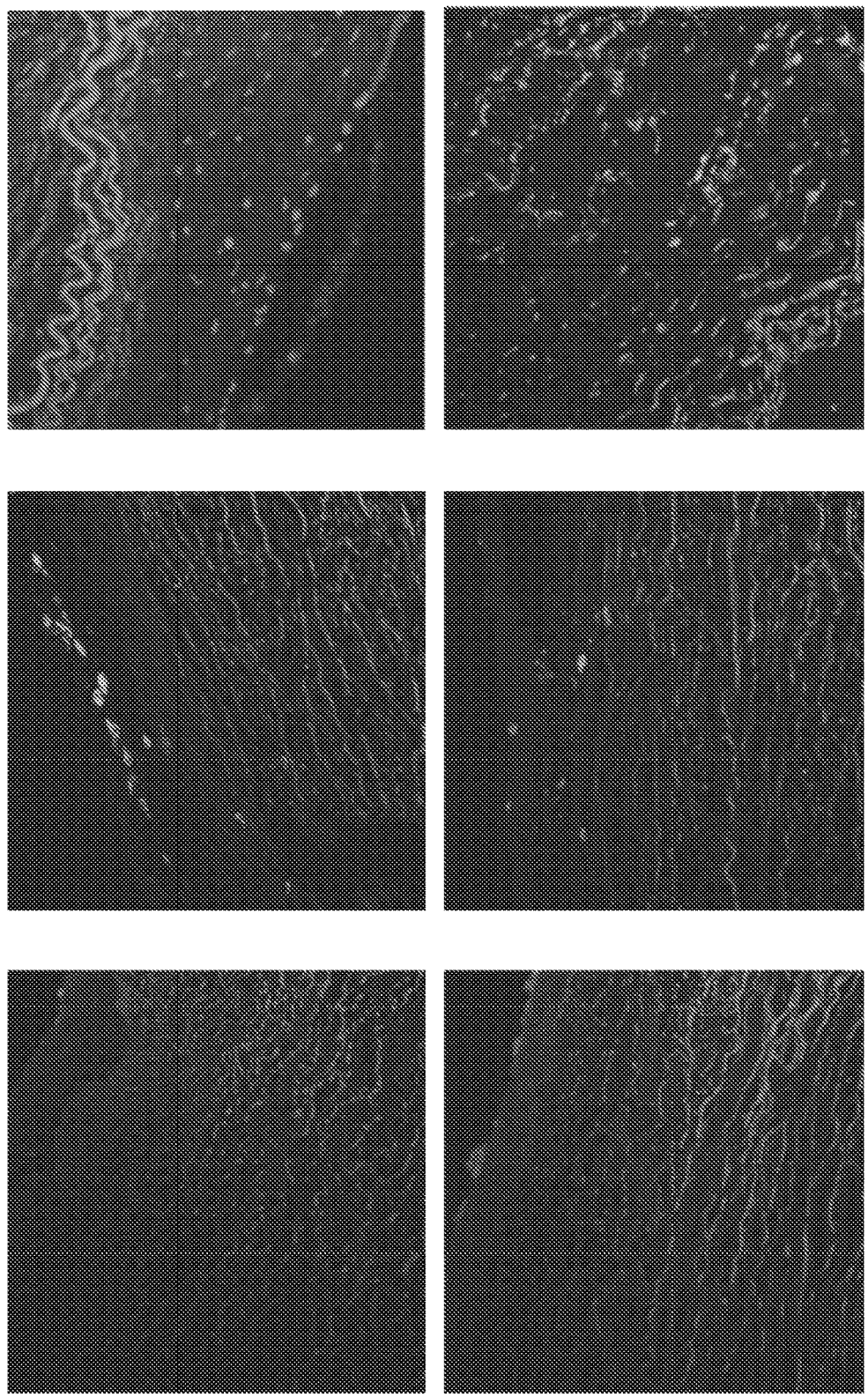
FIG. 17 is an immunofluorescent stain demonstrating that the signaling pathway is elevated in vascular tissue samples from human patients with vEDS.
Figure 18:
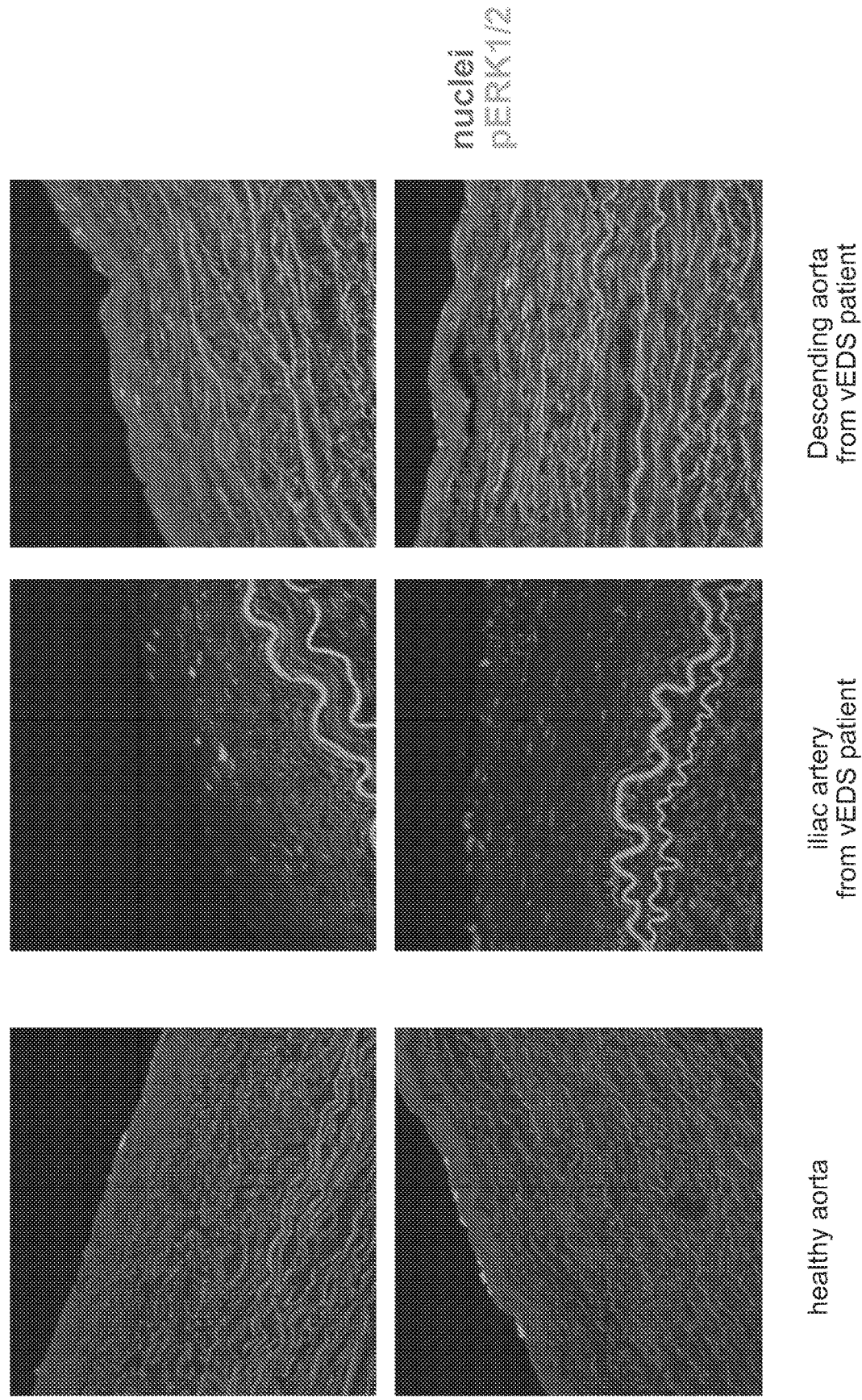
FIG. 18 is an immunofluorescent stain demonstrating that the signaling pathway is elevated in vascular tissue samples from human patients with vEDS.

The use of both pharmacological MEK/ERK antagonists and PKC antagonists rescues the risk of death from aortic dissection, demonstrating that PKC dependent ERK activation is a critical component of aortic disease in vEDS and that targeting this signaling pathway is beneficial in reducing aortic disease in vEDS mouse models. It was next sought to identify evidence that this signaling pathway is elevated in vascular tissue samples from human patients with vEDS. Both PKC phosphorylation (FIG. 17) as well ask ERK1/2 phosphorylation (FIG. 18) was identified in two tissue samples (iliac artery and descending thoracic aorta) from patients with vEDS. Neither of these phosphorylated proteins were seen in a tissue sample taken from the ascending aorta of someone without vEDS.

CONCLUSIONS

Taken together, the results provide the first evidence for a targetable signaling abnormality that contributes to the pathogenesis of vEDS. These data support the hypothesis that increased PLC/IP3/PKC signaling is driving increased MAPK/ERK activation, which in turn increases the risk of death due to aortic dissection in vEDS mouse models.

It was shown that inhibition of ERK activation through pharmacological inhibition of MEK, the activator of ERK, or pharmacological inhibition of PKC, or pharmacological inhibition of the PLC/IP3/PKC/ERK axis is sufficient to rescue death from aortic dissection. Agents that inhibit this pathway will provide therapeutic benefit for vascular Ehlers Danlos syndrome and potentially other connective tissue disorders.

Furthermore, the PLC/IP3/PKC/ERK activator might show coordinate upregulation in vEDS aortas, which is tested through analyses of candidates that emerge from the RNA-Seq profiles.

REFERENCES

1. Pepin M, Schwarze U, Superti-Furga A, Byers P H. Clinical and Genetic Features of Ehlers-Danlos Syndrome Type IV, the Vascular Type. *N Engl J Med.* 2000; 342 (10):673-680. doi:10.1056/NEJM200003093421001.
2. Pepin M G, Schwarze U, Rice K M, Liu M, Leistritz Dru, Byers P H. Survival is affected by mutation type and molecular mechanism in vascular Ehlers-Danlos syndrome (EDS type IV). *Genet Med.* 2014; 16(12):881-888. doi:10.1038/gim.2014.72.
3. Habashi J P, Judge D P, Holm T M, et al. Losartan, an AT1 Antagonist, Prevents Aortic Aneurysm in a Mouse Model of Marfan Syndrome. *Science* (80-). 2006; 312(5770): 117-121. doi:10.1126/science.1124287.
4. Holm T M, Habashi J P, Doyle J J, et al. Noncanonical TGFβ signaling contributes to aortic aneurysm progression in Marfan syndrome mice. *Science.* 2011; 332(6027): 358-361. doi:10.1126/science.1192149.
5. Habashi J P, Doyle J J, Holm T M, et al. Angiotensin II Type 2 Receptor Signaling Attenuates Aortic Aneurysm in Mice Through ERK Antagonism. *Science* (80-). 2011; 332(6027):361-365. doi:10.1126/science.1192152.
6. Judge D P, Biery N J, Keene D R, et al. Evidence for a critical contribution of haploinsufficiency in the complex pathogenesis of Marfan syndrome. *J Clin Invest.* 2004; 114(2). doi:10.1172/JCI200420641.
7. Doyle J J, Doyle A J, Wilson N K, et al. A deleterious gene-by-environment interaction imposed by calcium channel blockers in Marfan syndrome. *Elife.* 2015; 4. doi:10.7554/eLife.08648.
8. Larkin J, Ascierto P A, Dreno B, et al. Combined Vemurafenib and Cobimetinib in BRAF-Mutated Melanoma. *N Engl J Med.* 2014; 371(20):1867-1876. doi: 10.1056/NEJMoa1408868.
9. PKC-DRS2 Group L, Aiello L P, Davis M D, et al. Effect of ruboxistaurin on visual loss in patients with diabetic retinopathy. *Ophthalmology.* 2006; 113(12):2221-2230. doi:10.1016/j.ophtha.2006.07.032.
10. Gurney A M, Allam M. Inhibition of calcium release from the sarcoplasmic reticulum of rabbit aorta by hydralazine. *Br J Pharmacol.* 1995; 114(1):238-244. http://www.ncbi.nlm.nih.gov/pubmed/7712024. Accessed Sep. 24, 2018.
11. Habashi J P, Gallo E M, Bagirzadeh R, et al. Oxytocin Antagonism Prevents Pregnancy-Associated Aortic Dissection in a Mouse Model of Marfan Syndrome; 2018.

Figure 4A:
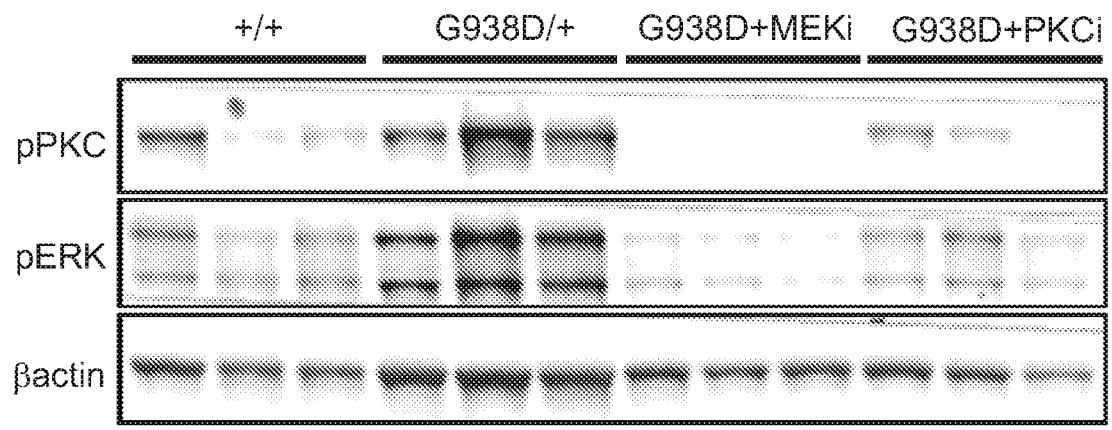
FIG. 4A is an image of an immunoblot indicating that pharmacologic inhibition of PKCβ prevented autophosphorylation of PKC as well as phosphorylation of ERK in the aortic wall, as assessed by immunoblot of aortic lysates and indicating that that pharmacologic inhibition of MEK correlated with the expected reduction in phosphorylation of ERK, the downstream substrate of MEK but also, curiously, reduced PKC phosphorylation, suggesting the presence of a positive feedback loop.
Figure 4B:
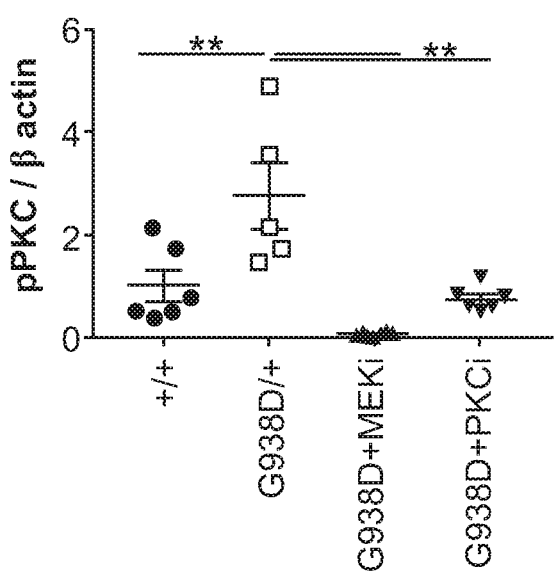
FIGS. 4B and 4C are a graphs depicting quantification of the immunoblot image depicting that pharmacologic inhibition of PKCβ prevented autophosphorylation of PKC as well as phosphorylation of ERK in the aortic wall and pharmacologic inhibition of MEK correlated with the expected reduction in phosphorylation of ERK, the downstream substrate of MEK but also, curiously, reduced PKC phosphorylation, suggesting the presence of a positive feedback loop (*p<0.05, p<0.01, *p<0.001). Neither cobimetinib nor ruboxistaurin had an effect on blood pressure.
Figure 4C:
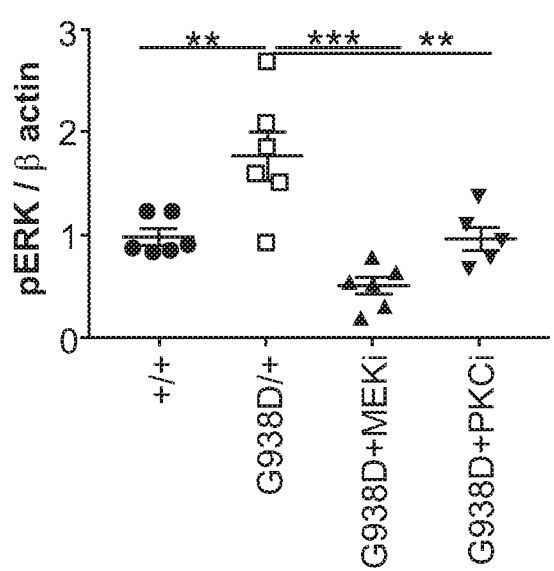
Figure 5A:
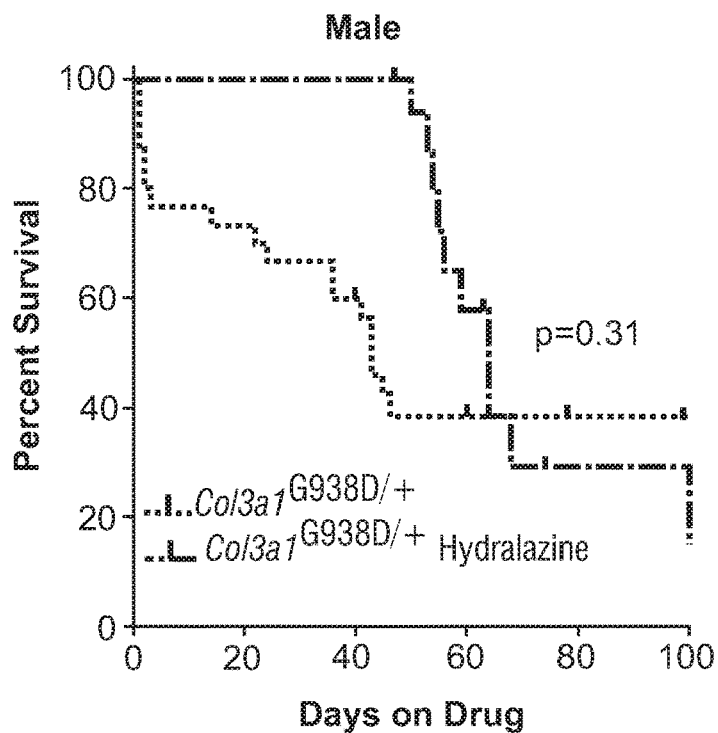
FIGS. 5A and 5B are graphs depicting that mice with hydralazine (32 mg/kg/d), which blocks the PLC/IP3/PKC/ERK axis, affords remarkable protection: 98% survival at 45 days of age, the median survival for an untreated vEDS mouse and that the survival was affected at puberty, and the risk was seen almost exclusively in male mice (FIG. 5A male mice and FIG. 5B female mice).
Figure 5B:
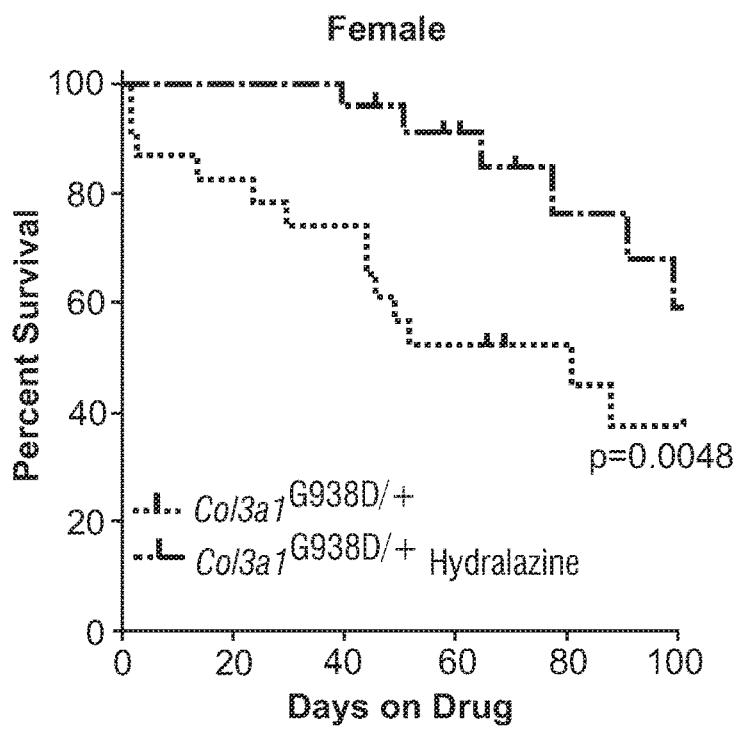

Example 7: Androgens had a Significant Role in Aortic Dissection Risk and Combination Therapy with Hydralazine Pharmacologic inhibition of PKCβ prevented autophosphorylation of PKC as well as phosphorylation of ERK in the aortic wall (FIG. 4A-4C), as assessed by immunoblot of aortic lysates. Pharmacologic inhibition of MEK correlated with the expected reduction in phosphorylation of ERK, the downstream substrate of MEK but also, curiously, reduced PKC phosphorylation, suggesting the presence of a positive feedback loop (FIG. 1, *p<0.05, p<0.01, *p<0.001). Neither cobimetinib nor ruboxistaurin had an effect on blood pressure.

Combination Therapy of Hydralazine and Bicalutamide for Treatment of vEDS

Figure 6:
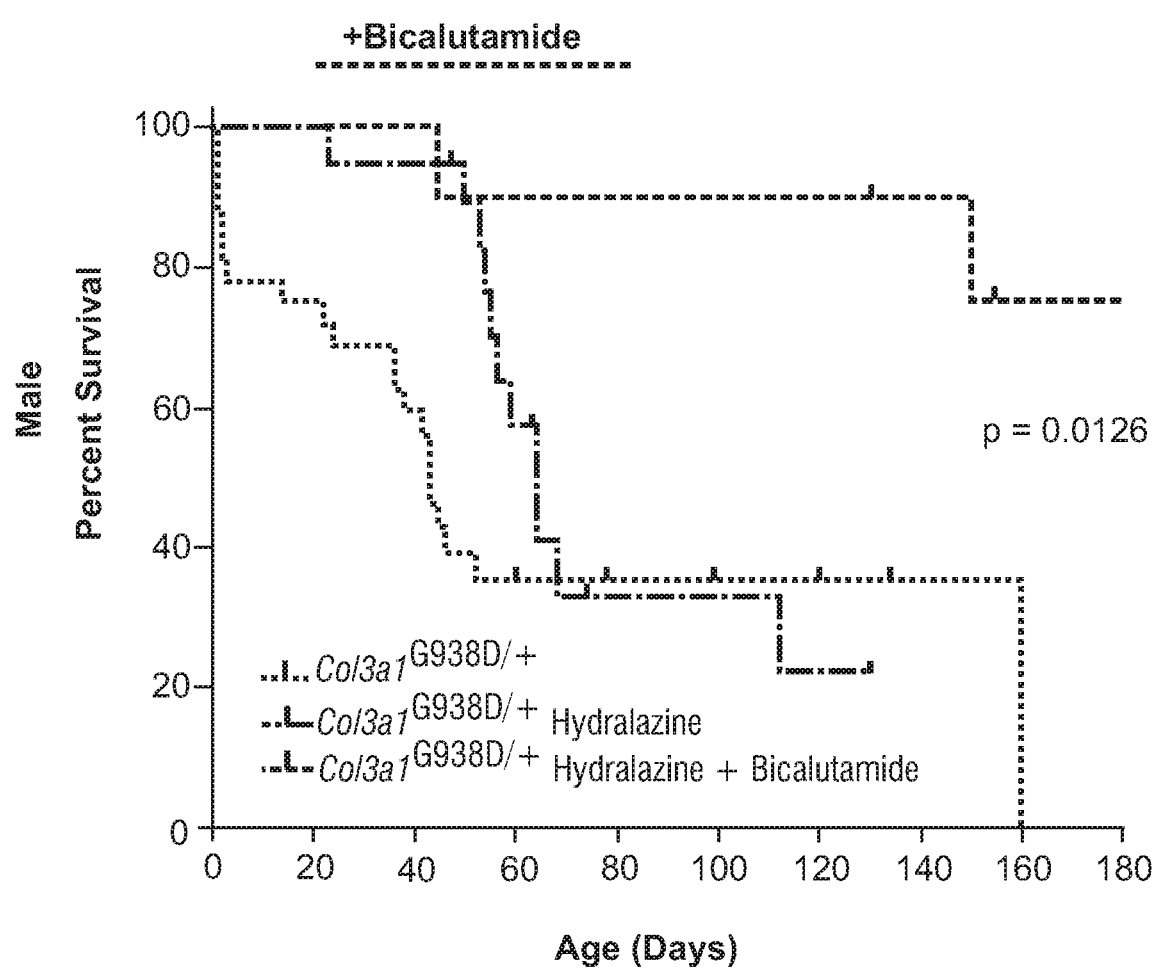
FIG. 6 is a graph depicting that the combination of hydralazine (32 mg/kg/d) with bicalutamide (50 mg/kg/d) lead to 90% survival in male mice, compared to only 24% survival in hydralazine-only treated male mice. Male mice continued to survive following removal of bicalutamide after puberty, suggesting that there was a time-dependence for androgen sensitivity in this mouse model.

Treatment of the mice with hydralazine (32 mg/kg/d), which blocks the PLC/IP3/PKC/ERK axis, affords remarkable protection: 98% survival at 45 days of age, the median survival for an untreated vEDS mouse. While the survival was affected at puberty, this risk was seen almost exclusively in male mice (FIGS. 2A and 2B) and thus it was hypothesized that treatment with an androgen antagonist may be beneficial to these mice. Indeed, the combination of hydralazine (32 mg/kg/d) with bicalutamide (50 mg/kg/d) lead to 90% survival in male mice, compared to only 24% survival in hydralazine-only treated male mice (FIG. 6).

Curiously, if bicalutamide was removed after puberty (at 90 days of life), the male mice continue to survive at the same rate while on remaining on hydralazine (FIG. 6), suggesting that there was a time-dependence for androgen sensitivity in this mouse model. Informatively, male mice treated with bicalutamide alone lead to an intermediate survival of ~80% and males did not continue to survive following removal of bicalutamide after puberty (FIG. 7) suggesting that inhibition of androgen signaling alone was not enough to prevent aortic disease in the mouse models of vEDS.

Combination Therapy of Hydralazine and Spironolactone for Treatment of vEDS

These new observations and understanding that androgens play a significant role in aortic dissection risk in our vEDS mouse models led to testing of another FDA approved medication in combination with hydralazine. Spironolactone is an FDA approved diuretic medication that has direct androgen antagonism as a side effect. Spironolactone is used off label to specifically treat acne, hirsutism, and other androgen-dependent disorders[1]. It was hypothesized that spironolactone could also be used as a direct androgen antagonist in this disorder as well.

Figure 8A:
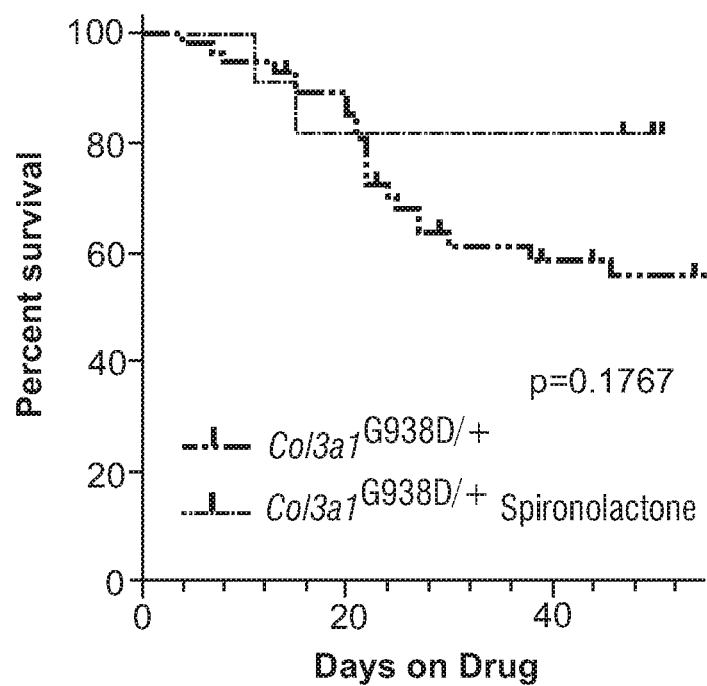
FIGS. 8A and 8B are graphs depicting that mice treated with spironolactone alone (100 mg/kg/d) showed an intermediate survival of ~80%, similar to bicalutamide alone, however, the combination of spironolactone (100 mg/kg/d) and hydralazine (32 mg/kg/d) lead to 100% survival after 50 days of treatment, similar to the combination of hydralazine and bicalutamide.
Figure 8B:
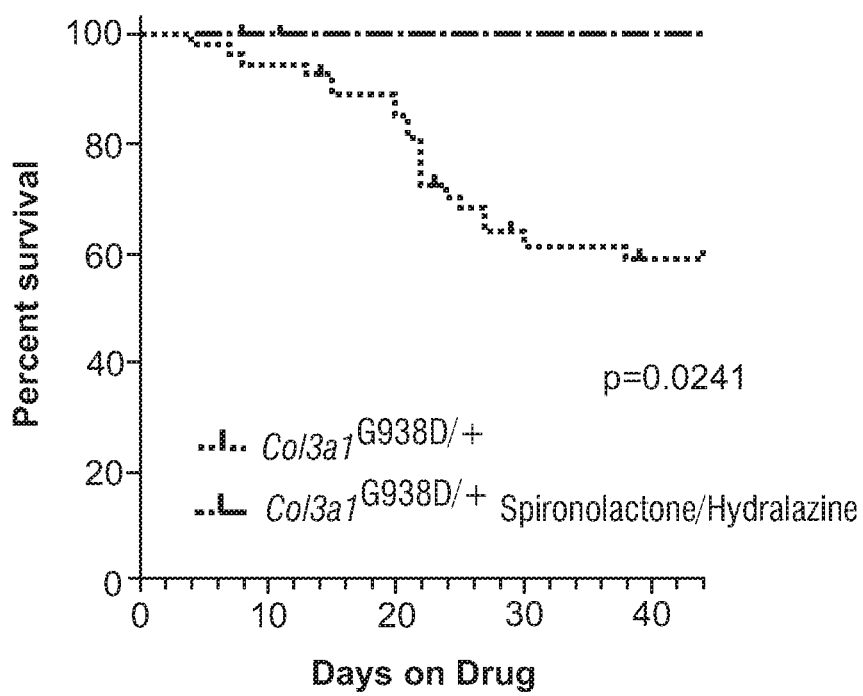

Mice were treated with spironolactone alone (100 mg/kg/d) (FIG. 8A) and an intermediate survival of ~80% was observed, similar to bicalutamide alone. However, the combination of spironolactone (100 mg/kg/d) and hydralazine (32 mg/kg/d) lead to 100% survival after 50 days of treatment, similar to the combination of hydralazine and bicalutamide (FIG. 8B).

Combination Therapy of Hydralazine and Ruboxistaurin for Treatment of vEDS

In examples, combination therapy comprising administration of hydralazine and ruboxistaurin is contemplated. Ruboxistaurin is an protein kinase C-beta (PKC-β) inhibitor and is a macrocyclic bisindolylmaleimide compound under development by Eli Lilly with potential as a therapy for diabetic macular oedema and other diabetic angiopathies, including diabetic retinopathy, diabetic peripheral neuropathy and diabetic nephropathy. Additional ruboxistaurin nomenclature include Arxxant (proposed brand name), IUPAC: (9S)-9-[(dimethylamino)methyl]-6,7,10,11-tetrahydro-9H,18H-5,21:12,17-di(metheno)dibenzo[e,k]pyrrolo[3,4-h][1,4,13]oxadiazacyclohexadecine-18,20-dione, and CAS Number: 169939-94-0.

The structure of ruboxistaurin is provided below:

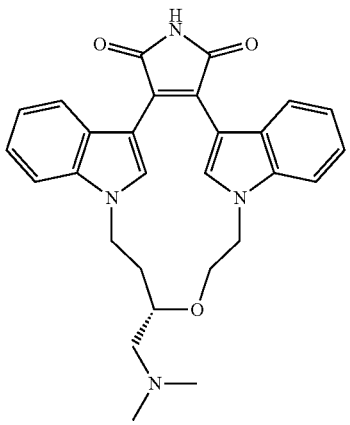 [SMILES: CN(C)C[C@@H]1CCn2cc(c3ccccc32)C2=C(C(=O)NC2=O)c2cn(c3ccccc23)CCO1]

Combination Therapy of Hydralazine and Enzastaurin for Treatment of vEDS

In examples, combination therapy comprising administration of hydralazine and enzastaurin is contemplated. Enzastaurin is a synthetic bisindolylmaleimide with potential antineoplastic activity. Binding to the ATP-binding site, enzastaurin selectively inhibits protein kinase C beta (PKC-β), an enzyme involved in the induction of vascular endothelial growth factor (VEGF)-stimulated neo-angiogenesis. This agent may decrease tumor blood supply, preventing growth. Additional enzastaurin nomenclature includes: LY-317615, IUPAC: 3-(1-Methylindol-3-yl)-4-[1-[1-(pyridin-2-ylmethyl)piperidin-4-yl]indol-3-yl]pyrrole-2,5-dione, and CAS Number: 170364-57.

The structure of enzastaurin is provided below:

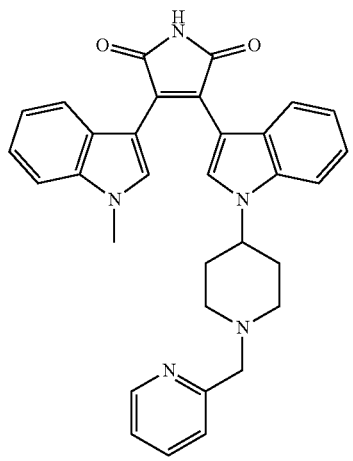 [SMILES: Cn1cc(C2=C(c3cn(C4CCN(Cc5ccccn5)CC4)c4ccccc34)C(=O)NC2=O)c2ccccc21]

Combination Therapy of Hydralazine and Sotrastaurin for Treatment of vEDS

In examples, combination therapy comprising administration of hydralazine and sotrastuarin is contemplated. Sotrastaurin (EAB071) is an investigational immunosuppressant that blocks T-lymphocyte activation through protein kinase C inhibition.

The structure of sotrastaurin is provided below:

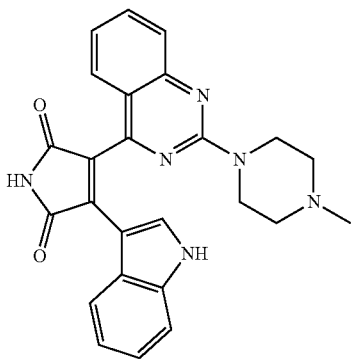 [SMILES: CN1CCN(c2nc(C3=C(c4c[nH]c5ccccc45)C(=O)NC3=O)c3ccccc3n2)CC1]

Combination Therapy of Hydralazine and Antiandrogens for Treatment of vEDS

Additional combinations of hydralazine and different antiandrogens are tested. For example, hydralazine and androgen receptor antagonists including steroidal antiandrogens (cyproterone acetate, megestrol acetate, chlormadinone acetate, oxendolone and osaterone acetate) are contemplated. Furthermore, hydralazine in combination with non-steroidal antiandrogens such as flutamide, nilutamide, topilutamide, enzalutamide, drospirenone or medrogestone are contemplated).

In other examples, a combination therapy comprising hydralazine and androgen synthesis inhibitors or antigonadotropins are contemplated. Exemplary androgen synthesis inhibitors include ketoconazole, abiraterone acetate, seviteronel, aminoglutethimide, finasteride, dutasteride, epristeride, and alfatradiol. Exemplary antigonadotropins include leuprorelin and cetrorelix. Other contemplated antiandrogens include ethinylestradiol and diethylstilbestrol.

Increased Dose of Hydralazine

Figure 9:
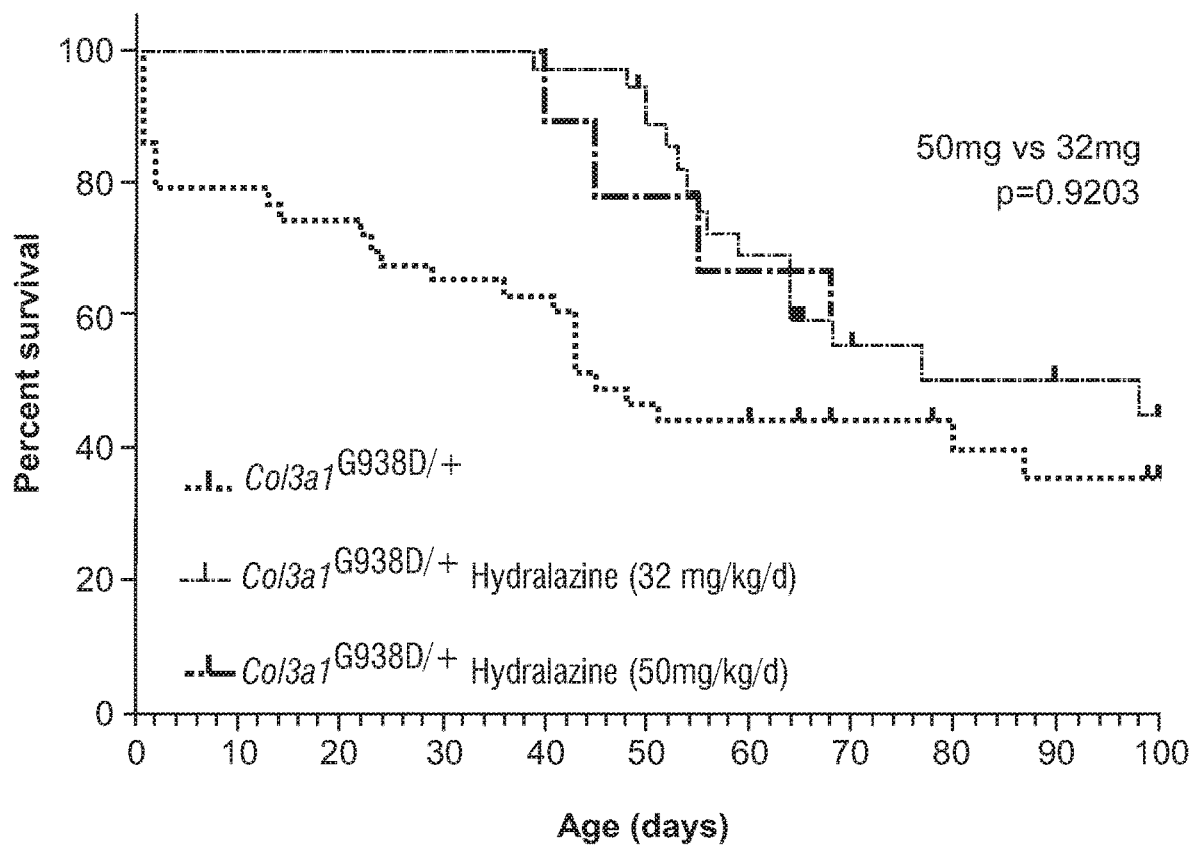
FIG. 9 is a graph depicting that mice treated with higher doses of hydralazine had an increased dose of hydralazine (50 mg/kg/d) and their survival did not improve any more than the 32 mg/kg/d dose did.

Moreover, the dose of hydralazine may be insufficient to completely inhibit this pathway in this mouse model, and that a higher dose of hydralazine may prove beneficial. Thus, these mice were treated with higher doses of hydralazine, and it was found that an increased dose of hydralazine (50 mg/kg/d) did not improve survival any more than the 32 mg/kg/d dose did (FIG. 9).

Example 8: Oxytocin-Induced Signaling

Oxytocin-induced ERK signaling was used as a method to test the hypothesis that activation of the PLC/IP3/PKC/ERK axis would worsen the risk of aortic dissection. In the vEDS mouse model described herein, pregnancy and lactation was found to be associated with 60% lethality due to arterial dissection in the first 30 days postpartum in vEDS mice, and prevention of lactation through pup removal after birth, treatment with hydralazine (16 mg/kg/d), or treatment with trametinib, was able to prevent dissection and death in vEDS mice. This increased risk of death correlated with an increase in ERK activation, while protection from aortic dissection correlated with a decrease in ERK activation, as measured by immunoblotting and by ERK target gene expression.

Figure 10A:
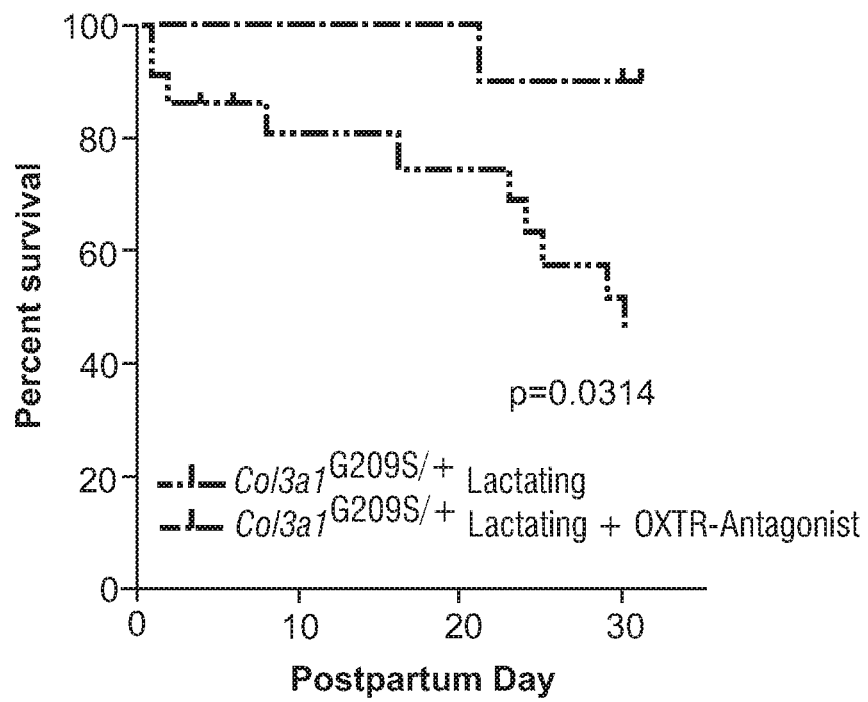
FIG. 10A is a graph depicting adding a specific oxytocin receptor antagonist 2 to the treatment of mice lead to 95% survival in the first 30 days postpartum in vEDS mice that are still lactating, which demonstrated that the significantly elevated risk of death due to aortic dissection with pregnancy was driven specifically by activation of the oxytocin receptor during breastfeeding.
Figure 10B:
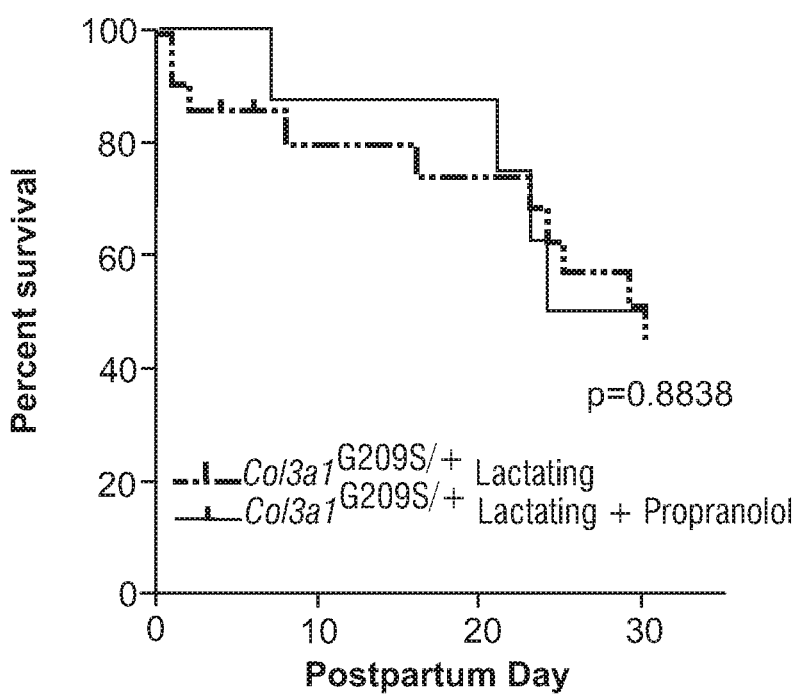
FIG. 10B is a graph depicting that propranolol, a nonspecific β antagonist that lowers blood pressure in vEDS mice does not improve survival in the first 30 days postpartum in vEDS mice that are still lactating, which demonstrated that the significantly elevated risk of death due to aortic dissection with pregnancy is not ameliorated by decreasing blood pressure.

Treatment of mice with a specific oxytocin receptor antagonist[2] was added (the selective oxytocin receptor antagonist used was des Gly-NH$_2$,d(CH$_2$)$_5$[D-Tyr$_2$,Thr$_4$] OVT), which led to 95% survival in the first 30 days postpartum in vEDS mice that were still lactating, demonstrating that the significantly elevated risk of death due to aortic dissection with pregnancy was driven specifically by activation of the oxytocin receptor during breastfeeding (FIGS. 10A and 10B).

Further, it was demonstrated that treatment with propranolol (FIG. 10B), which is the standard of care in this population and lowers blood pressure without affecting PLC/IP3/PKC/ERK signaling did not affect survival (46% survival vs. 50% survival after 30 days postpartum) in this pregnancy/breastfeeding model. This data further supports that increasing activation of the PLC/IP3/PKC/ERK signaling pathway lead to a significantly elevated risk of death due to aortic dissection in our mouse model of vEDS, and further, inhibiting the PLC/IP3/PKC/ERK signaling pathway ameliorated this risk.

GPCRs Activated the PLC/IP3/PKC/ERK Signaling Pathways

Since it was identified that activation of the PLC/IP3/PKC/ERK signaling pathway was pathogenic in vEDS, a receptor that might be activating this abnormal signaling pathway was identified. GPCRs (Gq) signal through this pathway—common Gq receptors in the aorta include the angiotensin II receptor, thrombin receptor, endothelin-1 receptor, vasopressin receptor 1, sphingosine-1-phosphate receptor, alpha-1 adrenergic receptor, and serotonin receptor. However, there are also orphan GPCRs, such as GPR56 which has been shown to interact with collagen 3[3,4], that are also expressed in the aorta.

Figure 11A:
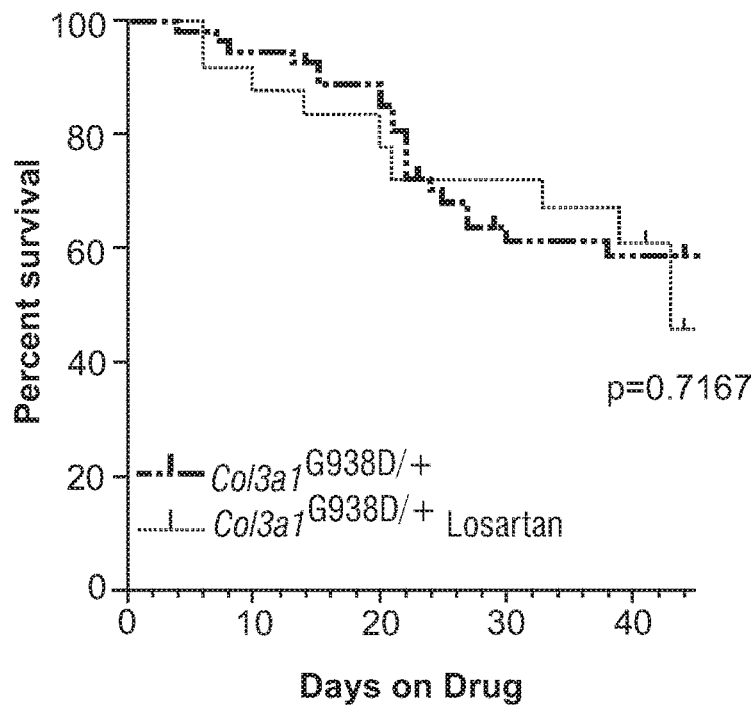
FIG. 11A is a graph indicating that inhibition of angiotensin-II signaling by treating the mice with an angiotensin receptor antagonist, losartan (60 mg/kg/d) showed no impact on survival (FIG. 11A). Treatment of the mice with a thrombin receptor antagonist, vorapraxar (1 mg/kg/d) showed found that it also had no impact on survival (FIG. 11B).
Figure 11B:
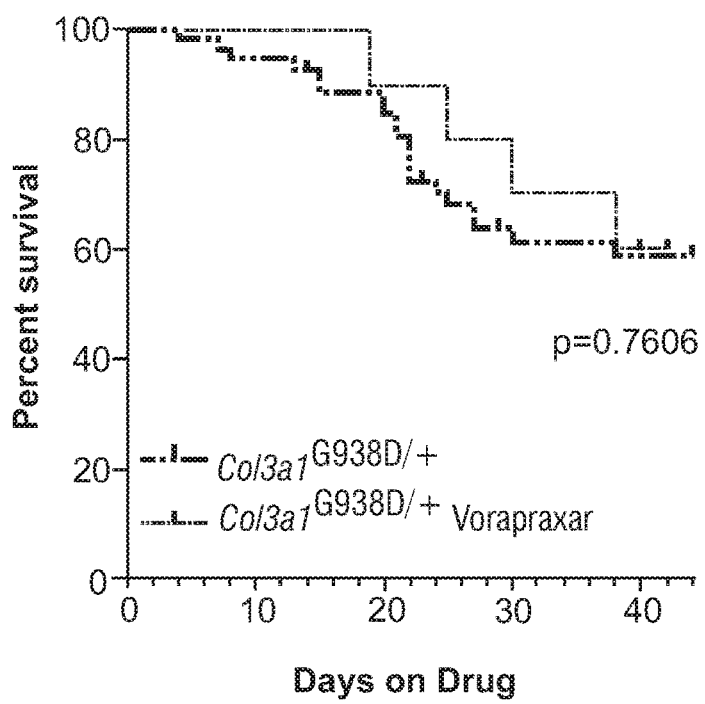

It was hypothesized that if the receptor's activity is inhibited, how the signaling pathway could being activated would be identified. Angiotensin-II signaling was first inhibited by treating the mice with an angiotensin receptor antagonist, losartan (60 mg/kg/d) (FIG. 11A), but found that it had no impact on survival. Next, the mice were treated with a thrombin receptor antagonist, vorapraxar (1mg/kg/d), but found that it also had no impact on survival (FIG. 11B).

Additional specific Gq receptor inhibitors are tested. Exemplary Gq receptor inhibitors that are tested include endothelin-1 receptor, vasopressin receptor 1, sphingosine-1-phosphate receptor, alpha-1 adrenergic receptor, serotonin receptor, and orphan GPCRs such as GPR56.

Tyrosine Kinase Receptors and the PLC/IP3/PKC/ERK Signaling Pathway

The PLC/IP3/PKC/ERK signaling pathway can also be transactivated by tyrosine kinase receptors expressed in the aorta. These include EGFR, VEGFR, FGFR, and PDGFR. To test the hypothesis that a tyrosine kinase receptor was being abnormally activated and lead to elevations in the PLC/IP3/PKC/ERK signaling pathway, treated were treated with a nonspecific tyrosine kinase receptor antagonist, nintedanib (50 mg/kg/d), but found that it also had no impact on survival (FIG. 12). This suggested that tyrosine kinase receptor activation was not driving the activation of PLC/IP3/PKC/ERK signaling pathway in vEDS mice.

Beta-Adrenergic Receptor Blockers and Risk of Aortic Rupture

Figure 14:
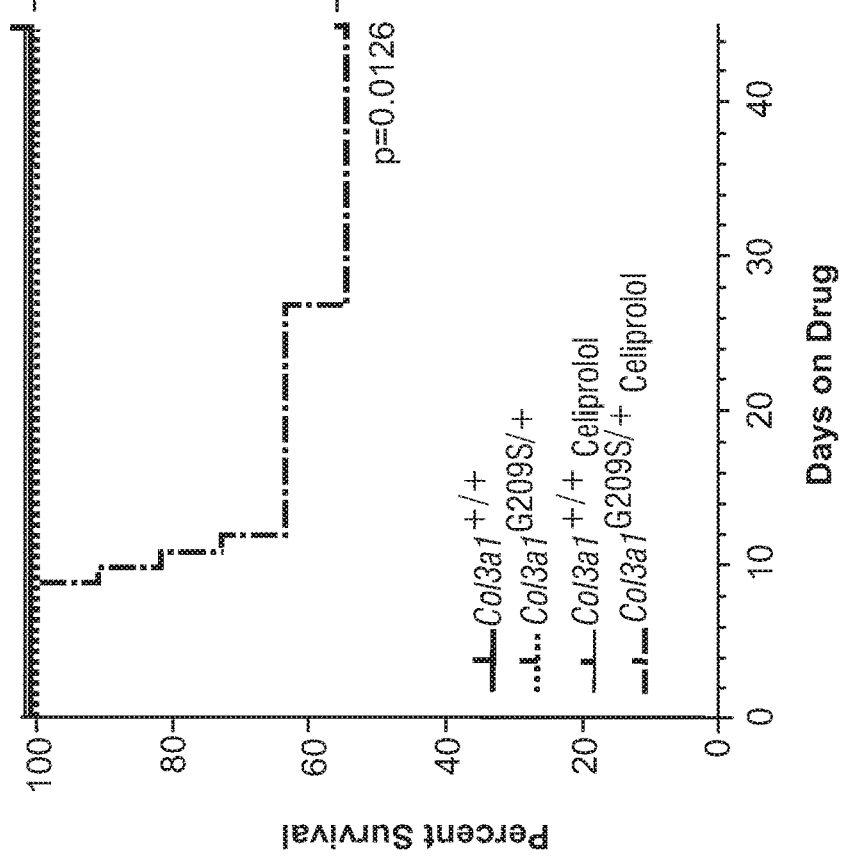
FIG. 14 is a graph depicting celiprolol, which accelerates the risk of aortic dissection in the mouse models, and the vEDS mutation with the Col3a1$^{G209S/+}$ mutation, also demonstrated increased risk of aortic dissection on celiprolol.

Others have proposed[5-8] that vEDS phenotypes are a result of chronically "weak" tissue and therefore propose that decreasing blood pressure with beta-adrenergic receptor blockers should decrease the risk of aortic rupture in these patients. To address this hypothesis, the mice with a nonspecific β antagonist, propranolol (80 mg/kg/d), a specific β1 antagonist, atenolol (120 mg/kg/d), and a β1 antagonist/β2 agonist, celiprolol (200 mg/kg/d), but found that none of these manipulations lead to an improvement in survival in our vEDS mouse models (FIG. 13A-13C) despite decreases in blood pressure. Celiprolol even accelerated the risk of aortic dissection in the mouse models, and the vEDS mutation with the Col3a1$^{G209S/+}$ mutation also demonstrated increased risk of aortic dissection on celiprolol (FIG. 14). Since this was not common to all β antagonists, this observation could be driven by celiprolol's β2 agonism activity.

Figure 15:
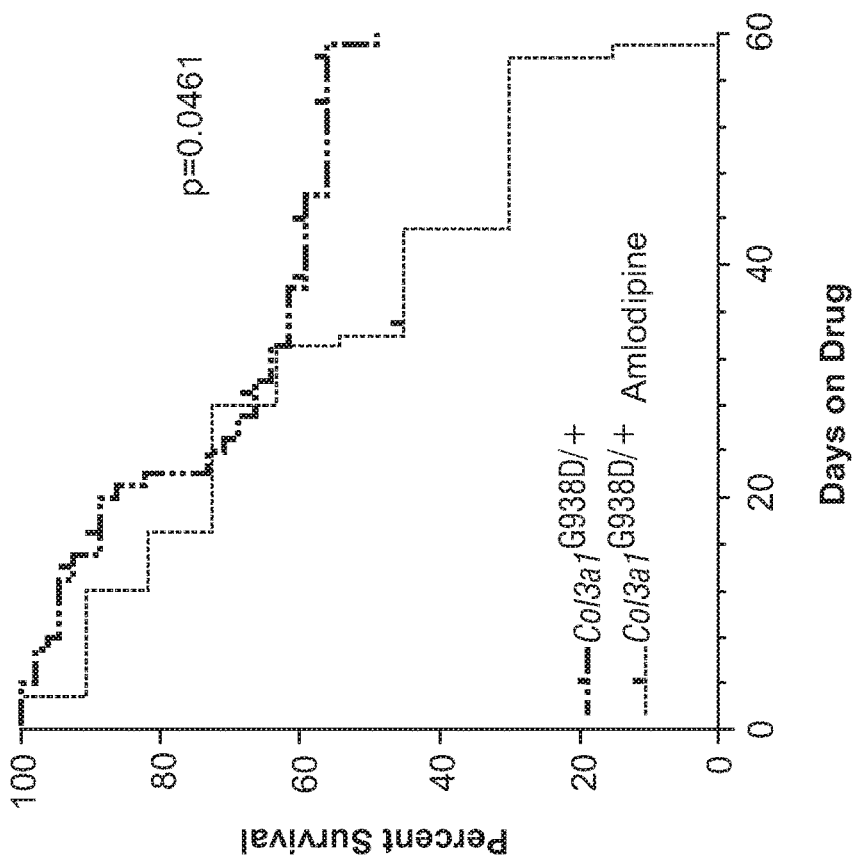
FIG. 15 is a graph depicting that amlodipine (12 mg/kg/d) also increased the risk of aortic dissection in the mouse model, and this has been shown to be consistent with MFS mice as well.

Calcium channel blockers, which lower blood pressure by another mechanism were also tested. It was found that amlodipine (12 mg/kg/d) also increased the risk of aortic dissection in the mouse model, and this has been shown to be consistent with MFS (Marfan Syndrome) mice as well[9] (FIG. 15).

Example 9: Treatment of Marfan Syndrome with Protein Kinase C-Beta (PKC-β) Inhibitors In examples, different PKC-β inhibitors are used for the treatment of Marfan Syndrome. For example, treatment of Marfan Syndrome may include administration of ruboxistaurin. Here it is demonstrated that pharmacologic inhibition of PKCβ using ruboxistaurin (10 mg/kg/d), rescued the aortic root growth in Marfan syndrome mice, (p=2E-4, FIG. 19). In other examples, treatment of Marfan Syndrome includes administration of enzastaurin or sotrastaurin.

Combination Therapy of Hydralazine and Antiandrogens for Treatment of vEDS

Additional combinations of hydralazine and different antiandrogens are tested. For example, hydralazine and androgen receptor antagonists including steroidal antiandrogens (cyproterone acetate, megestrol acetate, chlormadinone acetate, oxendolone and osaterone acetate) are contemplated. Furthermore, hydralazine in combination with non-steroidal antiandrogens such as flutamide, nilutamide, topilutamide, enzalutamide, drospirenone or medrogestone are contemplated).

In other examples, a combination therapy comprising hydralazine and androgen synthesis inhibitors or antigonadotropins are contemplated. Exemplary androgen synthesis inhibitors include ketoconazole, abiraterone acetate, seviteronel, aminoglutethimide, finasteride, dutasteride, epristeride, and alfatradiol. Exemplary antigonadotropins include leuprorelin and cetrorelix. Other contemplated antiandrogens include ethinylestradiol and diethylstilbestrol.

Example 10: Pharmacological Inhibition Increases Survival in vEDS Mice

Pharmacological PKC Inhibition with Enzastaurin Increases Survival in vEDS Mice

Both the Col3a1 G209S/+ and Col3a1 G938D/+ mouse models recapitulated vEDS phenotypes and are used to test agents for the treatment of vEDS. Mice are treated with a well-tolerated orally administered agent, enzastaurin at about 30 mg/kg/day. By binding to the ATP-binding site, enzastaurin selectively inhibits protein kinase C beta (PKC-β), and thus it is hypothesized that a pharmacologic PKC inhibitor will rescue the risk of death from aortic dissection. A survival rate of about 100% is observed after about 30 days (1 month) of treatment, as compared to a significantly decreased survival rate in mice with no treatment (e.g., a statistically significant difference compared to the control mice).

The mice are also treated for at least about 45 days and the survival rate of enzastaurin-treated mice to control mice is evaluated.

The mice are also treated with higher doses of enzastaurin, e.g., about 40 mg/kg/day, 50 mg/kg/day, or 100 mg/kg/day. In other examples, mice are treated once daily or twice daily with enzastaurin.

These results suggest that inhibition of excessive PLC/IP3/PKC/ERK signaling with enzastaurin in the aorta rescues risk of death due to aortic dissection in the mouse model of vEDS.

Pharmacological PKC Inhibition with Sotrastaurin Increases Survival in vEDS Mice Additional studies using the mouse models described herein (e.g., Col3a1 G209S/+ and Col3a1 G938D/+ mouse models) are used to test for additional agents for the treatment of vEDS. Mice treated with a well-tolerated orally administered agent, sotrastaurin at about 30 mg/kg/day is evaluated. Sotrastaurin (AEB071) is an immunosuppressant that blocks T-lymphocyte activation through protein kinase C inhibition. Similar to enzastaurin, it is hypothesized that a PKC inhibitor (e.g., sotrastaurin) will also rescue the risk of death from aortic dissection. A survival rate of about 100% is observed after about 30 days (1 month) of treatment, as compared to a significantly decreased survival rate in mice with no treatment (e.g., a statistically significant difference compared to the control mice). The mice are also treated for at least about 45 days and the survival rate of sotrastaurin-treated mice to control mice is evaluated.

The mice are also treated with higher doses of sotrastaurin, e.g., about 40 mg/kg/day, 50 mg/kg/day, or 100 mg/kg/day. In other examples, mice are treated once daily or twice daily with sotrastaurin.

These results provide evidence that inhibition of excessive PLC/IP3/PKC/ERK signaling with sotrastaurin in the aorta rescues risk of death due to aortic dissection in the mouse model of vEDS.

REFERENCES

1. Zaenglein A L. Acne Vulgaris. Solomon C G, ed. *N Engl J Med*. 2018; 379(14):1343-1352.
2. Manning M, Misicka A, Olma A, et al. Oxytocin and Vasopressin Agonists and Antagonists as Research Tools and Potential Therapeutics. *J Neuroendocrinol*. 2012; 24(4):609-628.
3. Luo R, Jin Z, Deng Y, Strokes N, Piao X. Disease-Associated Mutations Prevent GPR56-Collagen III Interaction. Mei L, ed. *PLoS One*. 2012; 7(1):e29818.
4. Luo R, Jeong S-J, Yang A, et al. Mechanism for Adhesion G Protein-Coupled Receptor GPR56-Mediated RhoA Activation Induced By Collagen III Stimulation. 2014.
5. Ong K T, Perdu J, De Backer J, et al. Effect of celiprolol on prevention of cardiovascular events in vascular Ehlers-Danlos syndrome: A prospective randomised, open, blinded-endpoints trial. *Lancet*. 2010; 376(9751):1476-1484.
6. D'hondt S, Guillemyn B, Syx D, et al. Type III collagen affects dermal and vascular collagen fibrillogenesis and tissue integrity in a mutant Col3a1 transgenic mouse model. *Matrix Biol*. 2018; 70:72-83.
7. Briest W, Cooper T K, Tae H-J, Krawczyk M, McDonnell N B, Talan M I. Doxycycline ameliorates the susceptibility to aortic lesions in a mouse model for the vascular type of Ehlers-Danlos syndrome. *J Pharmacol Exp Ther*. 2011; 337(3).
8. Shalhub S, Black J H, Cecchi A C, et al. Molecular diagnosis in vascular Ehlers-Danlos syndrome predicts pattern of arterial involvement and outcomes. *J Vasc Surg*.
9. Doyle J J, Doyle A J, Wilson N K, et al. A deleterious gene-by-environment interaction imposed by calcium channel blockers in Marfan syndrome. *Elife*. 2015; 4.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank and NCBI submissions indicated by accession number cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

We claim:

1. A method of treating vascular Ehlers-Danlos Syndrome (vEDS) in a subject in need thereof, the method comprising:
administering to the subject an effective amount of an agent selected from ruboxistaurin, enzastaurin, sotrastaurin, or a pharmaceutically acceptable salt thereof.

2. The method of claim 1, wherein the agent comprises ruboxistaurin, or a pharmaceutically acceptable salt thereof.

3. The method of claim 1, wherein the agent comprises enzastaurin, or a pharmaceutically acceptable salt thereof.

4. The method of claim 1, wherein the agent comprises sotrastaurin, or a pharmaceutically acceptable salt thereof.

5. The method of claim 1, wherein the effective amount of the agent is from about 0.001 mg/kg to 250 mg/kg body weight.

6. The method of claim 1, wherein the effective amount of the agent is from about is from about 0.05 mg/kg to about 50 mg/kg body weight.

7. A method of treating a vascular Ehlers-Danlos Syndrome in a subject in need thereof, the method comprising:
administering to the subject an effective amount of enzastaurin.

8. The method of claim 7, wherein the effective amount of the agent is from about 1 mg/kg to about 15 mg/kg.

9. The method of claim 7, wherein the effective amount of the agent is from about 1 mg/kg to about 30 mg/kg.

10. A method of treating a vascular Ehlers-Danlos Syndrome (vEDS) in a subject in need thereof, the method comprising:
administering to the subject an effective amount of an agent, wherein the agent is chosen from: cobimetinib, hydralazine or trametinib, or a pharmaceutically acceptable salt thereof.

11. The method of claim 1, further comprising administering an effective amount of a vasodilator or an oxytocin receptor antagonist 2.

12. The method of claim 11, wherein a vasodilator is administered that is U-73122, U73343, ET-18-OCH$_3$, 2-APB, xestospongin C, or hydralazine.

13. The method of claim 10, wherein the effective amount of the agent is from about 0.001 mg/kg to 250 mg/kg body weight.

14. The method of claim 7, further comprising administering an effective amount of a vasodilator or an oxytocin receptor antagonist 2.

15. The method of claim 14, wherein a vasodilator is administered that is U-73122, U73343, ET-18-OCH$_3$, 2-APB, xestospongin C, or hydralazine.

16. The method of claim 7, wherein the effective amount of the agent is from about 0.001 mg/kg to 250 mg/kg body weight.

17. The method of claim 10, further comprising administering an effective amount of a vasodilator or an oxytocin receptor antagonist 2.

18. The method of claim 17, wherein a vasodilator is administered that is U-73122, U73343, ET-18-OCH$_3$, 2-APB, xestospongin C, or hydralazine.

19. A method of treating a vascular Ehlers-Danlos Syndrome (vEDS) in a subject in need thereof, the method comprising:
administering to the subject an effective amount of a small molecule inhibitor of extracellular signal-regulated kinase (ERK) or protein kinase C (PKC).

20. The method of claim 19 wherein an effective amount of a small molecule inhibitor of extracellular signal-regulated kinase (ERK) is administered.

21. The method of claim 19 wherein an effective amount of a small molecule inhibitor of protein kinase C (PKC) is administered.

22. The method of claim 19 wherein the subject is identified as suffering from vEDS and the small molecule inhibitor is administered to the identified subject.

23. The method of claim 20 wherein the subject is identified as suffering from vEDS and the small molecule inhibitor is administered to the identified subject.

24. The method of claim 21 wherein the subject is identified as suffering from vEDS and the small molecule inhibitor is administered to the identified subject.

25. The method of claim 1 wherein the subject is identified as suffering from vEDS and ruboxistaurin, enzastaurin or sotrastaurin is administered to the identified subject.

26. The method of claim 7 wherein the subject is identified as suffering from vEDS and enzastaurin is administered to the identified subject.

27. The method of claim 10 wherein the subject is identified as suffering from vEDS and cobimetinib, hydralazine or trametinib is administered to the identified subject.

28. The method of claim 10 wherein the subject is identified as suffering from vEDS and cobimetinib is administered to the identified subject.

29. The method of claim 10 wherein the subject is identified as suffering from vEDS and hydralazine is administered to the identified subject.

30. The method of claim 10 wherein the subject is identified as suffering from vEDS and trametinib is administered to the identified subject.

* * * * *